(12) United States Patent
Xu et al.

(10) Patent No.: US 9,656,996 B2
(45) Date of Patent: May 23, 2017

(54) FUSED HETEROCYCLIC COMPOUND, PREPARATION METHOD THEREFOR, PHARMACEUTICAL COMPOSITION, AND USES THEREOF

(71) Applicant: SHANGHAI YINGLI PHARMACEUTICAL CO., LTD., Shanghai (CN)

(72) Inventors: Zusheng Xu, Shanghai (CN); Yangtong Lou, Shanghai (CN)

(73) Assignee: SHANGHAI YINGLI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/029,882

(22) PCT Filed: Sep. 19, 2014

(86) PCT No.: PCT/CN2014/086914
§ 371 (c)(1),
(2) Date: Apr. 15, 2016

(87) PCT Pub. No.: WO2015/055071
PCT Pub. Date: Apr. 23, 2015

(65) Prior Publication Data
US 2016/0244432 A1 Aug. 25, 2016

(30) Foreign Application Priority Data

Oct. 16, 2013 (CN) .......................... 2013 1 0485200

(51) Int. Cl.
*C07D 239/84* (2006.01)
*C07D 401/04* (2006.01)
(Continued)

(52) U.S. Cl.
CPC ......... *C07D 401/14* (2013.01); *C07D 239/84* (2013.01); *C07D 401/04* (2013.01);
(Continued)

(58) Field of Classification Search
CPC .. C07D 239/84; C07D 401/04; C07D 403/04; C07D 473/34; C07D 401/14;
(Continued)

(56) References Cited

U.S. PATENT DOCUMENTS 7,235,551 B2  6/2007 Adams
7,629,462 B2 12/2009 Adams
(Continued)

FOREIGN PATENT DOCUMENTS

AU 2014336775 A1 4/2016
CA 2926596 A1 4/2015
(Continued)

OTHER PUBLICATIONS

STN Registry No. 1349713-70-7; Publication Date (Entered STN): Dec. 6, 2011.*
(Continued)

*Primary Examiner* — Alicia L Otton
*Assistant Examiner* — Sagar Patel
(74) *Attorney, Agent, or Firm* — Millen White Zelano and Branigan, PC; John Sopp; Anthony Zelano

(57) ABSTRACT

Disclosed are a fused heterocyclic compound, a preparation method therefor, a pharmaceutical composition, and uses thereof. The preparation method of the fused heterocyclic compound and/or the pharmaceutically acceptable salt thereof in the present invention comprises three synthesizing routes. The present invention also provides a pharmaceutical composition, containing one or more of the fused heterocyclic compound, the pharmaceutically acceptable salt, hydrates, solvent compounds, polymorphs and prodrugs thereof, and a pharmaceutically acceptable carrier. The present invention also relates to an application of the fused heterocyclic compound and/or the pharmaceutical composition in preparing kinase inhibitors and in preparing drugs for preventing and treating diseases related to kinase. The fused heterocyclic compound of the present invention has selective inhibition function on PI3K δ, and can be used for preparing drugs for preventing and treating cell proliferation diseases such as cancers, infections, inflammations, or autoimmune diseases.

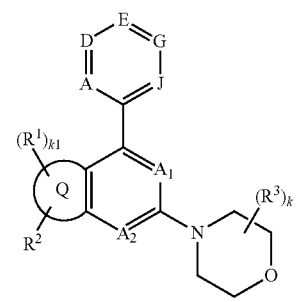

I

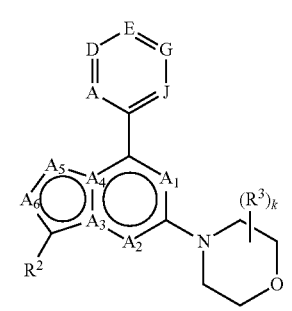

II (Continued)

-continued

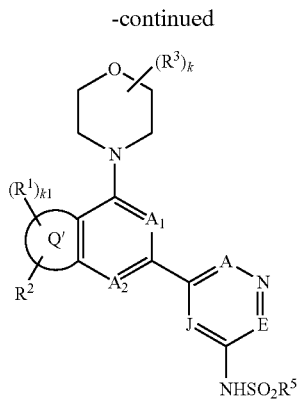

15 Claims, No Drawings

(51) Int. Cl.
| | |
|---|---|
| C07D 401/14 | (2006.01) |
| C07D 403/04 | (2006.01) |
| C07D 473/34 | (2006.01) |
| C07D 473/32 | (2006.01) |
| C07D 495/04 | (2006.01) |
| C07D 487/04 | (2006.01) |
| A61K 31/5377 | (2006.01) |
| A61K 31/498 | (2006.01) |
| A61K 31/635 | (2006.01) |
| A61K 31/4985 | (2006.01) |
| C07D 405/14 | (2006.01) |

(52) U.S. Cl.
CPC ......... *C07D 403/04* (2013.01); *C07D 405/14* (2013.01); *C07D 473/34* (2013.01); *C07D 487/04* (2013.01); *C07D 495/04* (2013.01)

(58) Field of Classification Search
CPC .. C07D 473/32; C07D 495/04; C07D 487/04; A61K 31/5377; A61K 31/498; A61K 31/635; A61K 31/4985
USPC ..... 544/116, 106, 284, 278, 256; 514/234.8, 514/266.21, 263.22, 261.1, 258.1
See application file for complete search history.

(56) References Cited

U.S. PATENT DOCUMENTS

| | | | |
|---|---|---|---|
| 7,700,768 | B2 | 4/2010 | Adams |
| 8,247,410 | B2 | 8/2012 | Nagaraj |
| 8,435,988 | B2 | 5/2013 | Qu |
| 8,541,411 | B2 | 9/2013 | Qu |
| 8,586,582 | B2 | 11/2013 | Liang |
| 8,609,838 | B2 | 12/2013 | Nagaraj |
| 8,912,178 | B2 | 12/2014 | Liang |
| 2004/0266780 | A1 | 12/2004 | Sadhu |
| 2007/0293492 | A1 | 12/2007 | DeVita |
| 2010/0069629 | A1 | 3/2010 | Shimma et al. |
| 2010/0298319 | A1 | 11/2010 | Nagaraj et al. |
| 2010/0324284 | A1 | 12/2010 | Ebiike et al. |
| 2011/0009403 | A1 | 1/2011 | Nagaraj et al. |
| 2011/0130395 | A1 | 6/2011 | Liang et al. |
| 2012/0015931 | A1 | 1/2012 | Li |
| 2012/0208808 | A1 | 8/2012 | Buchstaller et al. |
| 2013/0072481 | A1 | 3/2013 | Liang et al. |
| 2013/0123255 | A1 | 5/2013 | Tanimura et al. |
| 2015/0246929 | A1 | 9/2015 | Xu et al. |
| 2016/0207927 | A1 | 7/2016 | Chen et al. |
| 2016/0244432 | A1 | 8/2016 | Xu et al. |

FOREIGN PATENT DOCUMENTS

| | | |
|---|---|---|
| CN | 101889015 A | 11/2010 |
| CN | 103124496 A | 5/2013 |
| CN | 201310485200.6 | 10/2013 |
| CN | 104557872 A | 4/2015 |
| EP | 3059238 A1 | 8/2016 |
| HK | 1209738 A1 | 4/2016 |
| JP | 2003-525295 A | 8/2003 |
| JP | 2008-521905 A | 6/2008 |
| JP | 2010-540625 A | 12/2010 |
| JP | 2012-508236 A | 4/2012 |
| JP | 2013-529212 A | 7/2013 |
| JP | 2016-533372 A | 10/2016 |
| KR | 2016-0062170 | 6/2016 |
| SG | 11201602446V | 5/2016 |
| TW | 201518288 A | 5/2015 |
| WO | 0164679 A1 | 9/2001 |
| WO | 2006060390 A1 | 6/2006 |
| WO | 2007044729 A2 | 4/2007 |
| WO | 2007072163 A2 | 6/2007 |
| WO | 2007127183 A1 | 11/2007 |
| WO | 2007129161 A2 | 11/2007 |
| WO | 2008064093 A2 | 5/2008 |
| WO | 2008127594 A2 | 10/2008 |
| WO | 2008152387 A1 | 12/2008 |
| WO | 2009045174 A1 | 4/2009 |
| WO | 2009045175 A1 | 4/2009 |
| WO | 2009147187 A1 | 12/2009 |
| WO | 2009147190 A1 | 12/2009 |
| WO | 2010056320 A2 | 5/2010 |
| WO | 2010091808 A1 | 8/2010 |
| WO | 2010/114484 A1 | 10/2010 |
| WO | 2010/114494 A1 | 10/2010 |
| WO | 2010120987 A1 | 10/2010 |
| WO | 2010120994 A1 | 10/2010 |
| WO | 2011041399 A2 | 4/2011 |
| WO | 2011101429 A1 | 8/2011 |
| WO | 2011146594 A2 | 11/2011 |
| WO | 2012007493 A1 | 1/2012 |
| WO | 2012032065 A1 | 3/2012 |
| WO | 2012032067 A1 | 3/2012 |
| WO | 2012037226 A1 | 3/2012 |
| WO | 2012040634 A1 | 3/2012 |
| WO | 2012047538 A1 | 4/2012 |
| WO | 2012135160 A1 | 10/2012 |
| WO | 2012136622 A1 | 10/2012 |
| WO | 2013111106 A1 | 8/2013 |
| WO | 2013152717 A1 | 10/2013 |

OTHER PUBLICATIONS

Dec. 31, 2014 International Search Report issued in International Patent Application No. PCT/CN2014/086914.
Dec. 31, 2014 Written Opinion of the International Searching Authority issued in International Patent Application No. PCT/CN2014/086914.
Apr. 7, 2015 Taiwan Office Action issued in TW103135613.
Bart Vanhaesebroeck et al., "Phosphoinositide 3-kinases: A conserved family of signal transducers", Trends Biochem. Sci., vol. 22, pp. 267-272, 1997.
Igor Vivanco et al., "The phosphatidylinositol 3-Kinase—AKT pathway in human cancer",Nat.Rev.Cancer.,vol. 2, pp. 489-501, 2002.
Jessica Raushel et al., "Reinvestigation of Aminomethyltrifluoroborates and Their Application in Suzuki-Miyaura Cross-Coupling Reactions", The Journal of Organic Chemistry,vol. 76, pp. 2762-2769, 2011.
May 25, 2016 Canada Office Action issued in CA2926596.
English Abstract of TW201518288, Publication Date: May 16, 2015.
English Abstract of CN104557872, Publication Date: Apr. 23, 2015.

(56) References Cited

OTHER PUBLICATIONS

English Abstract of HK1209738, Publication Date: Apr. 8, 2016.
English Translation of KR20160062170, Publication Date: Jun. 1, 2016.
English Translation of CN201310485200.6.
English Abstract of SG11201602446, Publication Date: May 30, 2016.
International Search Report for PCT/CN2014/086914 dated Dec. 31, 2004.
R. K. Goel et al., "Quinazolines revisited: search for novel anxiolytic and GABAergic agents", Bioorganic & Medicinal Chemistry Letters 15 (2005) 2145-2148.
Brigitte Charpiot et al., "Quinazolines: Combined Type 3 and 4 Phosphodiesterase Inhibitors", Bioorganic & Medicinal Chemistry Letters 8 (1998) 2891-2896.
Vipan Kumar et al.,"A catalyst- and solvent-free selective approach to biologically important quinazolines and benzo[g] quinazoline", Tetrahedron 61 (2005) 3533-3538.
Aug. 31, 2016 1st Office Action issued in CN104557872A.
Sep. 27, 2016 1st Office Action issued in JP2016-533372A.
English Translation of Aug. 31, 2016 1st Office Action issued in CN104557872A.
English translation of Sep. 27, 2016 1st Office Action issued in JP2016-533372A.
Supplemental Partial European Search Report—dated Dec. 7, 2016 corresponding to EP Application No. 14 85 3907.
Bedi Preet M S et al: "Synthesis and biological activity of novel antibacterial quinazolines", Bioorganic & Medicinal Chemistry Letters, vol. 14, No. 20, Aug. 14, 2004, pp. 5211-5213, XP029246104.
Supplementary European Search Report corresponding to EP 14 85 3907 dated Mar. 15, 2017.

\* cited by examiner

FUSED HETEROCYCLIC COMPOUND, PREPARATION METHOD THEREFOR, PHARMACEUTICAL COMPOSITION, AND USES THEREOF

The application claims priority to CN Patent Application CN20131048520.6 filed on Oct. 16, 2013, which is hereby incorporated herein by reference in its entirety.

FIELD OF THE INVENTION

The present invention especially relates to a fused heterocyclic compound, preparation method therefor, pharmaceutical composition, and uses thereof.

PRIOR ARTS

Phosphatidylinositol 3-kinase (PI3K) is a type of intracellular phosphatidylinositol kinase that can catalyze the phosphorylation of the 3-hydroxy of phosphatidylinositol. The PI3K can be divided into type I kinase, type II kinase, and type III kinase, and the most extensively investigated one is the type I PI3Ks that can be activated by cell surface receptors. Type I PI3Ks in mammalian cells are further divided into two groups based on their structures and receptors, class Ia and class Ib, which transmits signals from tyrosine kinase-coupled receptors and G protein-coupled receptors, respectively. Class Ia PI3Ks include PI3Kα, PI3Kβ and PI3Kδ, class Ib PI3Ks include PI3Kγ (*Trends Biochem. Sci.*, 1997, 22, 267-272). Class Ia PI3Ks are dimers of a catalytic subunit, p110, and a regulatory subunit, p85, having dual activity of lipid kinases and protein kinases (*Nat. Rev. Cancer* 2002, 2, 489-501), which are considered to be related to the cell proliferation, developing of cancers, immunological diseases and inflammation-relating diseases.

Existing technologies have disclosed a number of compounds as PI3K inhibitors, such as: WO2008064093, WO2007044729, WO2008127594, WO2007127183, WO2007129161, US20040266780, WO2007072163, WO2009147187, WO2009147190, WO2010120987, WO2010120994, WO2010091808, WO2011101429, WO2011041399, WO2012040634, WO2012037226, WO2012032065, WO2012007493, WO2012135160 etc.

So far there is no small molecular PI3K inhibitor in market. Therefore, it is urgent to develop an efficient medicament of the PI3Kδ inhibitor with selectivity for treating cancers, infection, inflammation and cell proliferation diseases such as autoimmune diseases.

CONTENT OF THE PRESENT INVENTION

The problem to be solved by the present invention is to provide a fused heterocyclic compound, preparation method therefor, pharmaceutical composition, and uses thereof which is totally different from the prior art. The fused heterocyclic compound of the invention as an inhibitor with selectivity against PI3Kδ can be used to prepare a medicament for treating cancers, infection, inflammation or cell proliferation diseases such as autoimmune diseases.

The present invention provides a fused heterocyclic compound represented by formula I, formula II or formula III, pharmaceutically acceptable salt, hydrate, solvate, polymorph or pro-drug thereof,

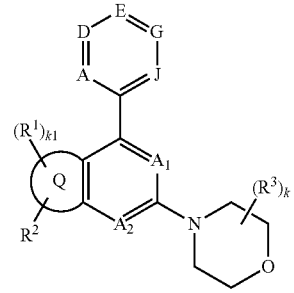

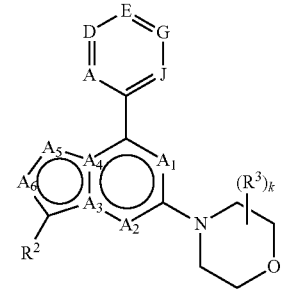

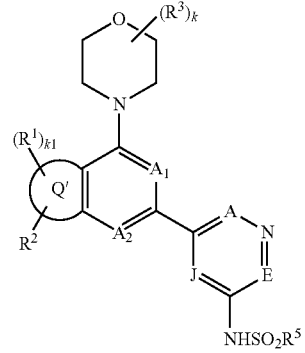

Wherein,
$A_1$ is N or CH;
$A_2$ is N or CH;
$A_3$ is N or C;
$A_4$ is N or C;
$A_5$ is O, S, N, $CR^{1a}$ or $NR^{5a}$;
$A_6$ is O, S, N, $CR^{1b}$ or $NR^{5b}$;
When $A_5$ is O or S, $A_6$ is N;
When $A_6$ is O or S, $A_5$ is N;
$R^{1a}$ and $R^{1b}$ are each independently a hydrogen, a deuterium, a halogen, an alkyl, an alkoxy, an alkenyl, an alkynyl, a cycloalkyl, a heterocycloalkyl or CN;
$R^2$ is $-(CR^8R^9)_mNR^5R^6$, $-(CR^8R^9)_mNR^7C(=Y)R^5$, $-(CR^8R^9)_mNR^7S(O)_2R^5$, $-(CR^8R^9)_mOR^5$, $-(CR^8R^9)_mS(O)_2R^5$, $-(CR^8R^9)_mS(O)_2NR^5R^6$, $-C(OR^5)R^6R^8$, $-C(=Y)R^5$, $-C(=Y)OR^5$, $-C(=Y)NR^5R^6$, $-C(=Y)NR^7OR^5$, $-C(=O)NR^7S(O)_2R^5$, $-C(=O)NR^7(CR^8R^9)_mNR^5R^6$, $-NR^7C(=Y)R^6$, $-NR^7C(=Y)OR^6$, $-NR^7C(=Y)NR^5R^6$, $-NR^7S(O)_2R^5$, $-NR^7S(O)_2NR^5R^6$, $-SR^5$, $-S(O)_2R^5$, $-S(O)_2NR^5R^6$, $-SC(=Y)R^5$, $-SC(=Y)OR^5$, $-O(CR^8R^9)_mCR^5R^6$, $-O(CR^8R^9)_mNR^5R^6$, a $C_{1-12}$ alkyl, a $C_{2-8}$ alkenyl, a $C_{2-8}$ alkynyl, a $C_{3-12}$ carbocyclic group, a $C_{2-20}$ heterocyclic group, a $C_{6-20}$ aryl or a $C_{1-20}$ heteroaryl;

$(R^3)_k$ represents that the hydrogens attached to the morpholine ring are substituted by 0-k occurrences of $R^3$, at each occurrence the $R^3$ is the same or different from each other, and is independently a hydrogen, a deuterium, a halogen, a $C_{1-6}$ alkyl, or any two of the $R^3$ are linked by a single bond, a $C_{1-6}$ alkylene or a $C_{1-6}$ alkylene substituted by one or two heteroatoms to form a ring structure, the heteroatom is O, N, or S;

A is N or $CR^{4a}$;
D is N or $CR^{4d}$;
E is N or $CR^{4e}$;
G is N or $CR^{4g}$;
J is N or $CR^{4j}$;

A, D, E, G and J are not N at the same time;

$R^{4a}$, $R^{4d}$, $R^{4e}$, $R^{4g}$ and $R^{4j}$ are each independently a hydrogen, a halogen, —CN, an alkyl, an alkoxy, an alkenyl, an alkynyl, a cycloalkyl, a heterocycloalkyl, —$NR^5R^6$, —$OR^5$, —$SR^5$, —$C(O)R^5$, —$NR^5C(O)R^6$, —$N(C(O)R^6)_2$, —$NR^5C(O)NR^{5'}R^6$, —$NR^7S(O)_2R^5$, —$C(=O)OR^5$ or —$C(=O)NR^5R^6$, or $R^{4j}$ and $R^{4g}$, together with the atoms to which they are attached form a saturated, unsaturated or partially unsaturated 5-membered or 6-membered heterocycle, the 5-membered or 6-membered heterocycle is fused to the 6-membered ring containing A, D, E, G and J;

Ring Q and ring Q' are benzene, a 5- to 9-membered alicyclic ring, a 5- to 9-membered heteroalicyclic ring, or a 5- to 6-membered heterocyclic ring; ring Q is not a thiophene or a furan; $(R^1)_{k1}$ represents that the hydrogens attached to the ring Q or ring Q' are substituted by 0-k1 occurrences of $R^1$, at each occurrence the $R^1$ is the same or different from each other, and is each independently a halogen, —CN, an alkyl, an alkoxy, an alkenyl, an alkynyl, a cycloalkyl, a heterocycloalkyl, —$NR^5R^6$, —$OR^5$, —$SR^5$, —$C(O)R^5$, —$NR^5C(O)R^6$, —$N(C(O)R^6)_2$, —$NR^5C(O)NR^{5'}R^6$, —$NR^7S(O)_2R^5$, —$C(=O)OR^5$ or —$C(=O)NR^5R^6$;

$R^5$, $R^{5'}$, $R^{5a}$, $R^{5b}$, $R^6$, $R^7$ and $R^{7'}$ are each independently a hydrogen, a $C_{1-12}$ alkyl, —$(CH_2)_{2-3}NH_2$, a $C_{2-8}$ alkenyl, a $C_{2-8}$ alkynyl, a $C_{3-12}$ carbocyclic group, a $C_{2-20}$ heterocyclic group, a $C_{6-20}$ aryl or a $C_{1-20}$ heteroaryl, or $R^5$, $R^6$ together with the nitrogen or carbon atoms to which they are directly attached form a heterocyclic ring or a cycloalkyl, or $R^7$, $R^{7'}$ together with the nitrogen atom to which $R^7$ is directly attached form a heterocyclic ring; the heterocyclic ring or the cycloalkyl may be optionally substituted by the substituent selected from the group consisting of: oxo, —$(CH_2)_mOR^7$, —$NR^7R^{7'}$, —$CF_3$, a halogen, —$SO_2R^7$, —$C(=O)R^7$, —$NR^7C(=Y)R^{7'}$, —$NR^7S(O)_2R^{7'}$, —$C(=Y)NR^7R^{7'}$, a $C_{1-12}$ alkyl, a $C_{2-8}$ alkenyl, a $C_{2-8}$ alkynyl, a $C_{3-12}$ carbocyclic group, a $C_{2-20}$ heterocyclic group, a $C_{6-20}$ aryl or a $C_{1-20}$ heteroaryl;

$(CR^8R^9)_m$ represents that 0 to m $(CR^8R^9)$ are linked with each other, $R^8$ and $R^9$ are the substituents attached to the formed carbon chain, wherein each $R^8$ and $R^9$ are the same or different from each other, and are each independently a hydrogen, a deuterium, a halogen, —CN, a hydroxyl, an alkoxy, a $C_{1-12}$ alkyl, a $C_{2-12}$ alkenyl, a $C_{2-12}$ alkynyl, a $C_{3-12}$ cycloalkyl, a $C_{6-12}$ aryl, a 3- to 12-membered heterocycloalkyl or a 5- to 12-membered heteroaryl; or $R^8$, $R^9$ together with the atoms to which they are attached form a saturated or partially unsaturated $C_{3-12}$ carbon ring or $C_{2-20}$ heterocyclic ring;

wherein the alkyl, alkoxy, alkenyl, alkynyl, cycloalkyl, carbocyclic ring, heterocyclic ring, heterocyclylalkyl, aryl, or heterocyclic group can be optionally substituted by the substituent selected from the group consisting of: a halogen, a hydroxyl, —CN, —$CF_3$, —$NO_2$, oxo, $R^5$, —$C(=Y)R^5$, —$C(=Y)OR^5$, —$C(=Y)NR^5R^6$, —$(CR^8R^9)_mNR^5R^6$, —$(CR^8R^9)_mOR^5$, —$NR^5R^6$, —$NR^7C(=Y)R^5$, —$NR^7C(=Y)OR^6$, —$NR^7C(=Y)NR^5R^6$, —$(CR^8R^9)_mNR^7SO_2R^5$, =$NR^7$, $OR^5$, —$OC(=Y)R^5$, —$OC(=Y)OR^5$, —$OC(=Y)NR^5R^6$, —$OS(O)_2(OR^5)$, —$OP(=Y)(OR^5)(OR^6)$, —$OP(OR^5)(OR^6)$, —$SR^5$, —$S(O)R^5$, —$S(O)_2R^5$, —$S(O)_2NR^5R^6$, —$S(O)(OR^5)$, —$S(O)_2(OR^5)$, —$SC(=Y)R^5$, —$SC(=Y)OR^5$, —$SC(=Y)NR^5R^6$, a $C_{1-12}$ alkyl, a $C_{2-8}$ alkenyl, a $C_{2-8}$ alkynyl, a $C_{3-12}$ carbocyclic group, a $C_{2-20}$ heterocyclic group, a $C_{6-20}$ aryl or a $C_{1-20}$ heteroaryl;

Y is O, S or $NR^7$;

m, k or k1 is independently 0, 1, 2, 3, 4, 5 or 6.

In the formula I, $A_1$ is preferably N;
$A_2$ is preferably N;
$R^2$ is preferably —$(CR^8R^9)_mNR^5R^6$, —$O(CR^8R^9)_mCR^5R^6$ or —$O(CR^8R^9)_mNR^5R^6$;
$R^3$ is preferably a hydrogen, a deuterium, a halogen or a $C_{1-3}$ alkyl;
A is preferably $CR^{4a}$; $R^{4a}$ is preferably a hydrogen, a halogen or a $C_{1-3}$ alkyl;
D is preferably N or $CR^{4d}$; $R^{4d}$ is preferably —$NR^7S(O)_2R^5$;
E is preferably $CR^{4e}$; $R^{4e}$ is preferably a hydrogen, a $C_{1-3}$ alkoxy or —$NR^5R^6$;
G is preferably N or $CR^{4g}$; $R^{4g}$ is preferably —$NR^7S(O)_2R^5$;
J is preferably $CR^{4j}$; $R^{4j}$ is preferably a hydrogen, a halogen or a $C_{1-3}$ alkyl;
or, $R^{4j}$ and $R^{4g}$, together with the atoms to which they are attached form a saturated, unsaturated or partially unsaturated 5- to 6-membered heterocyclic ring, the 5- to 6-membered heterocyclic ring is fused to the 6-membered ring containing A, D, E, G and J; the 5-membered heterocyclic ring is preferably a 5-membered nitrogen-containing heterocyclic ring; the 5-membered nitrogen-containing heterocyclic ring is preferably a pyrazole or a pyrrole;

A, D, E, G and J are not N at the same time;

ring Q is preferably a benzene;

$(R^1)_{k1}$ represents that the hydrogens to which attached to the ring Q are substituted by 0-k1 occurrences of $R^1$, at each occurrence the $R^1$ is the same or different from each other, and is each preferably independently a halogen;

$R^5$, $R^6$ and $R^7$ are each preferably independently a hydrogen, —$(CH_2)_{2-3}NH_2$ or a $C_{1-6}$ alkyl, or $R^5$, $R^6$ together with the nitrogen or carbon atoms to which they are directly attached form a heterocyclic ring or a cycloalkyl, the heterocyclic ring or the cycloalkyl may optionally be substituted by the substituent selected from the group consisting of: —$(CH_2)_mOR^7$, —$SO_2R^7$, —$C(=O)R^7$, a $C_{1-3}$ alkyl, a $C_{3-6}$ carbocyclic group and a $C_{2-5}$ heterocyclic group; wherein the heterocyclic ring is preferably a nitrogen-containing or an oxygen-containing 4- to 6-membered heteroalicyclic ring, the cycloalkyl is preferably a 4- to 6-membered cycloalkyl; wherein the nitrogen-containing 6-membered heteroalicyclic ring is preferably a piperidine or a piperazidine, the oxygen-containing 6-membered heteroalicyclic ring is preferably a tetrahydropyran, the oxygen-containing 5-membered heteroalicyclic ring is preferably a tetrahydrofuran, the nitrogen-containing 5-membered heteroalicyclic ring is preferably a tetrahydropyrrole;

$R^8$ is preferably a hydrogen, a deuterium, a halogen or a $C_{1-3}$ alkyl;

$(CR^8R^9)_m$ represents that 0 to m $(CR^8R^9)$ are linked, $R^8$ and $R^9$ are the substituents attached to the formed carbon chain, wherein each $R^8$ and $R^9$ are the same or different from each other, and are each preferably independently a hydrogen, a deuterium, a halogen or a $C_{1-3}$ alkyl;

m, k or k1 is preferably independently 0 or 1.

In the formula I,
more preferably, $A_1$ and $A_2$ are N at the same time;
more preferably, $R^2$ is
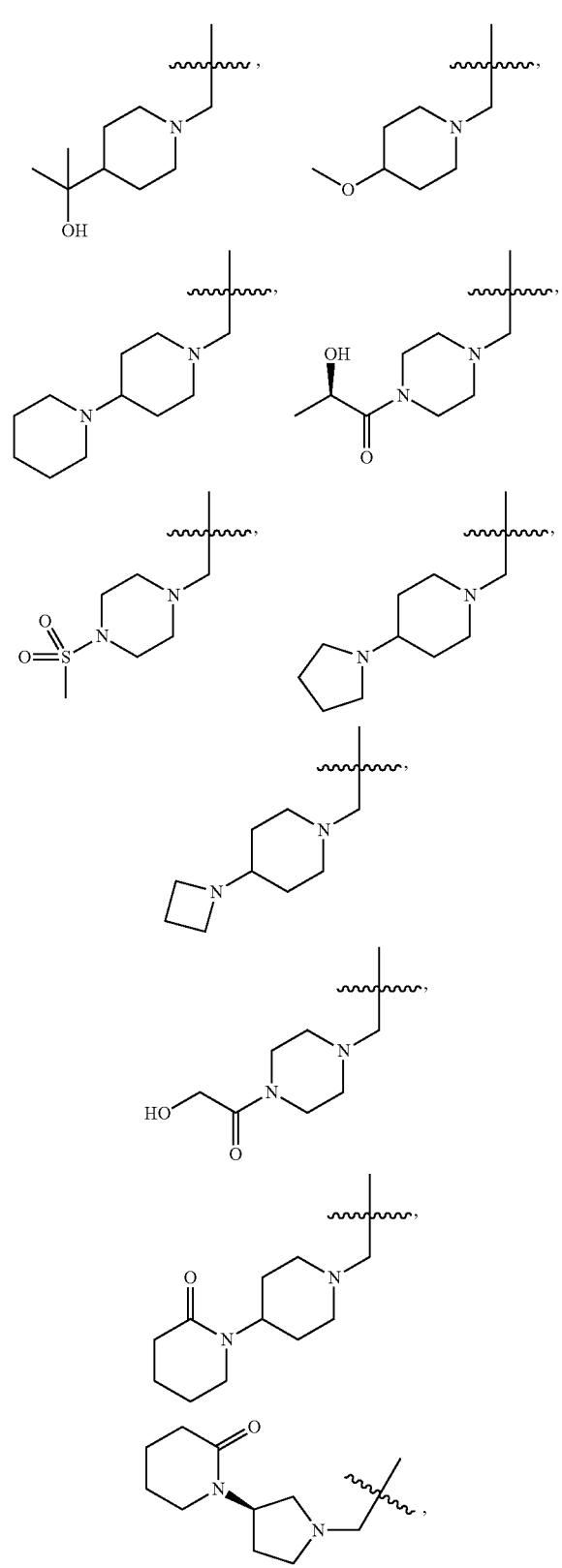
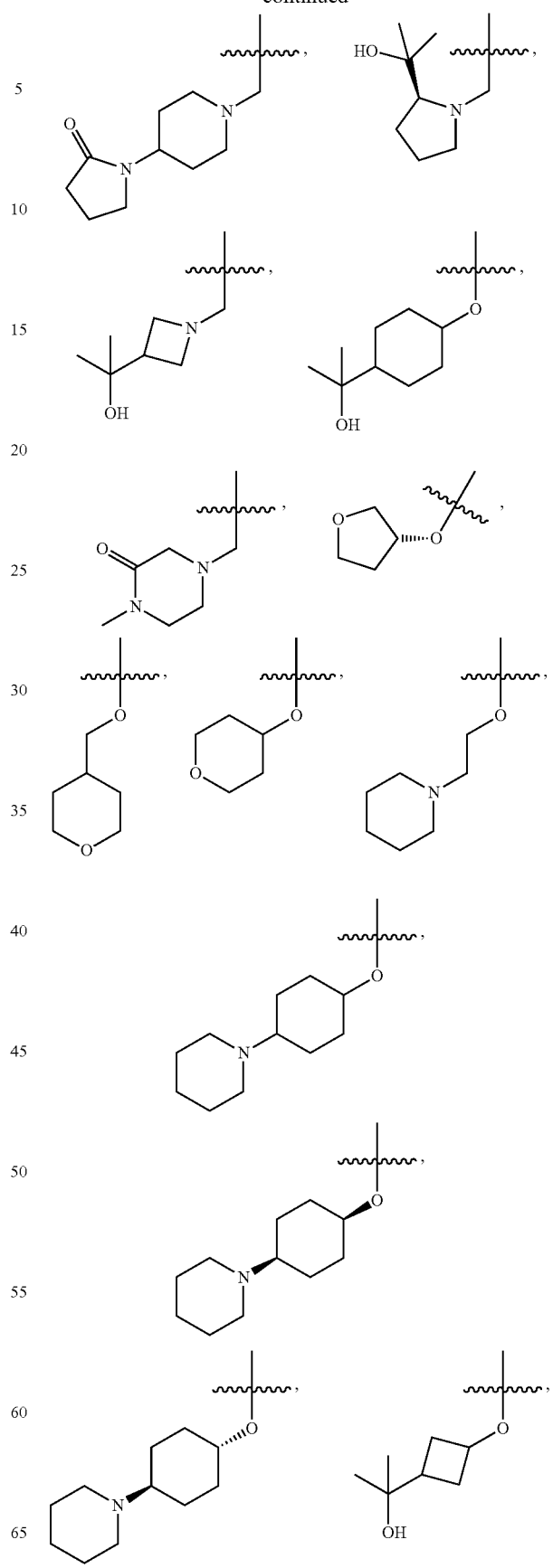

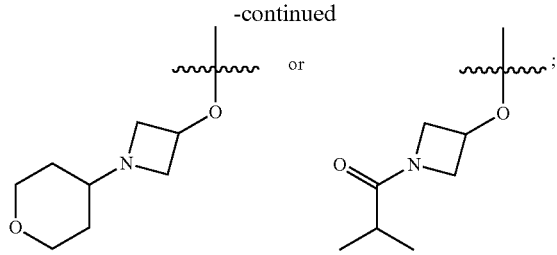

more preferably, $R^3$ is a hydrogen;

more preferably, A is $CR^{4a}$; $R^{4a}$ is more preferably a hydrogen;

more preferably, D is N;

more preferably, E is $CR^{4e}$; $R^{4e}$ is more preferably a hydrogen, a methoxy or $-NH_2$;

more preferably, G is N or $CR^{4g}$; $R^{4g}$ is more preferably

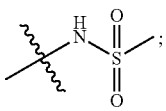 [SMILES: *NS(C)(=O)=O]

more preferably, J is $CR^{4j}$; $R^{4j}$ is more preferably a hydrogen;

or, $R^{4j}$ and $R^{4g}$, together with the atoms to which they are attached form a saturated, unsaturated or partially unsaturated 5- or 6-membered heterocyclic ring, the 5- or 6-membered heterocyclic ring is fused to the 6-membered ring containing A, D, E, G and J; the 5- or 6-membered heterocyclic ring is more preferably a pyrazole or a pyrrole;

A, D, E, G and J are not N at the same time;

Ring Q is more preferably a benzene;

$(R^1)_{k1}$ represents that the hydrogens attached to the ring Q are substituted by 0-k1 occurrences of $R^1$, at each occurrence the $R^1$ is the same or different from each other, and is each more preferably independently fluorine;

more preferably, m, k or k1 is independently 0 or 1.

The formula I is preferably a compound selected from the group consisting of:

1

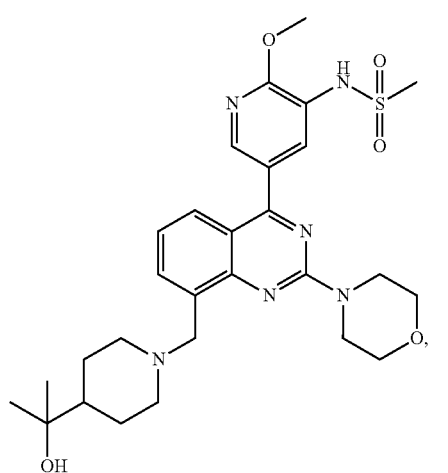

2

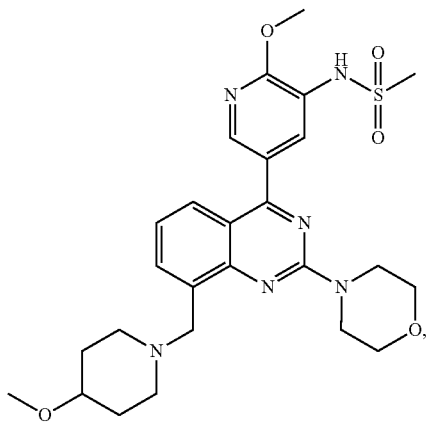

3

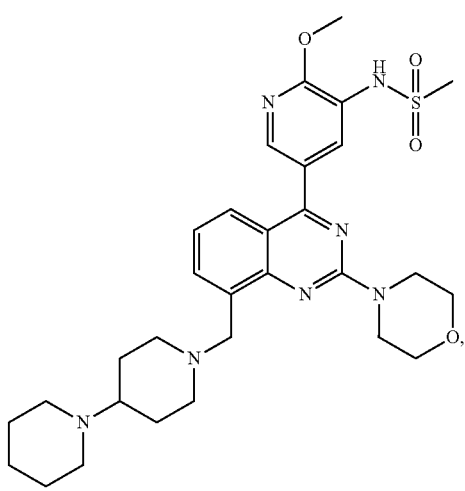

4

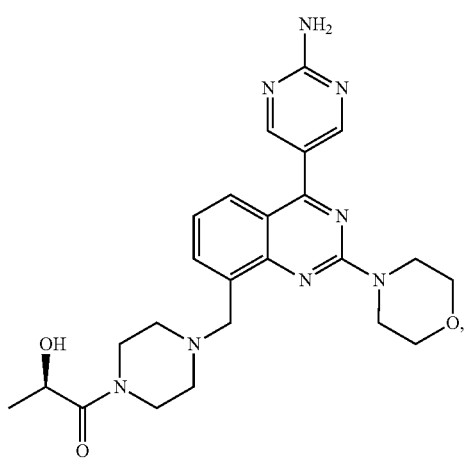

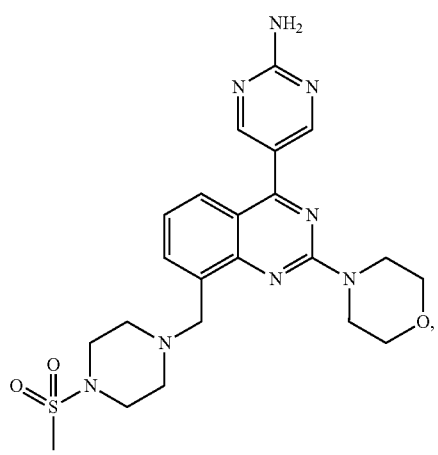
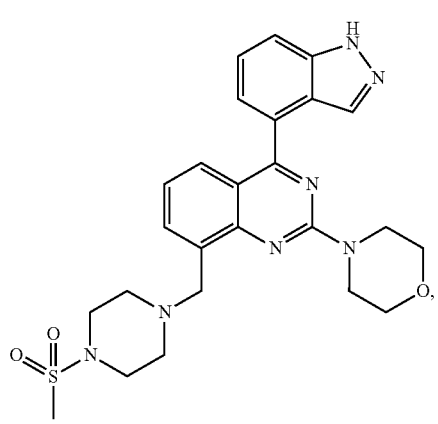
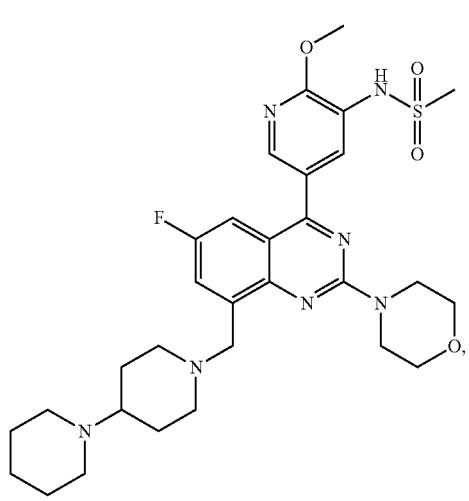
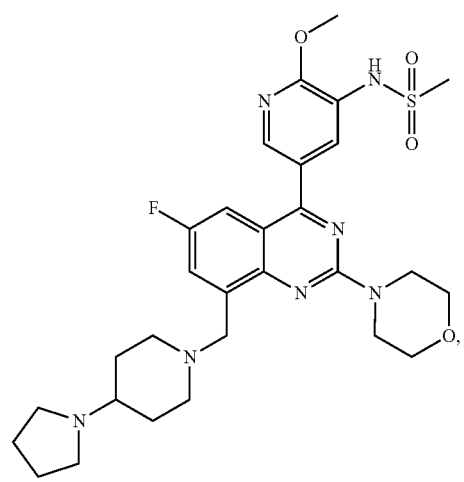
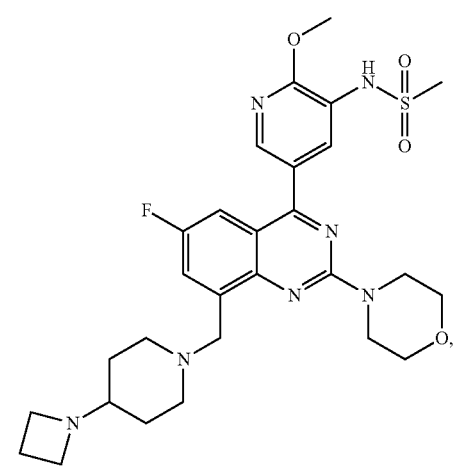
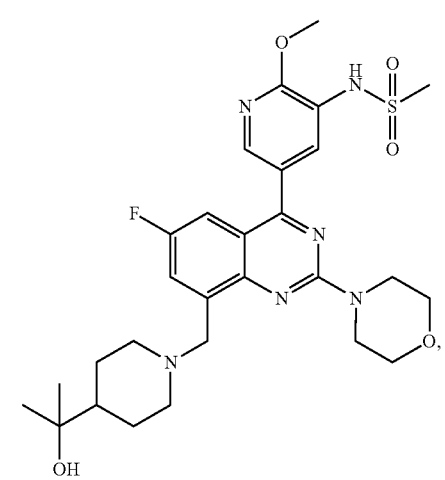

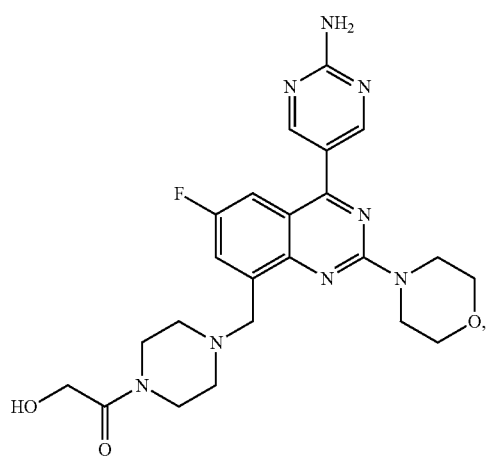
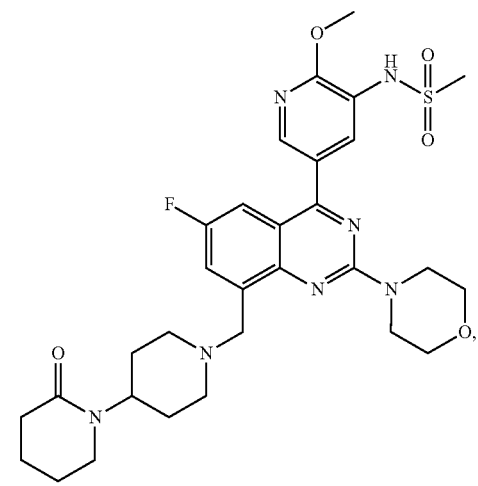
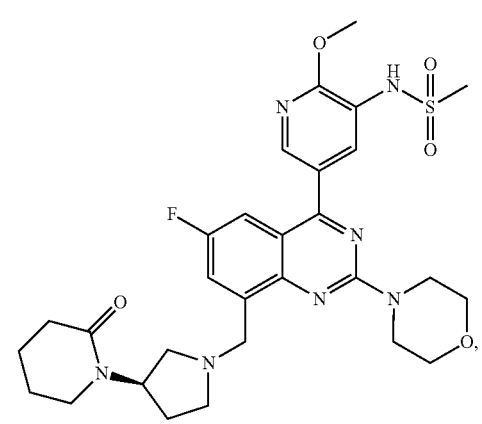
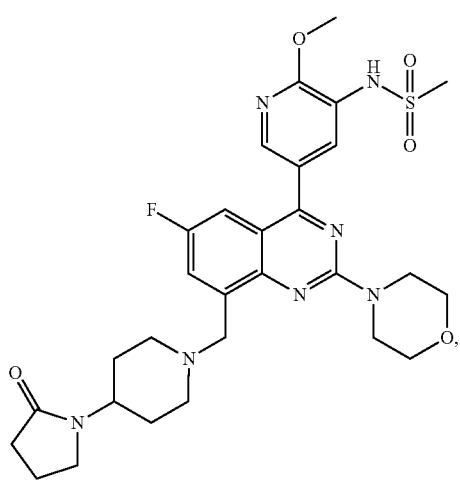
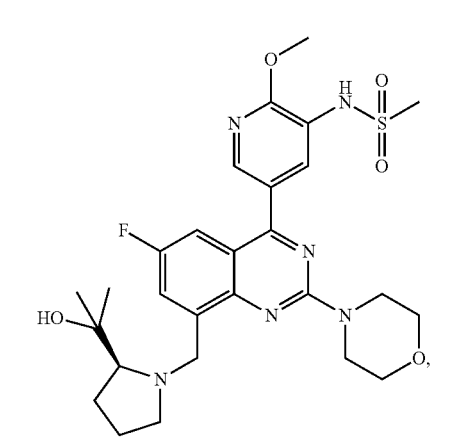
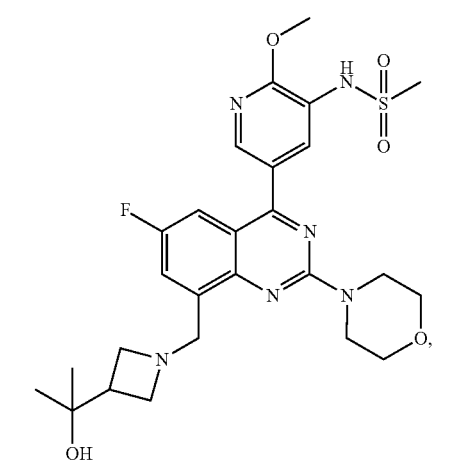

28
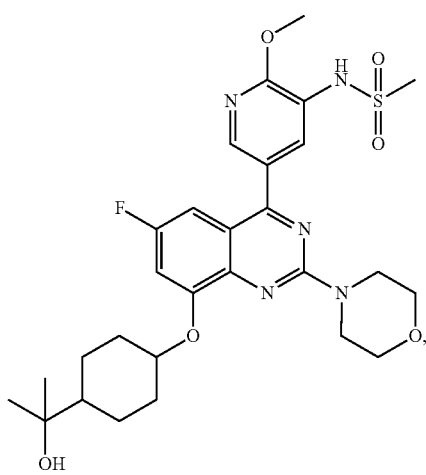
29
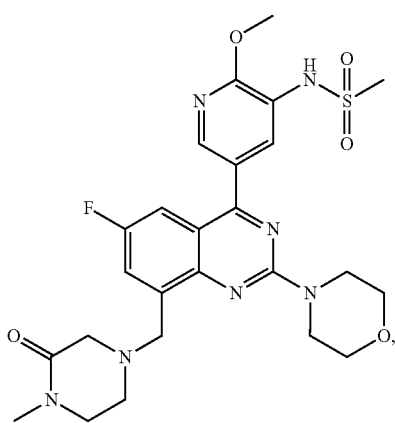
30
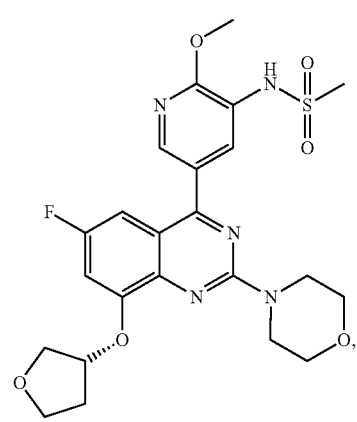
31
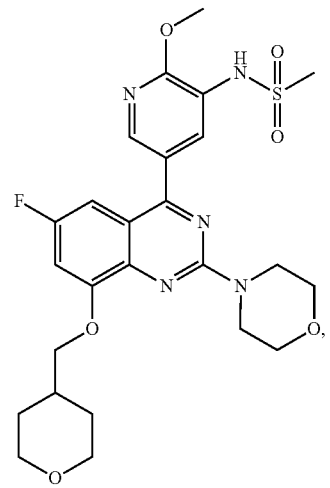
32
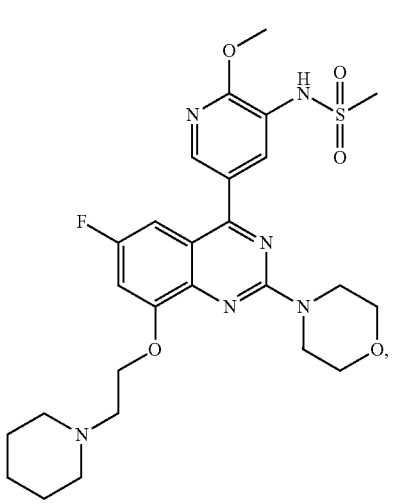
33

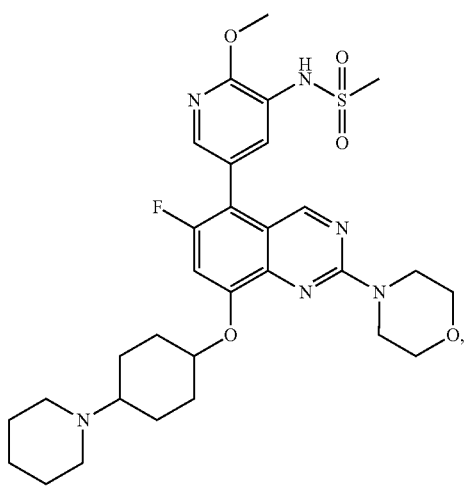
34
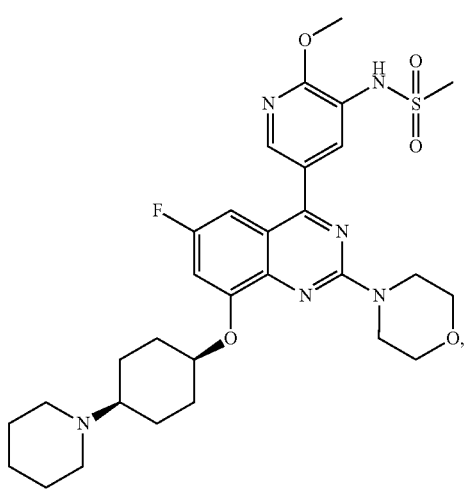
35
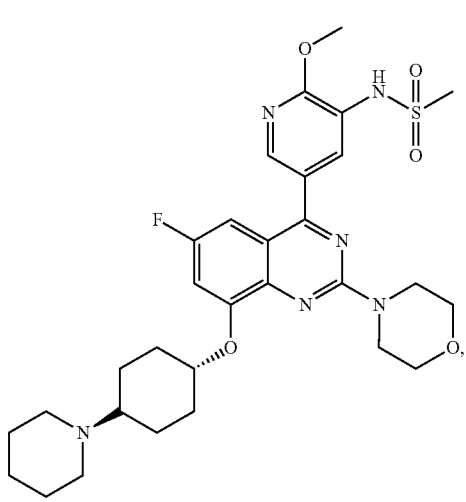
36
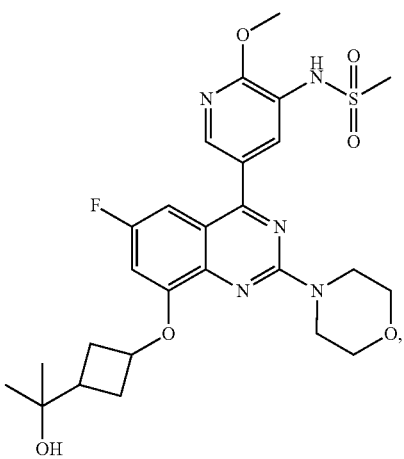
37
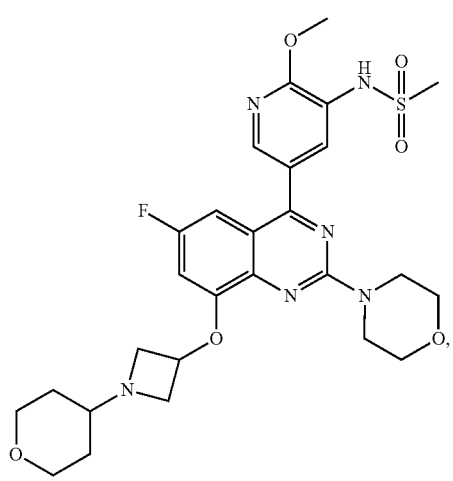
38
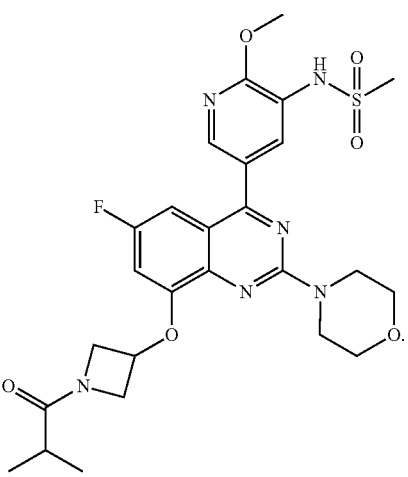
39
In the formula II,
$A_1$ is preferably N or CH;
$A_2$ is preferably N or CH;
$A_3$ is preferably N or C;
$A_4$ is preferably N or C;
$A_5$ is preferably N;
$A_6$ is preferably $CR^{1b}$; $R^{1b}$ is preferably a hydrogen or a deuterium;

$R^2$ is preferably —$(CR^8R^9)_m NR^5R^6$;

$(R^3)_k$ represents that the hydrogens attached to the morpholine ring are substituted by 0-k occurrences of $R^3$, at each occurrence the $R^3$ is the same or different from each other, and is each independently a hydrogen, a deuterium, a halogen, a $C_{1-3}$ alkyl;

A is preferably $CR^{4a}$; $R^{4a}$ is preferably a hydrogen, a halogen or a $C_{1-3}$ alkyl;

D is preferably N or $CR^{4d}$; $R^{4d}$ is preferably a hydrogen, a halogen or a $C_{1-3}$ alkyl;

E is preferably $CR^{4e}$; $R^{4e}$ is preferably a hydrogen, a halogen or a $C_{1-3}$ alkyl;

G is preferably $CR^{4g}$; $R^{4g}$ is preferably —$NR^7S(O)_2R^5$;

J is preferably $CR^4$; $R^{4j}$ is preferably a hydrogen;

or, $R^{4j}$ and $R^{4g}$, together with the atoms to which they are attached form a saturated, unsaturated or partially unsaturated 5-membered heterocyclic ring, the 5-membered heterocyclic ring is fused to the 6-membered ring containing A, D, E, G and J; wherein the 5-membered heterocyclic ring is preferably a 5-membered nitrogen-containing heterocyclic ring; the 5-membered nitrogen-containing heterocyclic ring is preferably a pyrazole or a pyrrole;

$R^5$, $R^6$ and $R^7$ are each preferably independently a hydrogen, a $C_{1-6}$ alkyl, —$(CH_2)_{2-3}NH_2$, a $C_{2-4}$ alkenyl or a $C_{2-4}$ alkynyl, or $R^5$, $R^6$ together with the nitrogen atom to which they are directly attached form a heterocyclic ring which may be optionally substituted by substituent selected from the group consisting of: oxo, —$(CH_2)_m OR^7$, —$CF_3$, a halogen, —$SO_2R^7$, —$C(=O)R^7$, a $C_{1-3}$ alkyl, a $C_{3-6}$ carbocyclic group or a $C_{2-5}$ heterocyclic group; wherein the heterocyclic ring formed by $R^5$, $R^6$ and the nitrogen atom to which they are directly attached is preferably a nitrogen-containing 6-membered heteroalicyclic ring, the nitrogen-containing 6-membered heteroalicyclic ring is preferably a piperidine or a piperazidine;

$(CR^8R^9)_m$ represents that 0 to m $(CR^8R^9)$ are linked, $R^8$ and $R^9$ are the substituents attached to the formed carbon chain, wherein each $R^8$ and $R^9$ are the same or different from each other, and are each preferably independently a hydrogen, a deuterium, a halogen, —CN, a hydroxyl or a $C_{1-3}$ alkyl;

wherein the alkyl, alkenyl, alkynyl, carbocyclic group, heterocyclic ring or heterocyclic group may optionally be substituted by the substituent selected from the group consisting of: a halogen, a hydroxyl, —CN, —$CF_3$, —$NO_2$ or OXO;

m or k is preferably independently 0 or 1.

In the formula II, more preferably, $A_1$, $A_3$ and $A_5$, or, $A_2$, $A_4$ and $A_5$ are N at the same time;

when $A_1$, $A_3$ and $A_5$ are N, $A_2$, $A_4$ and $A_6$ are CH at the same time;

when $A_2$, $A_4$ and $A_5$ are N, $A_1$, $A_3$ and $A_6$ are CH at the same time;

more preferably, $R^2$ is —$(CR^8R^9)_m NR^5R^6$;

$(R^3)_k$ represents that the hydrogens attached to the morpholine ring are substituted by 0-k occurrences of $R^3$, at each occurrence the $R^3$ is the same or different from each other, and is each preferably independently a hydrogen or a deuterium;

A is more preferably $CR^{4a}$; $R^{4a}$ is more preferably a hydrogen;

D is more preferably N or $CR^{4d}$; $R^{4d}$ is more preferably a hydrogen;

E is more preferably $CR^{4e}$; $R^{4e}$ is more preferably a hydrogen;

G is more preferably $CR^{4g}$; $R^{4g}$ is more preferably —$NR^7S(O)_2R^5$;

J is more preferably $CR^{4j}$; $R^{4j}$ is more preferably a hydrogen;

or, $R^{4j}$ and $R^{4g}$, together with the atoms to which they are attached form a saturated, unsaturated or partially unsaturated 5-membered nitrogen-containing heterocyclic ring, the 5-membered nitrogen-containing heterocyclic ring is fused to the 6-membered ring containing A, D, E, G and J; wherein the 5-membered nitrogen-containing heterocyclic ring is more preferably a pyrazole or a pyrrole;

$R^5$, $R^6$ and $R^7$ are each more preferably independently a hydrogen, a $C_{1-3}$ alkyl, —$(CH_2)_2NH_2$, or $R^5$, $R^6$ and the nitrogen atom to which they are directly attached form a heterocyclic ring which may optionally be substituted by the substituent selected from the group consisting of: —$SO_2R^7$ or a $C_{1-3}$ alkyl; wherein the heterocyclic ring formed by $R^5$, $R^6$ and the nitrogen atom to which they are directly attached is more preferably a nitrogen-containing 6-membered heteroalicyclic ring, the nitrogen-containing 6-membered heteroalicyclic ring is preferably a piperidine or a piperazidine;

$(CR^8R^9)_m$ represents that 0 to m $(CR^8R^9)$ are linked, $R^8$ and $R^9$ are the substituents attached to the formed carbon chain, wherein each $R^8$ and $R^9$ are the same or different from each other, and are each preferably independently a hydrogen or a deuterium;

wherein the alkyl, heterocyclic ring or heterocyclic group may optionally be substituted by the substituent selected from the group consisting of: a halogen, a hydroxyl, —CN, —$CF_3$, —$NO_2$ or oxo;

m or k is more preferably independently 0 or 1.

In the formula II, preferably, $A_1$, $A_3$ and $A_5$, or, $A_2$, $A_4$ and $A_5$ are N at the same time;

when $A_1$, $A_3$ and $A_5$ are N, $A_2$, $A_4$ and $A_6$ are CH at the same time;

when $A_2$, $A_4$ and $A_5$ are N, $A_1$, $A_3$ and $A_6$ are CH at the same time;

$R^2$ is

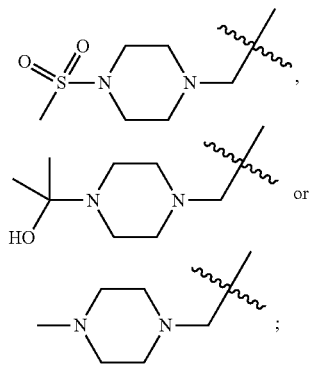

$(R^3)_k$ represents that the hydrogens attached to the morpholine ring are substituted by 0-k occurrences of $R^3$, at each occurrence the $R^3$ is the same or different from each other, and is each independently a hydrogen or a deuterium;

A is $CR^{4a}$; $R^{4a}$ is a hydrogen;

D is N or $CR^{4d}$; $R^{4d}$ is a hydrogen;

E is $CR^{4e}$; $R^{4e}$ is a hydrogen;

G is $CR^{4g}$; $R^{4g}$ is —$NR^7S(O)_2R^5$;

J is $CR^4$; $R^{4j}$ is a hydrogen;

or, $R^{4j}$ and $R^{4g}$, together with the atoms to which they are attached form a saturated, unsaturated or partially unsaturated 5-membered nitrogen-containing heterocyclic ring, the 5-membered nitrogen-containing heterocyclic ring is fused to the 6-membered ring containing A, D, E, G and J; wherein the 5-membered nitrogen-containing heterocyclic ring is a pyrazole or a pyrrole;

$R^5$ and $R^7$ are each independently a hydrogen or a $C_{1-3}$ alkyl;

$(CR^8R^9)_m$ represents that 0 to m $(CR^8R^9)$ are linked, $R^8$ and $R^9$ are the substituents attached to the formed carbon chain, wherein each $R^8$ and $R^9$ are the same or different from each other, and are each independently a hydrogen or a deuterium;

wherein the alkyl is substituted by a hydroxyl;

m or k is independently 0 or 1.

The formula II is a compound selected from the group consisting of:

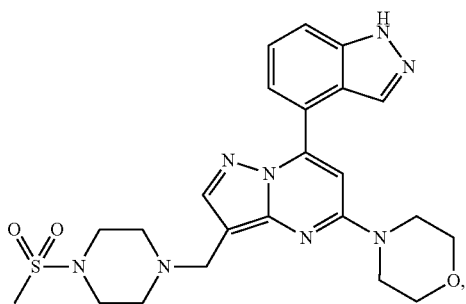

11

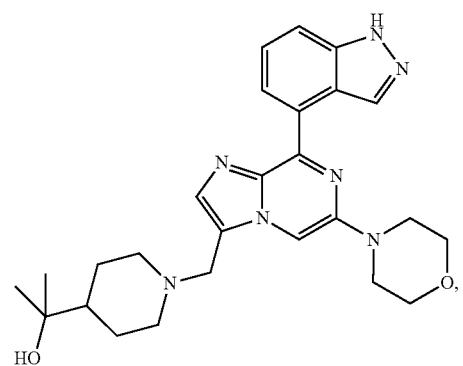

12

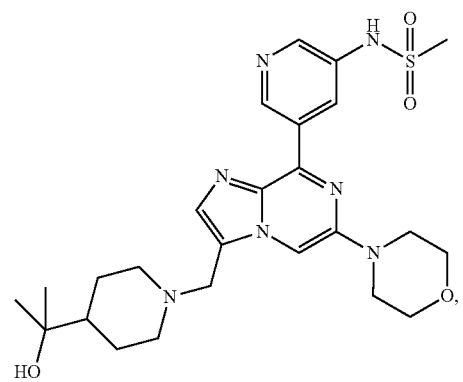

13

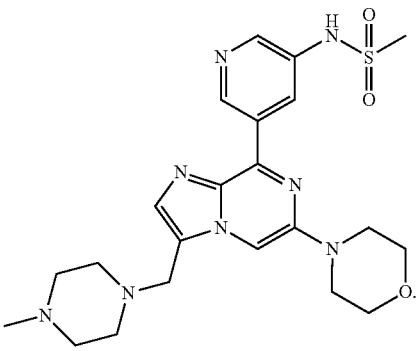

14

In the formula III, $A_1$ is preferably N;

$A_2$ is preferably N;

$R^2$ is preferably —$(CR^8R^9)_mNR^5R^6$ or —$(CR^8R^9)_mOR^5$;

$(R^3)_k$ represents that the hydrogens attached to the morpholine ring are substituted by 0-k occurrences of $R^3$, at each occurrence the $R^3$ is the same or different from each other, and is each preferably independently a hydrogen, a deuterium, a halogen or a $C_{1-3}$ alkyl;

A is preferably $CR^{4a}$; $R^{4a}$ is preferably a hydrogen, a halogen or a $C_{1-3}$ alkyl;

E is preferably $CR^{4e}$; $R^{4e}$ is preferably a $C_{1-6}$ alkoxy;

J is preferably $CR^4$; $R^{4j}$ is preferably a hydrogen;

ring Q' is preferably a benzene or a 5-membered heterocyclic ring; $(R^1)_{k1}$ represents that the hydrogens attached to the ring Q' are substituted by 0-k1 occurrences of $R^1$, at each occurrence the $R^1$ is the same or different from each other, and is each preferably independently a halogen, —CN or a $C_{1-12}$ alkyl;

$R^5$, $R^6$, $R^7$ and $R^{7'}$ are each preferably independently a hydrogen, a $C_{1-6}$ alkyl, —$(CH_2)_{2-3}NH_2$, a $C_{3-6}$ carbocyclic group or a $C_{2-5}$ heterocyclic group, or $R^5$, $R^6$ and the nitrogen atom to which they are directly attached form a heterocyclic ring which may optionally be substituted by the substituent selected from the group consisting of: —$NR^7R^{7'}$, a $C_{1-3}$ alkyl, a $C_{3-6}$ carbocyclic group or a $C_{2-5}$ heterocyclic group;

$(CR^8R^9)_m$ represents that 0 to m $(CR^8R^9)$ are linked, $R^8$ and $R^9$ are the substituents attached to the formed carbon chain, wherein each $R^8$ and $R^9$ are the same or different from each other, and are each independently preferably a hydrogen, a deuterium or a $C_{1-3}$ alkyl;

m, k or k1 is preferably independently 0 or 1.

In the formula III, $A_1$ is more preferably N;

$A_2$ is more preferably N;

$R^2$ is more preferably —$(CR^8R^9)_mNR^5R^6$ or —$(CR^8R^9)_mOR^5$;

$(R^3)_k$ represents that the hydrogens attached to the morpholine ring are substituted by 0-k occurrences of $R^3$, at each occurrence the $R^3$ is the same or different from each other, and is each more preferably independently a hydrogen or a deuterium;

A is more preferably $CR^{4a}$; $R^{4a}$ is more preferably a hydrogen;

E is more preferably $CR^{4e}$; $R^{4e}$ is more preferably a $C_{1-3}$ alkoxy;

J is more preferably $CR^4$; $R^{4j}$ is more preferably a hydrogen;

ring Q' is more preferably a benzene or a 5-membered heterocyclic ring, the 5-membered heterocyclic ring is preferably a thiophene or an imidazole;

$(R^1)_{k1}$ represents that the hydrogens attached to the ring Q' are substituted by 0-k1 occurrences of $R^1$, at each occurrence the $R^1$ is the same or different from each other, and is each more preferably independently a $C_{1-3}$ alkyl;

$R^5$, $R^6$, $R^7$ and $R^{7'}$ are each more preferably independently a hydrogen, a $C_{1-3}$ alkyl, $-(CH_2)_{2-3}NH_2$, a $C_{3-6}$ carbocyclic group or a $C_{2-5}$ heterocyclic group, or $R^5$, $R^6$ and the nitrogen atom to which they are directly attached form a heterocyclic ring which may optionally be substituted by the substituent selected from the group consisting of: $-NR^7R^{7'}$, a $C_{1-3}$ alkyl, a $C_{3-6}$ carbocyclic group or a $C_{2-5}$ heterocyclic group; the $C_{2-5}$ heterocyclic group is preferably a piperidine, a pyran, a tetrahydropyrrole or an oxetane;

$(CR^8R^9)_m$ represents that 0 to m $(CR^8R^9)$ are linked, $R^8$ and $R^9$ are the substituents attached to the formed carbon chain, wherein each $R^8$ and $R^9$ are the same or different from each other, and are each more preferably independently a hydrogen or a deuterium;

m, k or k1 is preferably independently 0 or 1.

In the formula III, preferably, $A_1$ is N;

$A_2$ is N;

$R^2$ is

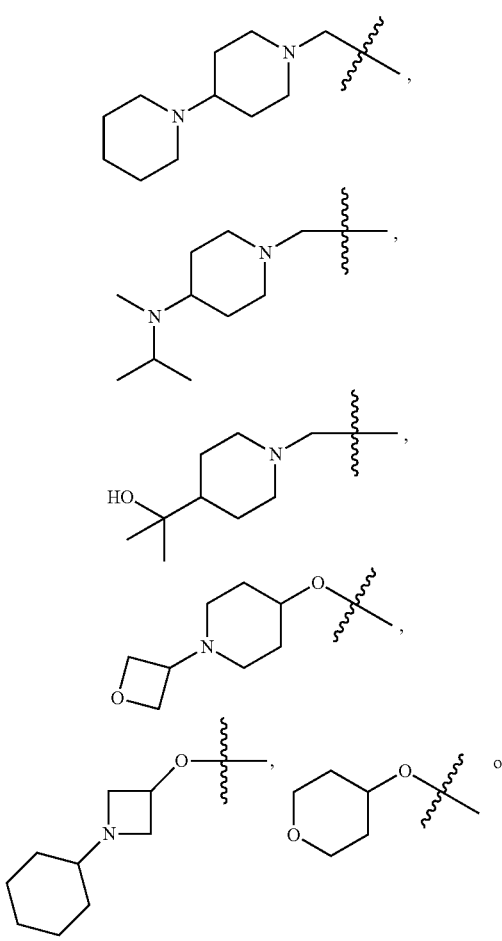

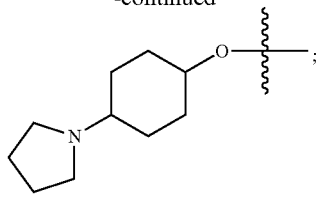

$(R^3)_k$ represents that the hydrogens attached to the morpholine ring are substituted by 0-k occurrences of $R^3$, at each occurrence the $R^3$ is the same or different from each other, and is each independently a hydrogen or a deuterium;

A is $CR^{4a}$; $R^{4a}$ is a hydrogen;

E is $CR^{4e}$; $R^{4e}$ is a methoxy;

J is $CR^{4j}$; $R^{4j}$ is a hydrogen;

ring Q' is a benzene or a 5-membered heterocyclic ring, the 5-membered heterocyclic ring is a thiophene or an imidazole; $(R^1)_{k1}$ represents that the hydrogens attached to the ring Q' are substituted by 0-k1 occurrences of $R^1$, at each occurrence the $R^1$ is the same or different from each other, and is each independently a methyl;

m, k or k1 is independently 0 or 1.

The formula III is more preferably a compound selected from the group consisting of:

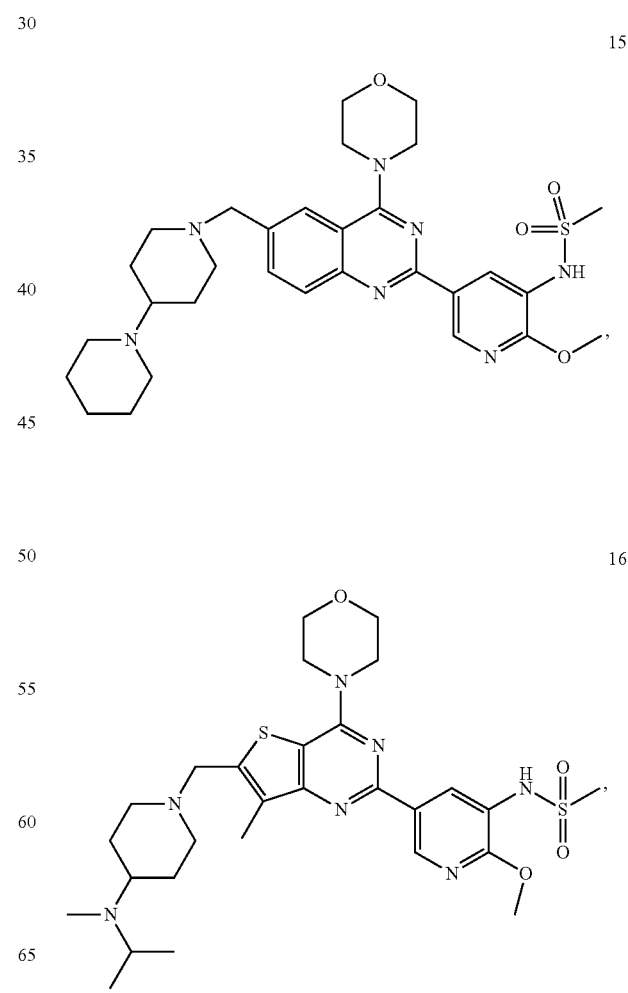

23
-continued

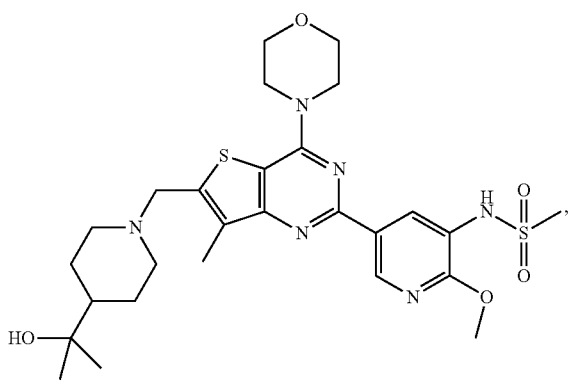

17

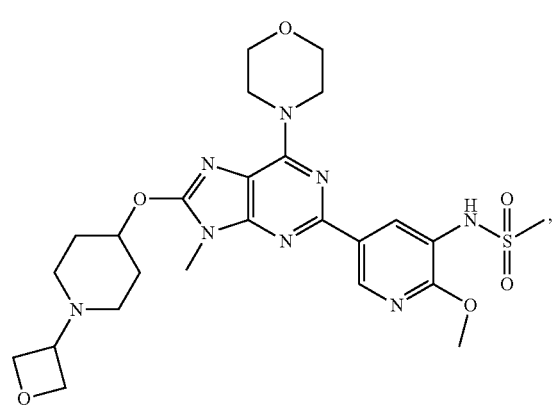

18

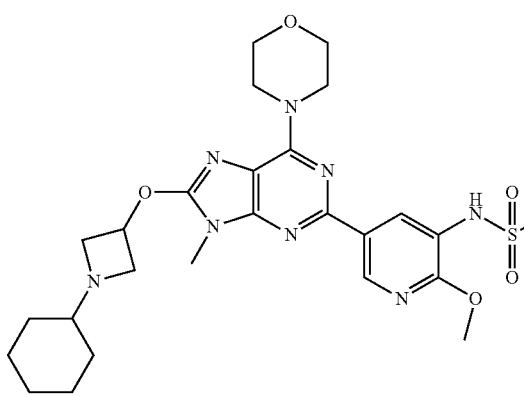

19

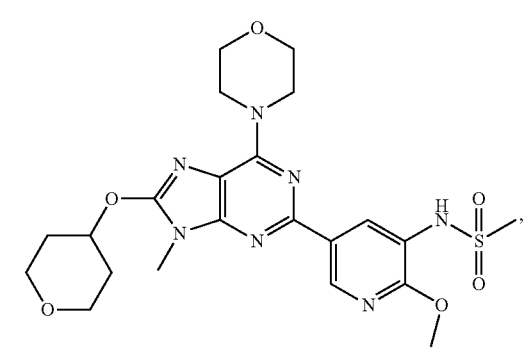

20

24
-continued

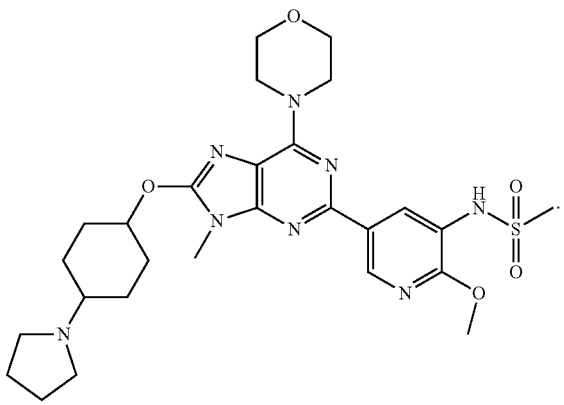

21

The present invention also provides a process for preparing the fused heterocyclic compound, pharmaceutically acceptable salt, hydrate, solvate, polymorph or pro-drug thereof, which may use commercially available raw materials, known methods in the art in combination with the contents disclosed in the present invention. Specific routes are as following:

Reaction route I comprises the following steps:

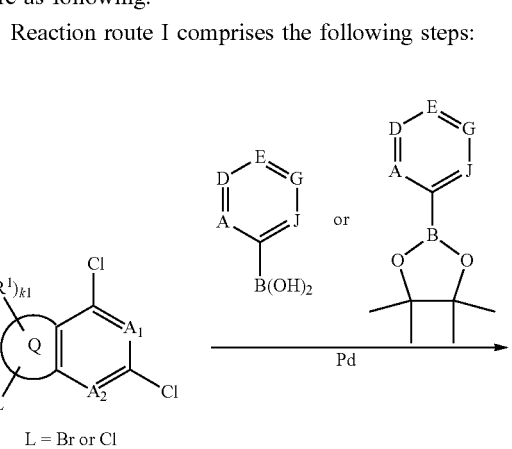

-continued
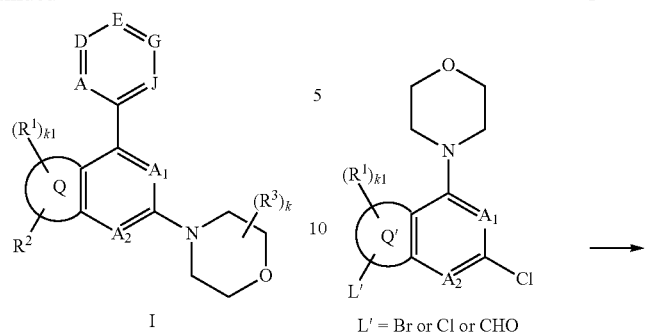
I
Reaction route II comprises the following steps:
Reaction route III comprises the following steps:
Reaction route IV comprises the following steps:
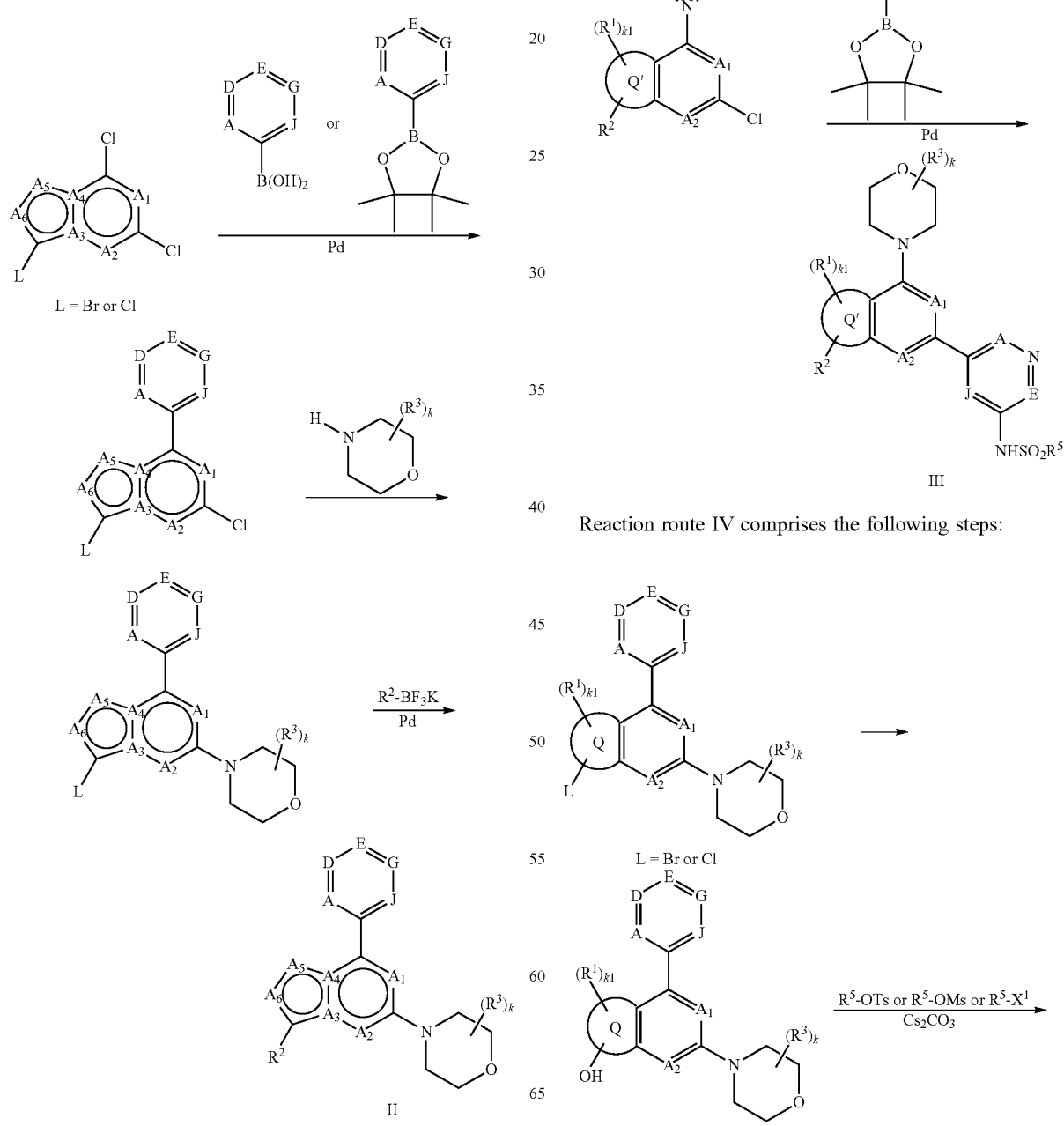

-continued

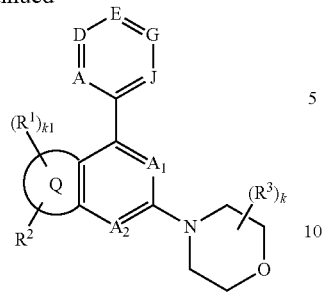

wherein the substituents are each defined as above, and when R is —O(CR⁸R⁹)ₘCR⁵R⁶ or —O(CR⁸R⁹)ₘNR⁵R⁶ in the formula I, the reaction route IV is utilized to synthesis. When R² is not —O(CR⁸R⁹)ₘCR⁵R⁶ or —O(CR⁸R⁹)ₘNR⁵R⁶ in the formula I, the reaction route I is utilized to synthesis; X¹ is Cl, Br or I.

The conditions and steps utilized in the chemical reactions involved in the four reaction routes above can all be performed by reference to those commonly used in the art, and particularly can refer to the following references: J. Org. Chem. 2011, 76, 2762-2769; R. Larock, Comprehensive Organic Transformations, VCH Publishers (1989); T. W. Greene and P. G. M. Wuts, Protective Groups in Organic Synthesis, 3ʳᵈ ED., John Wiley and Sons (1999); L. Fieser and M. Fieser, Fieser and Fieser's Reagents for Organic Synthesis, John Wiley and Sons (1994); and L. Paquette (edit), Encyclopedia of Reagents for Organic Synthesis, John Wiley and Sons (1995) and its subsequent editions. In addition, the compounds obtained according to the methods above can be further modified in peripheral positions to give other target compounds of the present invention according to the relevant methods disclosed in the above references.

The present invention also provides a compound represented by the structure selected from the group consisting of:

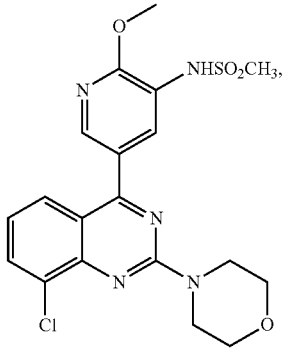

1-a

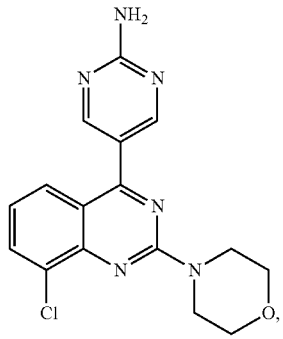

4-d

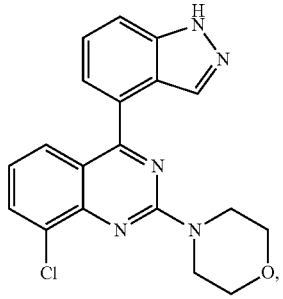

6-a

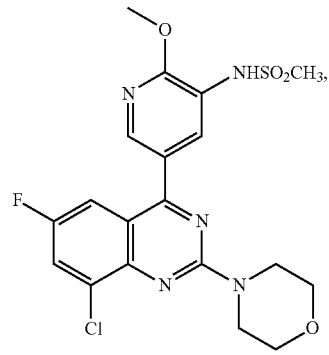

7-a

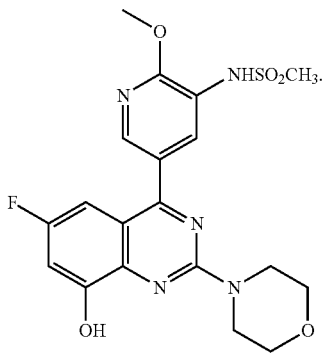

28-b

At least one of the fused heterocyclic compound, pharmaceutically acceptable salt, hydrate, solvate, polymorph or pro-drug thereof prepared by the above routes can be purified by column chromatograph, HPLC, crystallization or other proper conditions.

The conditions and steps used in the purification method such as column chromatograph, HPLC and crystallization can refer to conventional conditions and steps in the art.

The above fused heterocyclic compound provided in the present invention can exhibit tautomerism, structural isomerism and stereoisomerism. The present invention includes any tautomer, structural isomer or stereo isomer of the compound and their mixtures, they have the ability of regulating the activity of the kinase and this ability is not limited to any isomer or the form of its mixture.

The present invention also provides a use of the fused heterocyclic compound represented by formula I, formula II or formula III, pharmaceutically acceptable salt, hydrate, solvate, polymorph or pro-drug thereof in manufacturing an inhibitor of kinase.

The present invention also provides a use of the fused heterocyclic compound represented by formula I, formula II or formula III, pharmaceutically acceptable salt, hydrate, solvate, polymorph or pro-drug thereof in manufacturing a medicament for treating and/or preventing a disease related to the kinase.

In the present invention, the kinase is preferably PI3 kinase (PI3K), more preferably p110 δ subtype of PI3K (PI3K).

The present invention also provides a pharmaceutical composition, which comprises a therapeutically effective dosage of one or more of the fused heterocyclic compounds represented by formula I, formula II or formula III, pharmaceutically acceptable salt, hydrate, solvate, polymorph and pro-drug thereof, and a pharmaceutically acceptable carrier.

In the present invention, the term "therapeutically effective dosage" means (i) the amount of the compound of the present invention required for preventing or treating the specific disease or disorder described in the application; (ii) the amount of the compound of the present invention required for attenuating, ameliorating or eliminating one or more symptoms of the specific disease or disorder described in the application; or (iii) the amount of the compound of the present invention required for preventing or delaying the onset of one or more symptoms of the specific disease or disorder described in the application. The dosage for treating human patients may range from 0.0001 mg/kg to 50 mg/kg, most typically 0.001 mg/kg to 10 mg/kg body weight, e.g. within the range from 0.01 mg/kg to 1 mg/kg. Such a dosage may be administered, for example 1-5 times a day.

Depending on the purpose of therapy, the pharmaceutical composition can be prepared into a variety of unit dose formulations, such as tablets, pills, powder, liquid, suspensions, emulsions, granules, capsules, suppositories and injections (solutions and suspensions) and so on, and preferably liquids, suspensions, emulsions, suppositories and injections (solutions and suspensions) etc.

In order to make the pharmaceutical composition form a tablet preparation, any known and widely used excipient in the art can be used. For example, carriers (such as lactose, sugar, sodium chloride, glucose, carbamide, starch, calcium carbonate, kaolin, crystalline cellulose and silicic acid etc.), adhesive (such as water, ethanol, propanol, ordinary syrup, glucose solution, starch solution, gelatin solution, carboxymethyl cellulose, lac, methyl cellulose and potassium phosphate, Polyvinylpyrrolidone, etc.), disintegrant (such as dry starch, sodium alginate, agar powder and kelp powder, sodium bicarbonate, calcium carbonate, the polyethylene sorbitan fatty acid ester, sodium dodecyl sulfate, stearic acid monoglyceride, starch and lactose, etc.), disintegration inhibitor (such as sugar, glyceryl tristearate, coconut oil and hydrogenated oil), adsorption accelerant (such as quaternary amine base and sodium dodecyl sulfate, etc.), wetting agent (such as glycerin, starch, etc.), sorbent (such as starch, lactose, kaolin, bentonite and colloid silicic acid, etc.) and lubricant (such as pure talc, stearate, boric acid powder and polyethyleneglycol, etc.). Common coating materials can also be used according to the requirements to form sugar-coated tablets, gelatin-coated tablets, enteric coated tablets, film-coated tablets, double film coated tablets and multiple film coated tablets.

In order to make the pharmaceutical composition form a pill preparation, any known and widely used excipient in the art can be used, for example, carriers (such as lactose, starch, coconut oil, hydrogenated vegetable oil, kaolin and talc powder, etc.), adhesive (such as acacia powder, tragacanth gum powder, gelatin and ethanol, etc.), disintegrant (such as agar and kelp powder, etc.).

In order to make the pharmaceutical composition form a suppository preparation, any known and widely used excipient in the art can be used, for example, polyethyleneglycol, coconut oil, higher alcohols, higher alcohol esters, gelatin and semisynthetic glyceride, etc.

In order to make the pharmaceutical composition form an injection preparation, the solution or suspension (preferably adding a proper amount of sodium chloride, glucose or glycerin, etc.) can be sterilized, and then with which prepare the injection preparation having isosmotic pressure with the blood. In the process for preparing the injection preparation, any commonly used carriers in the art can also be used. For instance, water, ethanol, propanediol, ethoxylated isostearyl alcohol, polyoxy isostearyl alcohol and the polyethylene sorbitan fatty acid ester, etc. Besides, conventional solvents, buffer and analgetic and the like can also be added.

In the present invention, the administration of the pharmaceutical composition do not have special requirements. Various preparation for administration is selected according to the age, gender, other condition and symptoms of patients. For instance, tablets, pills, solutions, suspensions, emulsions, granules or capsules for oral administration; injection preparations can be administered individually, or mixed with an injectable conveying liquid (such as glucose solution and amino acid solution) and transvenously injected; the suppository is administered rectally.

The present invention also provides a use of the pharmaceutical composition in manufacturing a kinase inhibitor.

The present invention also provides a use of the pharmaceutical composition in manufacturing a medicament for treating and/or preventing a disease related to kinase.

The kinase is preferably PI3 kinase.

In the present invention, the "disease related to kinase" includes, but is not limited to, the disease selected from the group consisting of cancer, immunological diseases, metabolic and/or endocrine dysfunction, angiocardiopathy, virus infections and inflammation, and nerve diseases, preferably cancer and/or immunological diseases. The immunological diseases include but are not limited to the disease selected from the group consisting of rheumatoid arthritis, psoriasis, ulcerative colitis, Crohn disease and systemic lupus erythematosus. The angiocardiopathy includes but is not limited to neoplastic hematologic disorder. The virus infections and inflammation include but are not limited to asthma and/or atopic dermatitis.

Unless otherwise indicated, the following terms used in the descriptions and the claims of the present invention have the following meanings:

As used herein, the term "alkyl" (used alone or as a part of other groups) refers to a saturated linear or branched-chain aliphatic hydrocarbyl containing 1 to 20 carbon atoms, preferably 1 to 12 carbon atoms, more preferably 1 to 6 carbon atoms, such as methyl, ethyl, n-propyl, isopropyl, n-butyl, tert-butyl, isobutyl, pentyl, hexyl, heptyl, octyl, nonyl, decyl, 4,4-dimethylpentyl, 2,2,4-trimethylpentyl, undecyl, dodecyl, and the various isomers thereof etc.; as well as the alkyl groups containing 1 to 4 substituents selected from the group consisting of: a deuterium, a halogen (preferred F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, a cycloalkenyl, a cycloalkyl alkyl, a cycloalkyl alkoxy, amino, optionally substituted amino (such as amino substituted by one to two $C_1$-$C_3$ alkyl groups, or —$NR^7C(=Y)R^5$ mentioned above), a hydroxyl, a hydroxylalkyl, an acyl, an aldehyde group, a heteroaryl, a heteroaryloxy, a heterocycloalkyl, a heterocycloalkoxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a $C_{2-20}$ heterocyclic group, a nitro, a cyano, a thiol, a haloalkyl, a trihaloalkyl (such as a trifluoromethyl) and/or an alkylthio. "$C_{x1}$-$C_{y1}$" alkyl (x1 and y1 are integer) described in the present invention with the range of the number of carbon atoms specified, such as "a $C_1$-$C_{12}$ alkyl", except that the range of the number of carbon atoms differs from the range of the number of carbon atoms of "alkyl" defined in this paragraph, has the same definition as the term "alkyl".

As used herein, the term "alkylene" (used alone or as a part of other groups) refers to a subsaturated linear or branched-chain aliphatic hydrocarbyl containing 1 to 20 carbon atoms, preferably 1 to 12 carbon atoms, more preferably 1 to 6 carbon atoms, such as a methylene, an ethylene, a n-propylene, an isopropylene, a n-butylene, a tert-butylene, an isobutylene, a pentylene, a hexylene, a heptylene, an octylene, a nonylene, a decylene, 4,4-dimethylpentylene, 2,2,4-trimethylpentylene, an undecylene, a dodecylene, and the various isomers thereof etc.; as well as the alkylene containing 1 to 4 substituents selected from the group consisting of: a deuterium, a halogen (preferably selected from F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, a cycloalkenyl, a cycloalkyl alkyl, a cycloalkyl alkoxy, an amino, optionally substituted amino (such as amino substituted by one to two $C_1$-$C_3$ alkyl groups), a hydroxyl, a hydroxyalkyl, an acyl, an aldehyde group, a heteroaryl, a heteroaryloxy, a heterocycloalkyl, a heterocycloalkoxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a cyano, a thiol, a haloalkyl, a trihaloalkyl (such as trifluoromethyl), and/or an alkylthio; the substituents selected from the group mentioned above may also form a ring together with the alkylene group, thereby forming a spiro ring or a fused ring.

The term "alicyclic ring", "carbocyclic group" or "cycloalkyl" (used alone or as a part of other groups) includes saturated or partially unsaturated (containing 1 or 2 double bonds) cyclic hydrocarbon groups containing 1 to 3 rings, including monocyclic alkyl, bicyclic alkyl or tricyclic alkyl exhibited in the form of a fused ring or a bridge ring containing 3 to 20 ring-forming carbon atoms, preferably 3 to 12 carbon atoms, for example: cyclopropyl, cyclobutyl, cyclopentyl, cyclohexyl, cycloheptyl, cyclooctyl, cyclodecyl and cyclododecyl, cyclohexenyl; the cycloalkyl may be optionally substituted by 1 to 4 substituents selected from the group consisting of: a deuterium, a halogen, an alkyl, an alkoxy, a hydroxyl, an aryl, an aryloxy, an arylalkyl, a cycloalkyl, an alkylamino, an acylamino, oxo, an acyl, an arylcarbonylamino, an amino, a nitro, a cyano, a thiol and/or an alkylthio and/or any alkyl substituents. In addition, any cycloalkyl ring may be fused to a cycloalkyl, an aryl, a heteroaryl or a heterocycloalkyl ring to form a fused ring, a bridge ring or a spiro ring.

The term "alkoxy" refers to a cyclic or non-cyclic alkyl group containing the indicated number of carbon atoms and having a connection through an oxygen bridge. Thus, "alkoxy" includes the definitions of "alkyl" and "cycloalkyl" mentioned above.

The term "alkenyl" refers to a straight-chain, branched-chain or cyclic non-aromatic hydrocarbyl having the indicated number of carbon atoms and at least one carbon-carbon double bond. Preferably, there is one carbon-carbon double bond, and may have up to four non-aromatic carbon-carbon double bonds. Thus, "$C_2$-$C_{12}$ alkenyl" refers to an alkenyl group having 2 to 12 carbon atoms. "$C_2$-$C_6$ alkenyl" refers to an alkenyl group having 2 to 6 carbon atoms, including vinyl, propenyl, butenyl, 2-methyl-butenyl and cyclohexenyl. A double bond may locate at the straight-chain, branched or cyclic portion of the alkenyl group and, where specified, the alkenyl group may be substituted.

The term "alkynyl" refers to a straight-chain, branched-chain or cyclic hydrocarbyl having the indicated number of carbon atoms and at least one carbon-carbon triple bond. It may have up to three carbon-carbon triple bonds. Thus, "$C_2$-$C_{12}$ alkynyl" refers to an alkynyl group having 2 to 12 carbon atoms. "$C_2$-$C_6$ alkynyl" refers to an alkynyl group having 2 to 6 carbon atoms, including an ethynyl, a propynyl, a butynyl and 3-methyl-1-butynyl and the like.

As used herein, the term "aryl" refers to any stable monocyclic or bicyclic carbocyclic ring containing up to 7 atoms in each ring, wherein at least one ring is an aromatic ring. Examples of the above-mentioned aryl group include phenyl, naphthyl, tetrahydronaphthyl, 2,3-indanyl, biphenyl, phenanthryl, anthryl or acenaphthyl. It can be understood that if an aryl substituent is a bicyclic ring having one non-aromatic ring, then the connection is through the aromatic ring. It also includes the aryl optionally substituted by the substituents selected from the group consisting of: a deuterium, a halogen (F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, a cycloalkenyl, a cycloalkylalkyl, a cycloalkylalkoxy, optionally substituted amino, a hydroxyl, a hydroxyalkyl, an acyl, an aldehyde group, a heteroaryl, a heteroaryloxy, a heterocycloalkyl, a heterocycloalkyloxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a cyano, a thiol, a haloalkyl, a trihaloalkyl and/or an alkylthio.

The term "alkylthio" refers to a cyclic or non-cyclic alkyl group containing the indicated number of carbon atoms and having a connection through a sulfur atom. Thus, "alkylthio" includes the definition of "alkyl" and "cycloalkyl".

The term "halogen" refers to fluorine, chlorine, bromine, iodine, or astatine.

The term "haloalkyl" refers to an alkyl group substituted by halogen at optionally position. Thus, "haloalkyl" includes the definition of "halogen" and "alkyl".

The term "haloalkoxy" refers to an alkoxy group substituted by halogen at optionally position. Thus, the "haloalkoxy" includes the definition of "halogen" and "alkoxy".

The term "aryloxy" refers to an aryl group containing the indicated number of carbon atoms and having a connection through an oxygen bridge. Thus, "aryloxy" includes the definition of "aryl".

As used herein, the term "arylhetero" or "heteroaryl" refers to any stable monocyclic or bicyclic ring containing up to 7 atoms in each ring, wherein at least one ring is an aromatic ring containing 1 to 4 heteroatoms selected from the group consisting of O, N, and S. Heteroaryl groups within the scope of this definition include, but are not limited to, acridinyl, carbazolyl, cinnolinyl, quinoxalinyl, pyrazolyl, imidazolyl, indolyl, indazolyl, triazolyl, tetrazolyl, benzotriazolyl, benzimidazolyl, benzoxazolyl, benzothiazolyl, benzoisoxazolyl, benzisothiazolyl, guanine group, furyl, thienyl, thiazolyl, benzothienyl, benzofuranyl, quinolyl, isoquinolyl, oxazolyl, oxadiazolyl, isoxazolyl, triazinyl, pyrazinyl, pyridazinyl, pyridyl, pyrimidinyl, pyrrolyl, tetrahydroquinolinyl. As the heterocycle defined below, "heteroaryl"

should also be understood to include the N-oxide derivative of any nitrogen-containing heteroaromatic group. It can be understood that if a heteroaryl substituent is a bicyclic ring having one non-aromatic ring or one ring without heteroatom, then the connection is through the aromatic ring or the heteroatom contained in the ring. Heteroaryl groups are optionally substituted by 1 to 4 substituents selected from the group consisting of a deuterium, a halogen, an alkyl, an alkoxy, a hydroxyl, an aryl, an aryloxy, an arylalkyl, a cycloalkyl, an alkylamino, an acylamino, an acyl, an arylcarbonylamino, an amino, a nitro, a cyano, a thiol and/or an alkylthio and/or any alkyl substituents.

As used herein, the term "heterocyclic ring" or "heterocyclic group" refers to 5 to 10 membered aromatic or non-aromatic heterocyclic ring having 1 to 4 heteroatoms selected from the group consisting of O, N, and S, and bicyclic groups are also included. Therefore, the "heterocyclic group" includes the above heteroaryl groups, as well as their dihydro or tetrahydro analogs. Other examples of "heterocyclic group" include, but are not limited to, benzimidazolyl, benzofuranyl, benzofurazanyl, benzopyrazolyl, benzotriazolyl, benzothienyl, benzoxazolyl, carbazyl, carbolinyl, cinnolinyl, furyl, imidazolyl, dihydroindolyl, indolyl, indazolyl, isobenzofuranyl, pseudoindolyl, isoquinoline, isothiazolyl, isoxazolyl, naphthalene pyrimidinyl, oxadiazolyl, oxazolyl, oxazolinyl, isoxazolinyl, oxetanyl, pyranyl, pyrazinyl, pyrazolyl, pyridazinyl, pyridopyridyl, pyridazinyl, pyridyl, pyrimidinyl, pyrrolyl, quinazolinyl, quinolyl, quinoxalinyl, tetrahydropyranyl, tetrazolyl, tetrazopyridyl, thiadiazolyl, thiazolyl, thienyl, triazolyl, azetidinyl, 1,4-dioxanyl, hexahydrodiazepinyl, piperazinyl, piperidinyl, pyrrolidinyl, morpholinyl, thio-morpholinyl, dihydro-benzimidazolyl, dihydro-benzofuranyl, dihydro-benzothienyl, dihydro-benzoxazolyl, dihydro-furyl, dihydro-imidazolyl dihydro-indolyl, dihydro-isoxazolyl, dihydro-isothiazolyl, dihydro-oxadiazolyl, dihydro-oxazolyl, dihydro-pyrazinyl, dihydro-pyrazolyl, dihydropyridyl, dihydro-pyrimidinyl, dihydro-pyrrolyl, dihydro-quinolyl, dihydro-tetrazolyl, dihydro-thiadiazolyl, dihydro-thiazolyl, dihydro-thienyl, dihydro-triazolyl, dihydro-azetidinyl, methylenedioxybenzoyl, tetrahydrofuranyl and tetrahydrothienyl and N-oxides thereof. A heterocyclic group can be linked with other groups through a carbon atom or a heteroatom. As the heterocyclic group can be substituted by substituents selected from the group consisting of: a halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)$_n$NR$^5$R$^6$, —(CR$^8$R$^9$)$_n$OR$^5$, —NR$^5$R$^6$, —NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR$^5$, —OC(=Y)NR$^5$R$^6$, —OS(O)$_2$(OR$^5$), —OP(=Y)(OR$^5$)(OR$^6$), —OP(OR$^5$)(OR$^6$), —SR$^5$, —S(O)R$^5$, —S(O)$_2$R$^5$, —S(O)$_2$NR$^5$R$^6$, —S(O)(OR$^5$), —S(O)$_2$(OR$^5$), —SC(=Y)R$^5$, —SC(=Y)OR$^5$, —SC(=Y)NR$^5$R$^6$, a C$_{1-12}$ alkyl (such as substituted or unsubstituted C$_{1-6}$ alkyl, preferably substituted or unsubstituted C$_{1-3}$ alkyl, whose substituent is preferably a hydroxyl, e.g., together with alkyl forming hydroxylethyl, or t-hydroxy isopropyl), C$_{2-8}$ alkenyl, C$_{2-8}$ alkynyl, C$_{3-12}$ carbocyclic group, C$_{2-20}$ heterocyclic group, C$_{6-20}$ aryl or C$_{1-20}$ heteroaryl; other groups and letters have the meanings given above. The C$_{2-20}$ heterocyclic group is preferably a C$_{2-8}$ saturated heterocyclic group, further preferably a C$_{4-5}$ saturated heterocyclic group, wherein the heteroatom is N, O or S, more preferably a C$_{4-5}$ saturated heterocyclic group containing two heteroatoms, such as piperazinyl or piperidyl. Where the C$_{2-20}$ heterocyclic group has one heteroatom, the substituted position of which is preferably on a carbon atom or a heteroatom; where the C$_{2-20}$ heterocyclic group has two or more heteroatoms, the substituted position of which is preferably on the heteroatom.

The term "heteroalicyclic ring" or "heterocycloalkyl" used herein alone or as a part of other groups refers to a 4 to 12 membered saturated or partially unsaturated ring containing 1 to 4 heteroatoms (such as nitrogen, oxygen and/or sulphur). The heterocycloalkyl groups may include at least one substituents, such as alkyl, halogen, oxo and/or any alkyl substituents set out above. In addition, any heterocycloalkyl rings can be fused to a cycloalkyl, aryl, heteroaryl or heterocycloalkyl ring, thereby to form a fused ring, a bridge ring or a spiro ring. A heterocycloalkyl substituent can be linked with other groups through a carbon atom or a heteroatom therein.

Without departing from common sense of the art, all the above preferred conditions can be combined in any way to provide the preferred embodiments of the present invention.

The materials and reagents used in the present invention are all commercially available.

The room temperature in the present application refers to an environmental temperature which ranges from 10° C. to 35° C.

The positive effect of the present invention is that: the fused heterocyclic compound represented by formula I, II or III in the present invention is an efficient PI3 kinase (especially PI3Kδ-selective) inhibitor which can be used for manufacturing a medicament for preventing and/or treating cell proliferation diseases such as cancer, infections, inflammation and autoimmune diseases.

DETAILED DESCRIPTION OF THE PREFERRED EMBODIMENT

Below in conjunction with specific embodiments, the present invention is further elaborated. But the present invention is not therefore limited within the scope of the embodiments. The following embodiment does not indicate the specific conditions of the experiment, usually in accordance with conventional methods and conditions, or product manual.

Example 1

Synthesis of Compound 1

Synthesis Route of Compound 1

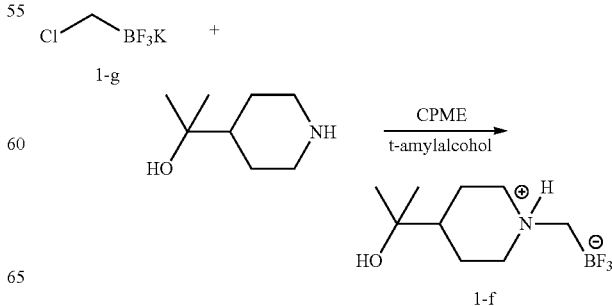

35
-continued

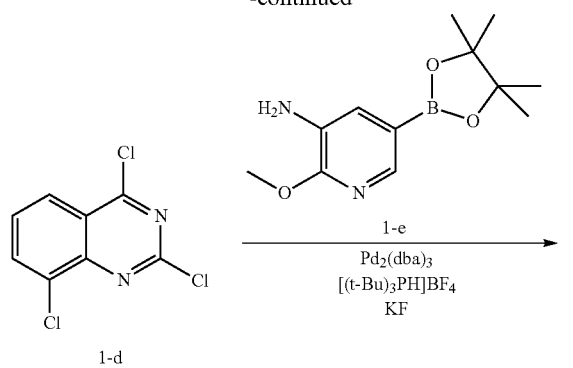

1-d

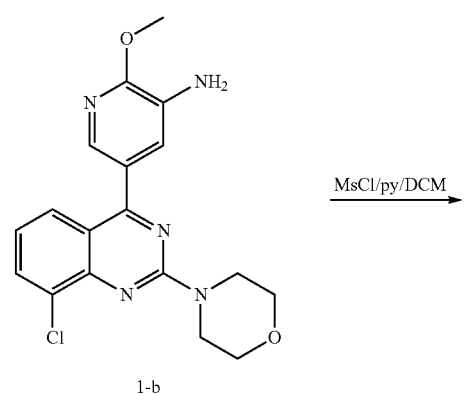

1-c

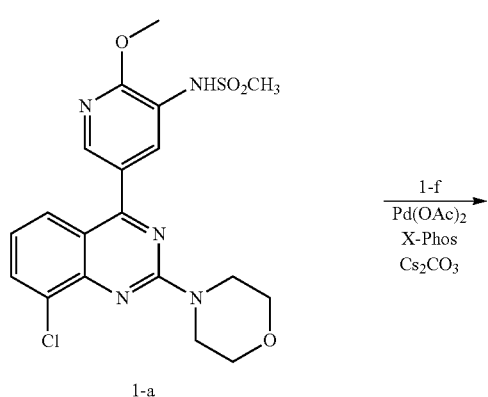

1-b 1-a

36
-continued

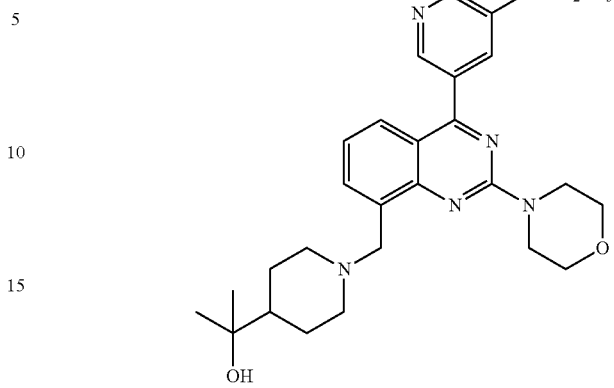

1

Synthesis of Compound 1-f

To a reaction tube were added compound 1-g (prepared according to the method disclosed in J. Org. Chem. 2011, 76, 2762-2769) (0.5 g, 3.2 mmol), 2-(4-piperidyl)-2-propanol (0.46 g, 3.23 mmol), cyclopentyl methyl ether (CPME) (2.1 mL) and tertiary amyl alcohol (0.7 mL). Under nitrogen gas atmosphere, the mixture was stirred overnight at 110° C. The reaction solution was cooled and concentrated under reduced pressure. Acetone (6 mL) was added into the residue and refluxed, ether (10 mL) was added slowly to precipitate, and another portion of ether (90 mL) was added. Cool to room temperature, filtrate, and the filter cake was dried to give compound 1-f (0.77 g, yield 100%). $^1$H NMR (500 MHz, DMSO-$d_6$): δ 9.19 (s, 1H), 4.25 (s, 1H), 3.38 (d, J=12.5 Hz, 2H), 2.67 (t, J=12.5 Hz, 2H), 1.90 (d, J=5.0 Hz, 2H), 1.74 (d, J=13.5 Hz, 2H), 1.44-1.57 (m, 2H), 1.36 (t, J=12.0 Hz, 1H), 1.02 (s, 6H).

Synthesis of Compound 1-c

A mixture of compound 1-d (prepared according to the method disclosed in Heterocycles, 2012, pages 1417-1426) (480 mg, 2.068 mmol), compound 1-e (prepared according to the method disclosed in WO 2009/147187 A1) (510 mg, 2.068 mmol), Pd$_2$(dba)$_3$ (42 mg, 0.046 mmol), [(t-Bu)$_3$PH]BF$_4$ (60 mg, 0.207 mmol), potassium flouride (470 mg, 8.276 mmol), tetrahydrofuran (15 mL) and water (1.5 mL) was heated to 50° C. under nitrogen gas atmosphere and stirred for 7 hours. The reaction solution was concentrated under reduced pressure, and the residue was purified by column chromatograph (elution system: dichloromethane/ethanol=20/1) to give compound 1-c (260 mg, 39%). LC-MS (ESI): m/z=321.0 (M+H)$^+$

Synthesis of Compound 1-b

A mixture of compound 1-c (260 mg), morpholine (160 mg) and N, N-dimethylacetamide (4 mL) was heated to 90° C. and reacted for 1 hour. The reactant was cooled to room temperature, and concentrated under reduced pressure. The residue was diluted by ethyl acetate, and washed with saturated saline. The separated organic layer was dried over anhydrous sodium sulphate, and concentrated under reduced pressure to give crude compound 1-b (260 mg). LC-MS (ESI): m/z=372.1 (M+H)+.

Synthesis of Compound 1-a

A solution of compound 1-b (260 mg), pyridine (2 mL) and methylsulfonyl chloride (300 mg) in dichloromethane (10 mL) was stirred overnight at room temperature. The reaction solution was concentrated under reduced pressure. The residue was purified by silica column chromatograph (elution system: dichloromethane/ethanol=30/1) to give compound 1-a (150 mg, total yield for two steps is 41%). LC-MS (ESI): m/z=449.9 (M+H)+.

Synthesis of Compound 1

A suspension of compound 1-a (150 mg, 0.305 mmol), compound 1-f (176 mg, 0.672 mmol), palladium acetate (10 mg, 0.045 mmol), x-Phos (20 mg, 0.045 mmol), cesium carbonate (365 mg, 1.120 mmol), tetrahydrofuran (15 mL) and water (1.5 mL) was heated to 72° C. under nitrogen atmosphere and stirred overnight. The reaction solution was cooled, then sodium hydroxide (80 mg) and methanol (10 mL) were added, and stirred for another 2 hours at room temperature. The reaction solution was neutralized with 1N hydrochloride, and concentrated under reduced pressure. The residue was separated and purified by silica preparative plate chromatograph (developing system: dichloromethane/methanol=8/1) to give compound 1 (70 mg, 55%). LC-MS (ESI): m/z=571.2 (M+H)+; $^1$H NMR (400 MHz, CD$_3$OD): δ8.15 (d, J=2.4 Hz, 1H), 7.99 (d, J=2.4 Hz, 1H), 7.71 (d, J=7.2 Hz, 1H), 7.62 (d, J=6.0 Hz, 1H), 7.07 (t, J=7.2 Hz, 1H), 3.97 (s, 5H), 3.81 (t, J=4.8 Hz, 4H), 3.66 (t, J=4.8 Hz, 4H), 3.03 (d, J=12.0 Hz, 2H), 2.92 (s, 3H), 2.12 (t, J=12.0 Hz, 2H), 1.64 (d, J=12.0 Hz, 2H), 1.14-1.37 (m, 3H), 1.01 (s, 6H).

Example 2

Synthesis of Compound 2

Synthesis Route of Compound 2

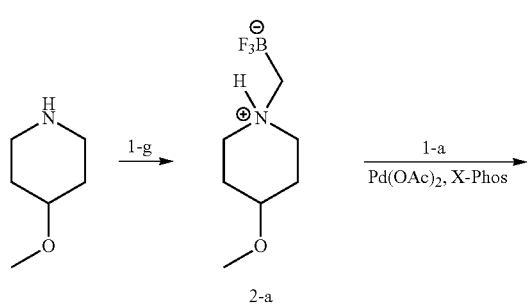

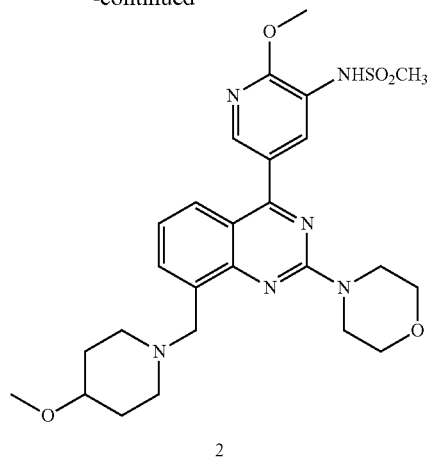

Synthesis of Compound 2-a

According to the process for preparing compound 1-f, commercially available 4-methoxy piperidine was used to give compound 2-a (800 mg, 78%) which was white solid. $^1$H NMR (400 MHz, DMSO-d$_6$): δ 8.29 (s, 1H), 3.23 (s, 6H), 2.48 (s, 1H), 2.12 (s, 1H), 1.92 (d, J=4.9 Hz, 4H), 1.86 (s, 2H).

Synthesis of Compound 2

According to the process for preparing compound 1, compound 2-a was used to give compound 2 (10 mg, 21%). LC-MS (ESI): m/z=543.2 (M+H)+. $^1$H NMR (400 MHz, CDCl$_3$): δ8.28 (d, J=2.0 Hz, 1H), 8.11 (d, J=2.0 Hz, 1H), 7.74 (d, J=6.8 Hz, 1H), 7.68 (d, J=8.4 Hz, 1H), 7.13 (t, J=7.2 Hz, 1H), 4.04 (s, 3H), 3.98 (s, 2H), 3.89-3.91 (m, 4H), 3.74-3.77 (m, 4H), 3.27 (s, 3H), 3.15-3.21 (m, 1H), 2.99 (s, 3H), 2.80-2.83 (m, 2H), 2.24-2.29 (m, 2H), 1.86-1.88 (m, 2H), 1.54-1.63 (m, 2H).

Example 3

Synthesis of Compound 3

Synthesis Route of Compound 3

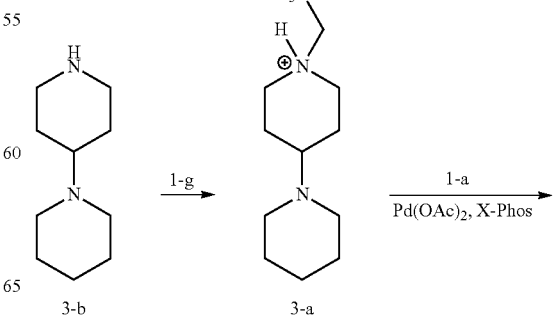

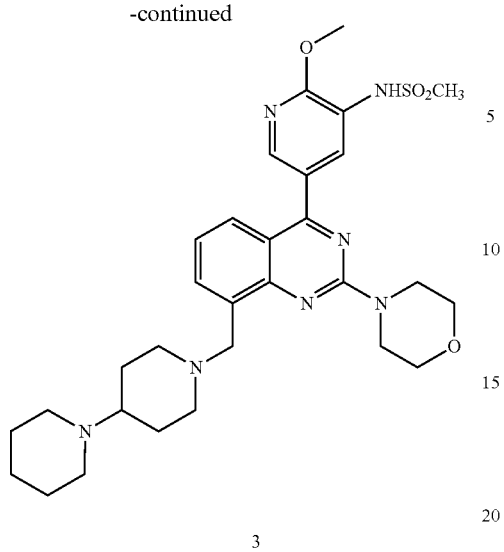

3

Synthesis of Compound 3-a

According to the process for preparing compound 1-f, commercially available compound 3-b was used to give compound 3-a (700 mg, 89%) which was white solid.

Synthesis of Compound 3

According to the process for preparing compound 1, compound 3-a was used to give compound 3 (48 mg, 72%). LC-MS (ESI): m/z=596.3 (M+H)+. $^1$H NMR (400 MHz, CDCl$_3$) δ 8.35 (d, J=2.0 Hz, 1H), 8.18 (d, J=2.0 Hz, 1H), 7.74-7.80 (m, 2H), 7.19 (t, J=7.2 Hz, 1H), 4.11 (s, 3H), 4.03 (s, 2H), 3.96-3.98 (m, 4H), 3.82-3.84 (m, 4H), 3.06-3.10 (m, 5H), 2.53-2.55 (m, 4H), 2.30-2.37 (m, 1H), 2.12-2.18 (m, 2H), 1.79-1.82 (m, 2H), 1.57-1.72 (m, 6H), 1.43-1.45 (m, 2H).

Example 4

Synthesis of Compound 4

Synthesis Route of Compound 4

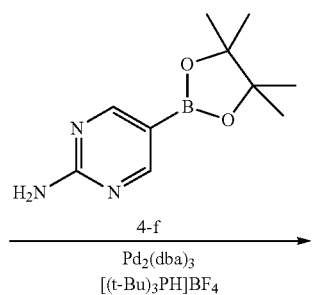

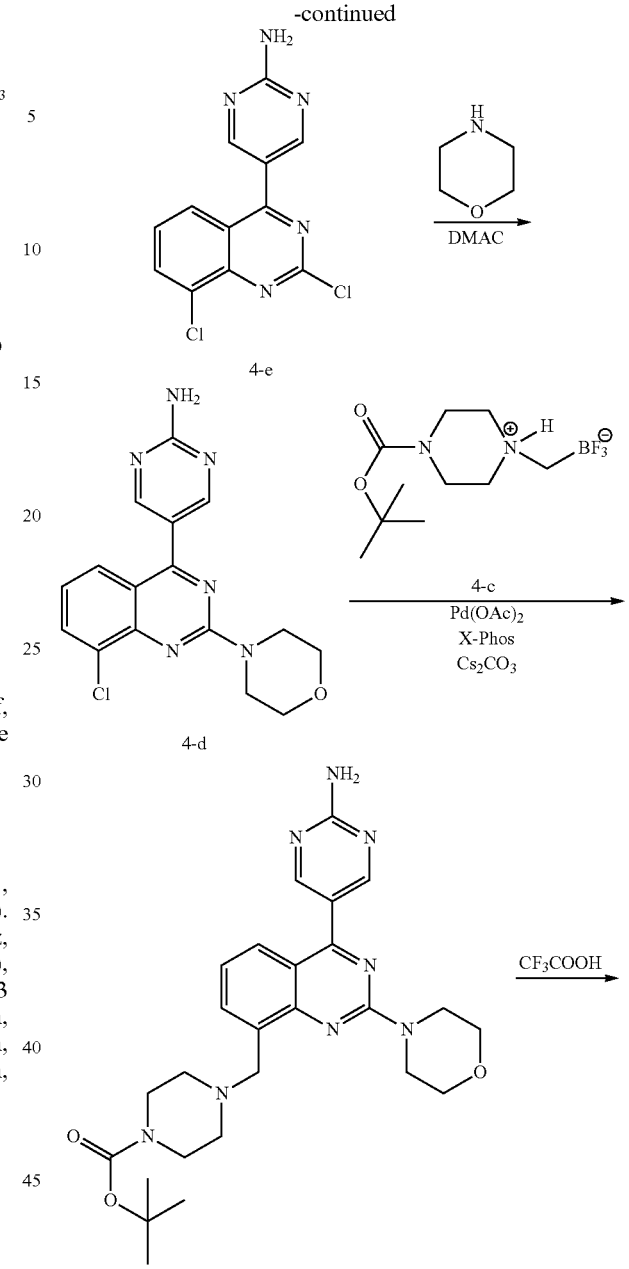

-continued

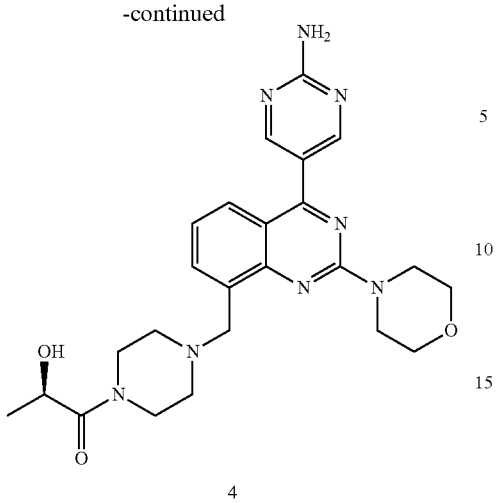

4

Synthesis of Compound 4-e

According to the process for preparing compound 1-c, commercially available compound 4-f was used to give compound 4-e (0.69 g, 56%). LC-MS (ESI): m/z=293 (M+H)+.

Synthesis of Compound 4-d

A mixture of compound 4-e (0.68 g), morpholine (4 mL) and N, N-dimethylacetamide (40 mL) was heated to 90° C. and reacted for 1 hour. The reactant was cooled to room temperature, and filtrated to collect precipitate to give compound 4-d (623 mg, 78%). LC-MS (ESI): m/z=343.1 (M+H)+.

Synthesis of Compound 4-b

According to the process for preparing compound 1, compound 4-d and compound 4-c (prepared according to the method disclosed in J. Org. Chem. 2011, 76, 2762-2769) were used to give compound 4-b (140 mg, 94%). LC-MS (ESI): m/z=507.3 (M+H)+.

Synthesis of Compound 4-a

A solution of compound 4-b (140 mg, 0.276 mmol) in dichloromethane/trifloroacetic acid (v/v, 2/1, 15 mL) was stirred at room temperature for half an hour. The reaction solution was concentrated under reduced pressure. The residue was dissolved in 5 mL methanol, and then neutralized to alkalinity by adding an excess amount of solid potassium carbonate, and diluted with 10 mL dichloromethane. The mixture was filtrated by a short silica column, and eluted with a mixed solution of dichloromethane/methanol (v/v, 10/1). The filtrate was concentrated under reduced pressure to give crude compound 4-a (110 mg, 98%). LC-MS (ESI): m/z=407.3 (M+H)+.

Synthesis of Compound 4

To a mixed solution of compound 4-a (110 mg, 0.278 mmol), D-lactic acid (25 mg, 0.278 mmol), diisopropylethylamine (0.1 mL) and N, N-dimethylacetamide (2 mL) was added 1-ethyl-3-(3-dimethylaminopropyl)-carbodiimide hydrochloride (52 mg, 0.271 mmol), and stirred for 2 hours at room temperature. The reaction solution was filtered. The filtrate was purified by Preparative HPLC to give compound 4 (30 mg, 23%). LC-MS (ESI): m/z=479.3 (M+H)+. $^1$H NMR (400 MHz, CDCl$_3$) δ 8.68 (s, 2H), 7.69-7.73 (m, 2H), 7.14 (t, J=8.0 Hz, 1H), 5.54 (s, 2H), 4.37-4.40 (m, 1H), 4.00 (s, 2H), 3.88-3.91 (m, 5H), 3.75-3.77 (m, 4H), 3.54-3.74 (m, 2H), 3.34-3.42 (m, 2H), 2.50-2.58 (m, 4H), 1.25 (d, J=6.4 Hz, 3H).

Example 5

Synthesis of Compound 5

Synthesis Route of Compound 5

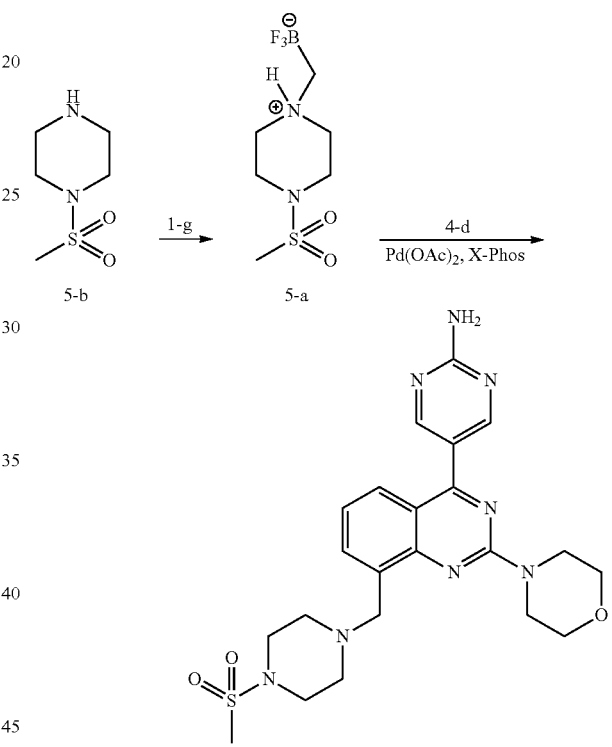

5

Synthesis of Compound 5-a

According to the process for preparing compound 1-f, commercially purchased compound 5-b was used to give compound 5-a (7 g, yield 62%). $^1$H NMR (500 MHz, DMSO-d$_6$): δ 8.94 (1H, brs), 3.51-3.69 (2H, m), 3.37-3.50 (2H, m), 3.06-3.22 (2H, m), 2.89-3.04 (2H, m), 2.97 (3H, s), 2.03 (2H, q, J=5.0 Hz).

Synthesis of Compound 5

According to the process for preparing compound 1, compound 4-d and compound 5-a were used to give compound 5 (15 mg, 10%). LC-MS (ESI): m/z=485.2 (M+H)+. $^1$H NMR (400 MHz, CDCl$_3$) δ 8.67 (s, 2H), 7.69-7.71 (m, 2H), 7.13 (t, J=8.0 Hz, 1H), 5.43 (s, 2H), 4.02 (s, 2H), 3.89-3.92 (m, 4H), 3.75-3.78 (m, 4H), 3.20-3.23 (m, 4H), 2.72 (s, 3H), 2.63-2.66 (m, 4H).

Example 6

Synthesis of Compound 6

Synthesis Route of Compound 6

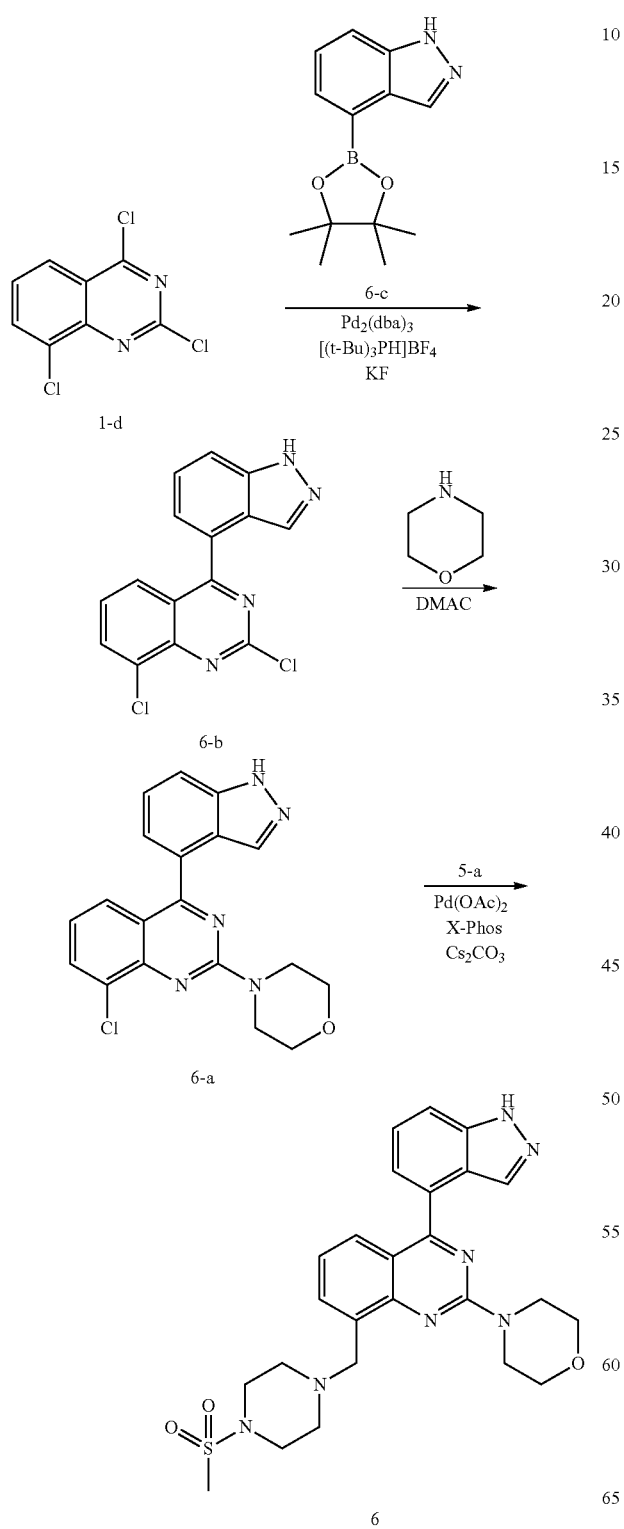

Synthesis of Compound 6-b

According to the process for preparing compound 1-c, commercially purchased compound 6-c was used to give compound 6-b (0.56 g, 43%). LC-MS (ESI): m/z=316 (M+H)$^+$.

Synthesis of Compound 6-a

A mixture of compound 6-b (190 mg), morpholine (0.4 mL) and N, N-dimethylacetamide (10 mL) was heated to 80° C. and reacted for 1 hour. The reactant was cooled to room temperature, and concentrated under reduced pressure. The residue was separated and purified by silica column chromatograph (elution system: dichloromethane/methanol=10/1) to give compound 6-a (140 mg, 64%). LC-MS (ESI): m/z=366.1 (M+H)$^+$.

Synthesis of Compound 6

According to the process for preparing compound 1, compound 6-a and compound 5-a were used to give compound 6 (21 mg, 26%). LC-MS (ESI): m/z=508.2 (M+H)$^+$. $^1$H NMR (400 MHz, CDCl$_3$) δ 8.04 (s, 1H), 7.69-7.72 (m, 2H), 7.60 (d, J=8.4 Hz, 1H), 7.48 (t, J=8.0 Hz, 1H), 7.41 (d, J=6.8 Hz, 1H), 7.07 (t, J=8.0 Hz, 1H), 4.07 (s, 2H), 3.92-3.94 (m, 4H), 3.76-3.79 (m, 4H), 3.23-3.25 (m, 4H), 2.69-2.72 (m, 7H).

Example 7

Synthesis of Compound 7

Synthesis Route of Compound 7

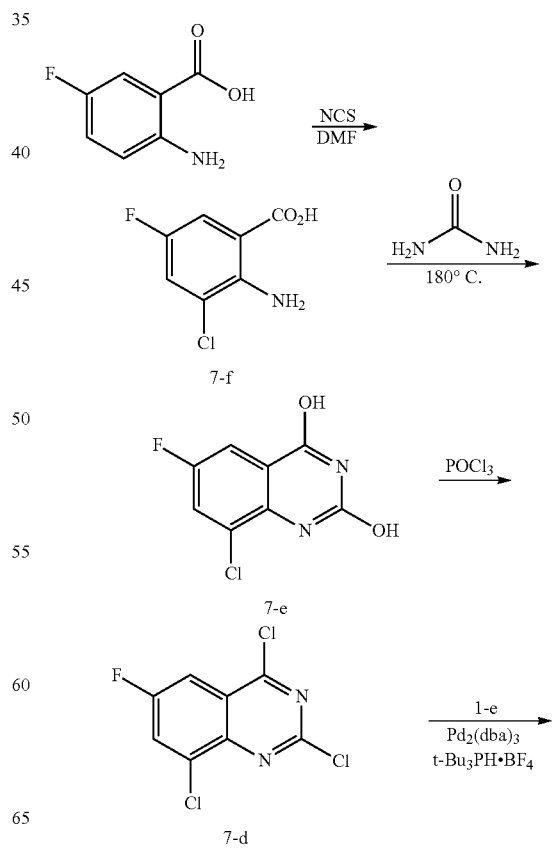

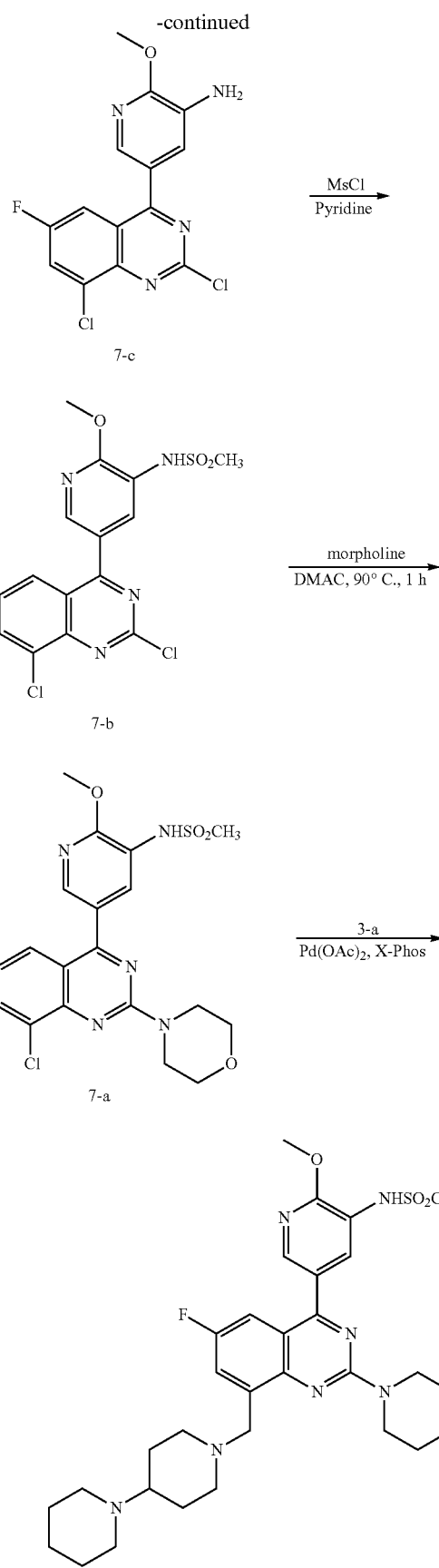

Synthesis of Compound 7-f

A mixture of 2-amino-5-fluorobenzoic acid (5.0 g, 32.26 mmol), NCS (4.39 g, 32.9 mmol) and DMF (30 mL) was stirred at room temperature for 16 hours. The reaction solution was diluted with water (100 mL) and extracted with ethyl acetate (3×100 mL). The organic layer was combined, washed with saturated saline, dried over anhydrous sodium sulphate, and concentrated under reduced pressure. The residue was stirred with dichloromethane (100 mL) for 10 minutes, and filtrated to give compound 7-f (3.4 g, yield 56%), which was grey solid. LC-MS (ESI): m/z=190.0 (M+H)$^+$.

Synthesis of Compound 7-e

A mixture of compound 7-f (3.4 g, 18 mmol) and carbamide (10.8 g, 180 mmol) was stirred at 180° C. for 3 hours. The reaction mixture was cooled, and the precipitated solid was washed with water, and dried to give compound 7-e (3.8 g, 99%) which was grey solid powder. LC-MS (ESI): m/z=215.0 (M+H)$^+$.

Synthesis of Compound 7-d

A mixture of compound 7-e (3.1 g, 14.5 mmol) and phosphorus oxychloride (30 mL) was stirred at 110° C. for 16 hours. The reaction mixture was cooled and concentrated under reduced pressure. The residue was added with ice water and extracted with dichloromethane (3×100 mL). The organic layer was combined and washed with saturated saline, dried over anhydrous sodium sulphate, and concentrated under reduced pressure. The residue was separated and purified by silica column chromotograph (elution system: petroleum ether/ethyl acetate=50/1) to give compound 7-d (1.8 g, 50%) which was white solid. LC-MS (ESI): m/z=251.1 (M+H)$^+$.

Synthesis of Compound 7-c

A solution of compound 7-d (400 mg, 1.6 mmol), compound 1-e (400 mg, 1.6 mmol), Pd$_2$(dba)$_3$ (30 mg, 0.032 mmol), t-Bu$_3$PH.BF$_4$(24 mg, 0.08 mmol), potassium fluoride (372 mg, 6.4 mmol) and a mixture of THF and water (10/1, v/v, 25 mL) was stirred at 50° C. for 2 hours under nitrogen gas atmosphere. The reaction mixture was concentrated under reduced pressure. The residue was added with dichloromethane (50 mL), washed in sequence with water and saturated saline, dried over anhydrous sodium sulphate, and concentrated under reduced pressure. The residue was separated and purified by silica column chromatograph (elution system: petroleum ether/ethyl acetate=25/1 to 10/1) to give compound 7-c (150 mg, 28%) which was yellow solid. LC-MS (ESI): m/z=339.0 (M+H)$^+$.

Synthesis of Compound 7-b

To a mixture of compound 7-c (150 mg, 0.44 mmol), pyridine (4 mL) and dichloromethane (30 mL) was added dropwise methylsulfonyl chloride (254 mg, 2.22 mmol), and stirred for 16 hours at room temperature. The reaction solution was concentrated under reduced pressure. The residue was added with dichloromethane (50 mL), washed in sequence with water and saturated saline, dried over anhydrous sodium sulphate, and concentrated under reduced pressure. The residue was separated and purified with silica column chromotograph (elution system: petroleum ether/ ethyl acetate=1/1) to give compound 7-b (50 mg, 27%), which was yellow solid. LC-MS (ESI): m/z=417.0 (M+H)⁺.

Synthesis of Compound 7-a

A mixture of compound 7-b (50 mg, 0.12 mmol), morpholine (52 mg, 0.60 mmol) and N, N-dimethylacetamide (2 mL) was stirred at 90° C. for 1 hour. The reaction mixture was diluted with ethyl acetate (20 mL), washed in sequence with water and saturated saline, dried over anhydrous sodium sulphate, and concentrated under reduced pressure to give compound 7-a (55 mg, 98%) which was yellow solid. LC-MS (ESI): m/z=468.1 (M+H)⁺.

Synthesis of Compound 7

According to the process for preparing compound 1, compound 7-a and compound 3-a were used to give compound 7 (40 mg, 61%). LC-MS (ESI): m/z=614.2 (M+H)⁺. $^1$H NMR (400 MHz, CDCl$_3$) δ 8.32 (1H, d, J=2.0 Hz), 8.16 (1H, d, J=2.0 Hz), 7.66-7.62 (1H, m), 7.38-7.34 (1H, m), 4.11 (3H, s), 4.00 (2H, s), 3.93 (4H, t, J=4.4 Hz), 3.82 (4H, t, J=4.4 Hz), 3.07-3.04 (5H, m), 2.64-2.61 (4H, m), 2.48-2.42 (2H, m), 2.21-2.15 (2H, m), 1.91-1.87 (2H, m), 1.76-1.67 (6H, m), 1.48-1.46 (2H, m).

Example 8

Synthesis of Compound 8

Synthesis Route of Compound 8

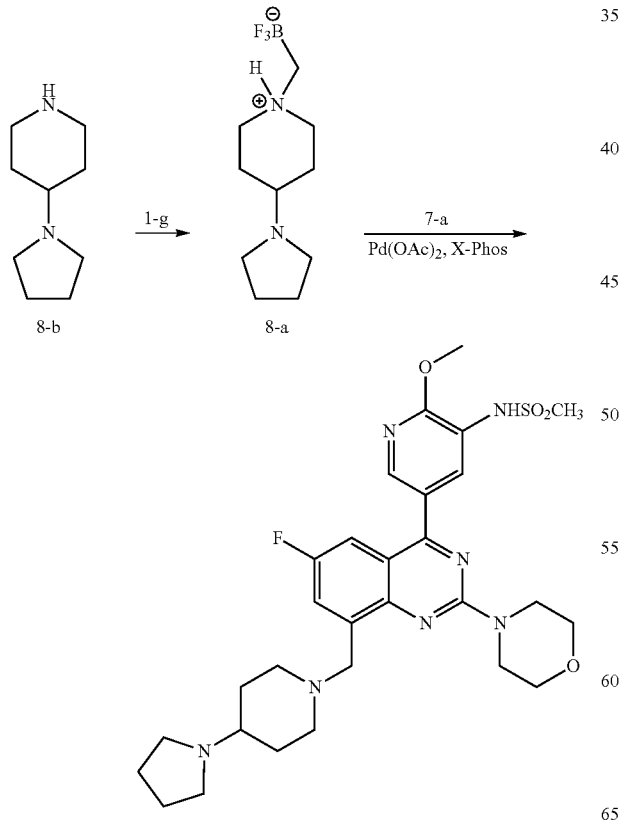

Synthesis of Compound 8-a

According to the process for preparing compound 1-f, commercially purchased compound 8-b was used to give compound 8-a (500 mg, 68%) which was white solid.

Synthesis of Compound 8

According to the process for preparing compound 1, compound 8-a and compound 7-a were used to give compound 8 (30 mg, 36%). LC-MS (ESI): m/z=600.3 (M+H)⁺. $^1$H NMR (400 MHz, CDCl$_3$) δ 8.32 (1H, d, J=2.4 Hz), 8.16 (1H, d, J=2.4 Hz), 7.68-7.65 (1H, m), 7.38-7.34 (1H, m), 4.12 (3H, s), 4.02 (2H, s), 3.94-3.91 (4H, m), 3.82 (4H, t, J=4.4 Hz), 3.07-3.02 (5H, m), 2.90-2.88 (3H, m), 2.47-2.45 (2H, m), 2.25-2.19 (2H, m), 2.01-1.81 (8H, m).

Example 9

Synthesis of Compound 9

Synthesis Route of Compound 9

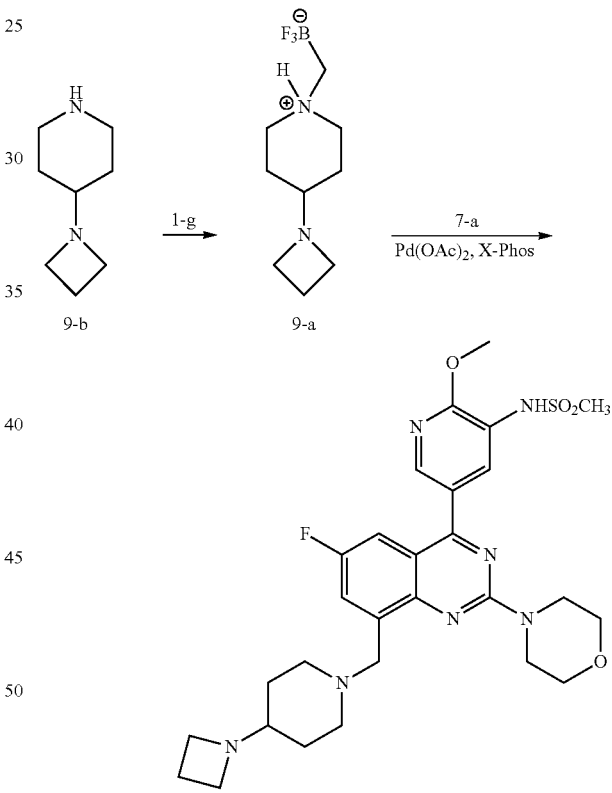

Synthesis of Compound 9-a

According to the process for preparing compound 1-f, commercially purchased compound 9-b was used to give compound 9-a (180 mg, 62%) which was white solid.

Synthesis of Compound 9

According to the process for preparing compound 1, compound 9-a and compound 7-a were used to give compound 9 (20 mg, 36%). LC-MS (ESI): m/z=586.3 (M+H)+. 1H NMR (400 MHz, CDCl3) δ 8.32 (1H, d, J=2.0 Hz), 8.16 (1H, d, J=2.0 Hz), 7.67-7.65 (1H, m), 7.40-7.34 (1H, m), 4.12 (3H, s), 4.03 (2H, s), 3.93 (4H, t, J=4.4 Hz), 3.82 (4H, t, J=4.4 Hz), 3.70 (1H, s), 3.37-3.35 (3H, m), 3.07 (3H, s), 2.99-2.95 (2H, m), 2.25-2.14 (5H, m), 1.78-1.75 (2H, m), 1.55-1.47 (2H, m).

Example 10

Synthesis of Compound 10

Synthesis Route of Compound 10

Example 11

Synthesis of Compound 11

Synthesis Route of Compound 11

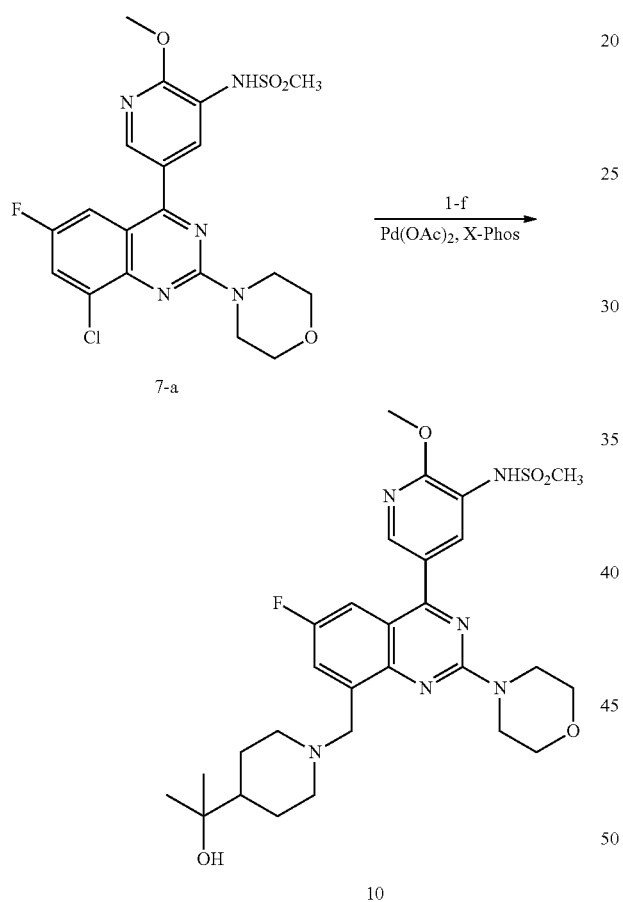

Synthesis of Compound 10

According to the process for preparing compound 1, compound 7-a was used to give compound 10 (19 mg, 61.3%). LC-MS (ESI): m/z=589.2 (M+H)+. 1H NMR (400 MHz, CDCl3) δ 8.33 (1H, d, J=2.0 Hz), 8.17 (1H, d, J=2.4 Hz), 7.70-7.68 (1H, m), 7.38-7.35 (1H, m), 4.12 (3H, s), 4.03 (2H, s), 3.95 (4H, t, J=4.4 Hz), 3.83 (4H, t, J=4.4 Hz), 3.11-3.05 (5H, m), 2.16 (2H, t, J=10.8 Hz), 1.77 (2H, d, J=12.4 Hz), 1.51-1.45 (2H, m), 1.37-1.34 (1H, m), 1.21 (6H, s).

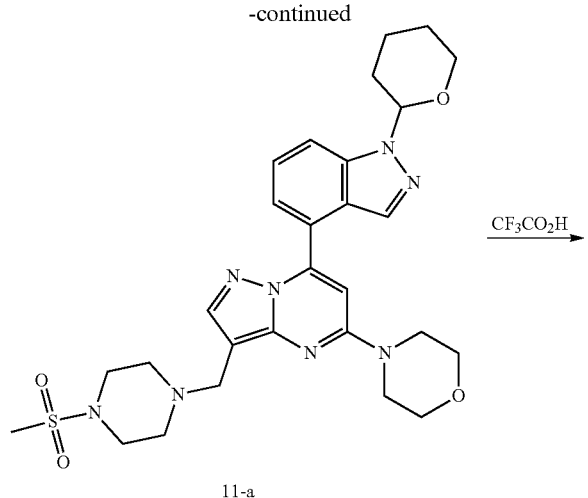

11-a

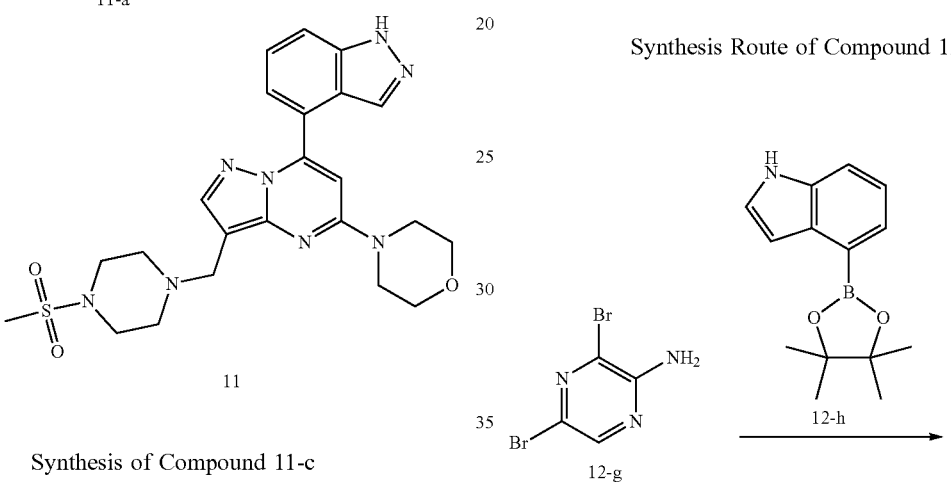

11

Synthesis of Compound 11-c

A mixture of compound 11-d (prepared according to the method disclosed in WO 2004/087707A1) (300 mg, 1.12 mmol), 11-e (prepared according to the method disclosed in Synlett 2009, No. 4, 615-619) (367 mg, 1.12 mmol), PdCl$_2$(dppf).CH$_2$Cl$_2$ (90 mg, 0.112 mmol), 2N aqueous solution of sodium carbonate (4.48 mL, 8.96 mmol) and dimethoxyethane (12 mL) was stirred overnight at 85° C. under nitrogen gas atmosphere. The reaction mixture was filtrated through celite, and the filtrate was concentrated under reduced pressure. The residue was purified by column chromatograph (elution system: petroleum ether/ethyl acetate=4/1) to give compound 11-c (261 mg, 54%). LC-MS (ESI): m/z=432 (M+H)$^+$.

Synthesis of Compound 11-b

According to the process for preparing compound 6-a, compound 11-c was used to give compound 11-b (256 mg, 88%). LC-MS (ESI): m/z=505 (M+Na)$^+$.

Synthesis of Compound 11-a

According to the process for preparing compound 1, compound 11-b and compound 5-a were used to give compound 11-a (30 mg, 28%). LC-MS (ESI): m/z=581 (M+H)$^+$.

Synthesis of Compound 11

To a solution of compound 11-a (30 mg, 0.052 mmol) in dichloromethane (2.0 mL) was added slowly dropwise trifluoroacetic acid (0.076 mL, 1.04 mmol), and stirred for 3 hours at room temperature. The reaction solution was diluted with ethyl acetate (15 mL), washed with aqueous ammonia (2×10 mL). The organic phase was separated, dried over anhydrous sodium sulphate, and concentrated under reduced pressure to give compound 11 (26 mg, 100%). LC-MS (ESI): m/z=497 (M+H)$^+$; $^1$H NMR (500 MHz, CDCl$_3$) δ7.88 (1H, s), 7.28 (1H, s), 7.60 (1H, d, J=7.0 Hz), 7.56 (1H, d, J=8.0 Hz), 7.44 (1H, t, J=7.5 Hz), 6.45 (1H, s), 3.77 (4H, t, J=5.0 Hz), 3.71 (2H, s), 3.64 (4H, t, J=5.0 Hz), 3.21 (4H, s), 2.70 (3H, s), 2.64 (4H, s).

Example 12

Synthesis of Compound 12

Synthesis Route of Compound 12

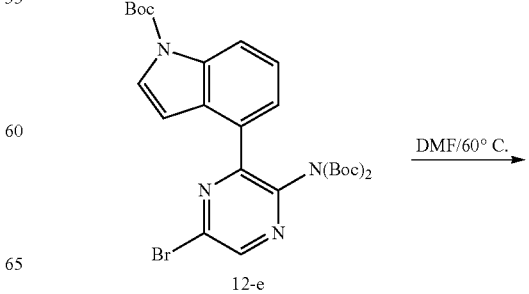

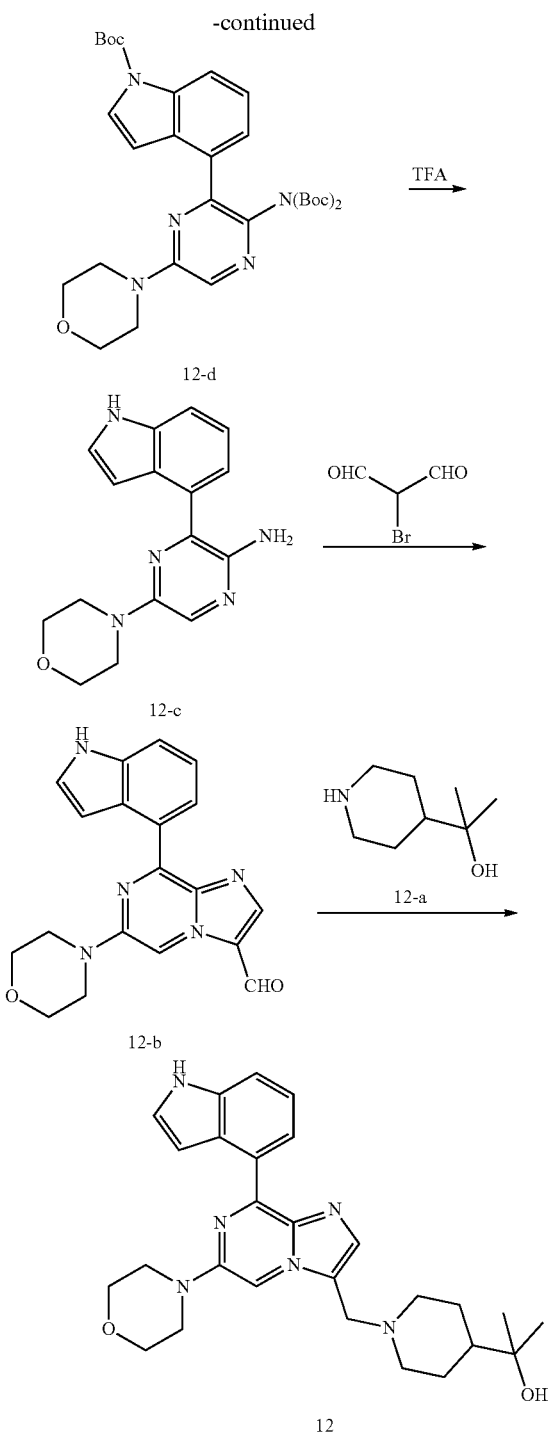

chromatograph (elution system: dichloromethane/methanol=10/1) to give compound 12-f (0.68 g, 60%). LC-MS (ESI): m/z=289.0 (M+H)$^+$.

Synthesis of Compound 12-e

A mixed solution of Boc$_2$O (1.25 mmol), 4-dimethylaminopyridine (10 mg), compound 12-f (90 mg, 0.25 mmol) and THF (20 mL) was stirred overnight at room temperature. The reaction solution was concentrated under reduced pressure, and the residue was separated and purified with silica column chromatograph (petroleum ether/ethyl acetate=5/1 to 2/1) to give compound 12-e (0.91 g, 75%) which was white solid.

Synthesis of Compound 12-d

To a solution of compound 12-e (886 mg, 1.50 mmol) in DMF (20 mL) was added morpholine (0.7 mL, 7.95 mmol), and the reaction solution was stirred at 60° C. overnight. Water (10 mL) was added into the reaction mixture and the mixture was filtrated. The filter cake was washed with water, dried, and then purified by silica column chromatograph to give compound 12-d (875 mg, 98%).

Synthesis of Compound 12-c

To a solution of compound 12-d (900 mg, 0.19 mmol) in dichloromethane (4 mL) was added dropwise trifluoroacetic acid (3 mL), and the reaction solution was stirred for 1 hour at room temperature. The reaction solution was concentrated under reduced pressure. The residue was adjusted to alkalinity with saturated aqueous solution of sodium carbonate, and extracted with ethyl acetate. The organic layers were combined, washed in sequence with water and saturated sodium chloride, dried with anhydrous sodium sulphate, and concentrated under reduced pressure to give compound 12-c (370 mg, 83%) which was yellow solid.

Synthesis of Compound 12-b

A mixture of compound 12-c (170 mg, 0.58 mmol), 2-bromomalonaldehyde (102 mg, 0.68 mmol) and acetonitrile (10 mL) was stirred at 50° C. overnight. The reaction solution was adjusted to pH>8 with saturated aqueous solution of sodium bicarbonate, and extracted with ethyl acetate. The organic layers were combined, washed with saturated sodium chloride, dried over anhydrous sodium sulphate, and concentrated under reduced pressure to give compound 12-b, which was used directly in the next reaction.

Synthesis of Compound 12

To the solution of compound 12-b (230 mg, 0.58 mmol) obtained from the previous step in 1,2-dichloroethane (3 mL) were added compound 12-a (107 mg, 0.75 mmol), sodium cyanoborohydride (109 mg, 1.73 mmol) and acetic acid (1 drop), and the reaction solution was stirred at 25° C. overnight. The reaction solution was diluted with saturated aqueous solution of sodium bicarbonate (10 mL), and extracted with dichloromethane. The organic layers were combined, washed with water and saturated aqueous solution of sodium chloride in sequence, dried over anhydrous sodium sulphate, and concentrated under reduced pressure. The residue was separated and purified by Preparative TLC to give compound 12 (8 mg, two steps 3%). LC-MS (ESI):

Synthesis of Compound 12-f

A mixture of compound 12-g (1 g, 3.35 mmol), compound 12-h (1.05 g, 4.11 mmol), triphenylphosphine (0.21 g, 0.80 mmol), palladium acetate (0.09 g, 0.40 mmol), THF (50 mL) and saturated aqueous solution of sodium bicarbonate (5 mL) was stirred overnight at 90° C. under nitrogen gas atmosphere. The reaction solution was diluted with THF, filtrated through celite, and the filter cake was washed with THF. The filtrate was concentrated under reduced pressure. The residue was separated and purified with silica column m/z=475.3 (M+H)+. 1H NMR (400 MHz, CDCl3) δ 8.33-8.48 (2H, m), 7.62 (1H, s), 7.61 (1H, s), 7.51 (1H, d, J=8.0 Hz), 7.36 (1H, t, J=8.0 Hz), 7.30 (1H, t, J=2.8 Hz), 7.12 (1H, t, J=2.0 Hz), 3.94 (4H, t, J=4.8 Hz), 3.81 (2H, s), 3.46 (4H, t, J=4.8 Hz), 2.97 (2H, d, J=11.2 Hz), 2.02 (2H, t, J=10.8 Hz), 1.72-1.83 (2H, m), 1.28-1.39 (3H, m), 1.18 (6H, s).

Example 13

Synthesis of Compound 13

Synthesis Route of Compound 13

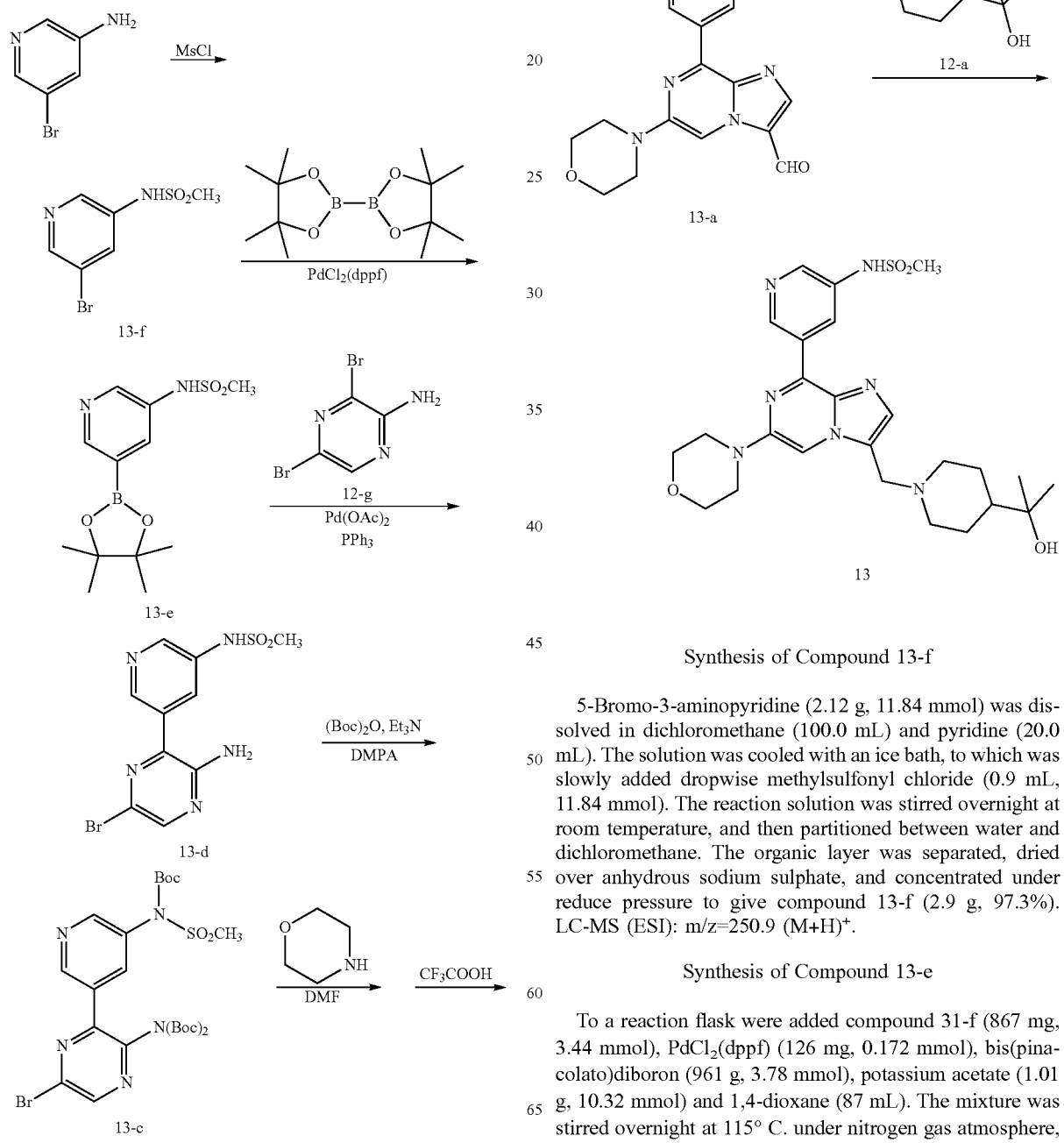

Synthesis of Compound 13-f

5-Bromo-3-aminopyridine (2.12 g, 11.84 mmol) was dissolved in dichloromethane (100.0 mL) and pyridine (20.0 mL). The solution was cooled with an ice bath, to which was slowly added dropwise methylsulfonyl chloride (0.9 mL, 11.84 mmol). The reaction solution was stirred overnight at room temperature, and then partitioned between water and dichloromethane. The organic layer was separated, dried over anhydrous sodium sulphate, and concentrated under reduce pressure to give compound 13-f (2.9 g, 97.3%). LC-MS (ESI): m/z=250.9 (M+H)+.

Synthesis of Compound 13-e

To a reaction flask were added compound 31-f (867 mg, 3.44 mmol), PdCl2(dppf) (126 mg, 0.172 mmol), bis(pinacolato)diboron (961 g, 3.78 mmol), potassium acetate (1.01 g, 10.32 mmol) and 1,4-dioxane (87 mL). The mixture was stirred overnight at 115° C. under nitrogen gas atmosphere, and then concentrated under reduced pressure. The residue was dissolved in ethyl acetate (250 mL), and filtrated through celite. The filtrate was concentrated under reduced pressure to give 13-e (1.6 g) and the crude product was used in the next step without purification. LC-MS (ESI): m/z=299 (M+H)$^+$.

Synthesis of Compound 13-d

According to the process for preparing compound 12-f, compound 13-e was used to give compound 13-d (571 mg, 42%) which was white solid. LC-MS (ESI): m/z=344.9 (M+H)$^+$.

Synthesis of Compound 13-c

According to the process for preparing compound 12-e, compound 13-d was used to give compound 13-c (693 mg, 65%) which was white solid. LC-MS (ESI): m/z=644.0 (M+H)$^+$.

Synthesis of Compound 13-b

To a solution of compound 13-c (693 mg, 1.1 mmol) in DMF (15 mL) was added morpholine (0.39 mL, 4.4 mmol), and the reaction solution was stirred overnight at 60° C. The reaction mixture was added with water (30 mL), and extracted with ethyl acetate. The organic layers were combined, washed with water and saturated aqueous solution of sodium chloride in sequence, dried over anhydrous sodium sulphate, and concentrated under reduced pressure. The residue was dissolved in dichloromethane (6 mL), added with trifluoroacetic acid (3 mL), and stirred at room temperature for 1 hour. The reaction solution was concentrated under reduced pressure. The residue was adjusted to alkalinity with saturated aqueous solution of sodium carbonate, and extracted with ethyl acetate. The organic layers were combined, washed with water and saturated aqueous solution of sodium chloride in sequence, dried over anhydrous sodium sulphate, and concentrated under reduced pressure to give compound 13-b (234 mg, 60.8%) which was yellow solid. LC-MS (ESI): m/z=351 (M+H)$^+$.

Synthesis of Compound 13-a

According to the process for preparing compound 12-b, compound 13-b was used to give compound 13-a (50 mg, 29%) which was yellow solid. LC-MS (ESI): m/z=403.0 (M+H)$^+$.

Synthesis of Compound 13

According to the process for preparing compound 12, compound 13-a was used to give compound 13 (8 mg, 15%) which was yellow solid. LC-MS (ESI): m/z=530.0 (M+H)$^+$. $^1$H NMR (400 MHz, CDCl$_3$) δ 9.42 (d, 1H, J=1.6 Hz), 8.91 (s, 1H), 8.39 (d, 1H, J=2.4 Hz), 7.72 (s, 1H), 7.67 (s, 1H), 3.94 (t, 4H, J=4.4 Hz), 3.85 (s, 2H), 3.43 (t, 4H, J=4.4 Hz), 3.13 (s, 3H), 2.97 (d, 2H, J=9.2 Hz), 2.07 (t, 2H, J=8.0 Hz), 1.78 (d, 2H, J=8.8 Hz), 1.39-1.40 (m, 1H), 1.34 (s, 2H), 1.18 (s, 6H).

Example 14

Synthesis of Compound 14

Synthesis Route of Compound 14

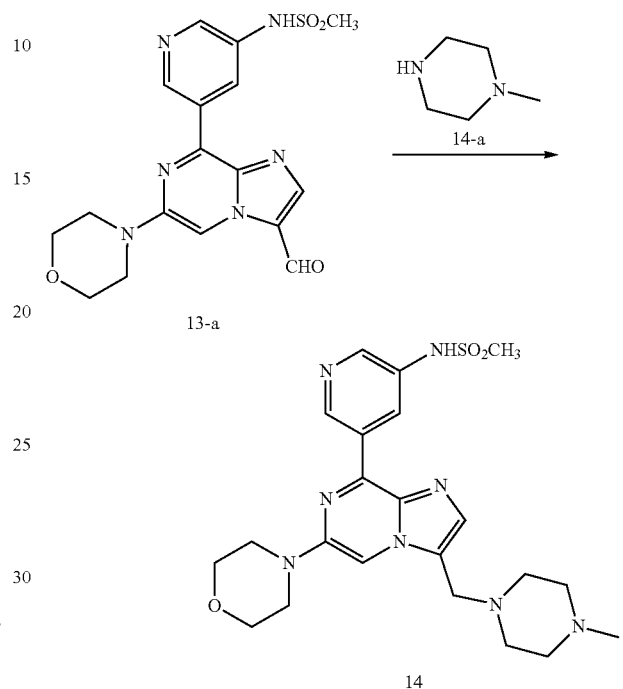

Synthesis of Compound 14

According to the process for preparing compound 12, compound 13-a and compound 14-a were used to give compound 14 (8 mg, 18%) which was yellow solid. LC-MS (ESI): m/z=487.2 (M+H)$^+$. $^1$H NMR (400 MHz, CDCl$_3$) δ 9.47 (d, 1H, J=1.6 Hz), 8.97 (d, 1H, J=1.6 Hz), 8.47 (d, 1H, J=2.4 Hz), 7.67 (s, 1H), 7.62 (s, 1H), 3.96 (t, 4H, J=4.4 Hz), 3.88 (s, 2H), 3.44 (t, 4H, J=4.4 Hz), 3.13 (s, 3H), 2.62 (brs, 8H), 2.42 (s, 3H).

Example 15

Synthesis of Compound 15

Synthesis Route of Compound 15

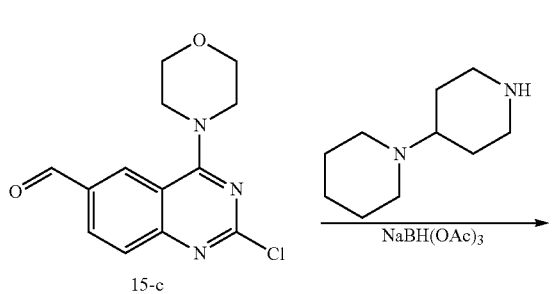

-continued

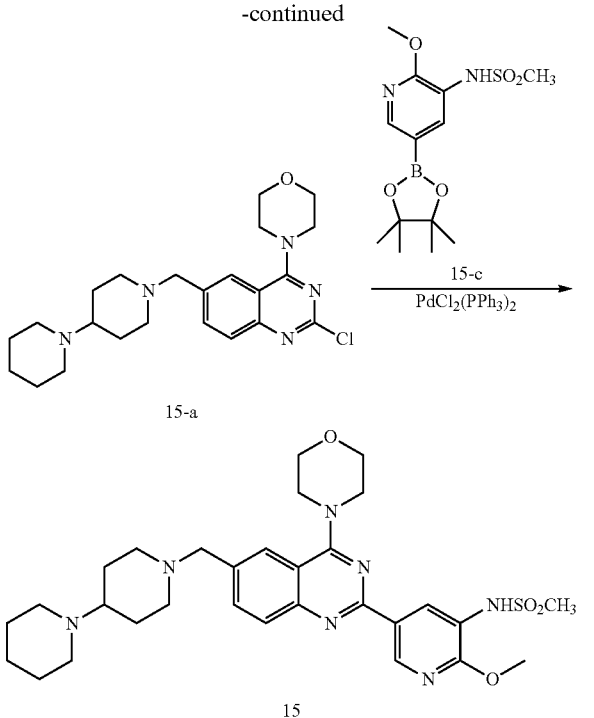

15-a

15

Synthesis of Compound 15-a

To a solution of compound 15-c (prepared according to the method disclosed in WO 2008/152387 A1) and 4-piperidyl piperidine (360 mg, 2.166 mmol) in dichloroethane (10 mL) was added acetic acid (0.1 mL), stirred for half an hour at room temperature, followed by adding sodium triacetoxyborohydride (459 mg, 2.166 mmol), and then stirred at room temperature overnight. The reaction solution was concentrated under reduced pressure, and the residue was purified with silica column chromatograph (elution system: dichloromethane/methanol=20/1) to give compound 15-a (80 mg, 34%). LC-MS (ESI): m/z=430.1 (M+H)$^+$.

Synthesis of Compound 15

A suspension of compound 15-a (95 mg, 0.221 mmol), compound 15-c (prepared according to the method disclosed in WO 2012/032067 A1) (90 mg, 0.274 mmol), sodium carbonate (60 mg, 0.566 mmol), dichlorobis(triphenylphosphine) palladium (12 mg, 0.017 mmol) in methylbenzene/ethanol/water (5 mL, 4/2/1) was heated to 125° C. by microwave under nitrogen gas atmosphere and stirred for 1 hour. The reaction solution was concentrated under reduced pressure, and the residue was purified by silica Preparative plate chromatograph (developing system: dichloromethane/methanol=20/1) to give product 15 (36 mg, 27%). LC-MS (ESI): m/z=596.3 (M+H)$^+$. $^1$H NMR (400 MHz, CDCl$_3$) δ 9.03 (d, J=2.0 Hz, 1H), 9.78 (d, J=2.0 Hz, 1H), 7.83 (d, J=8.4 Hz, 1H), 7.71 (s, 1H), 7.64 (dd, J$_1$=2.0 Hz, J$_2$=8.4 Hz, 1H), 4.02 (s, 3H), 3.85-3.87 (m, 4H), 3.76-3.79 (m, 4H), 3.54 (s, 2H), 3.00 (s, 3H), 2.86-2.89 (m, 2H), 2.42-2.44 (m, 4H), 2.16-2.24 (m, 1H), 1.92-1.97 (m, 2H), 1.70-1.74 (m, 2H), 1.48-1.57 (m, 6H), 1.35-1.37 (m, 2H).

Example 16

Synthesis of Compound 16

Synthesis Route of Compound 16

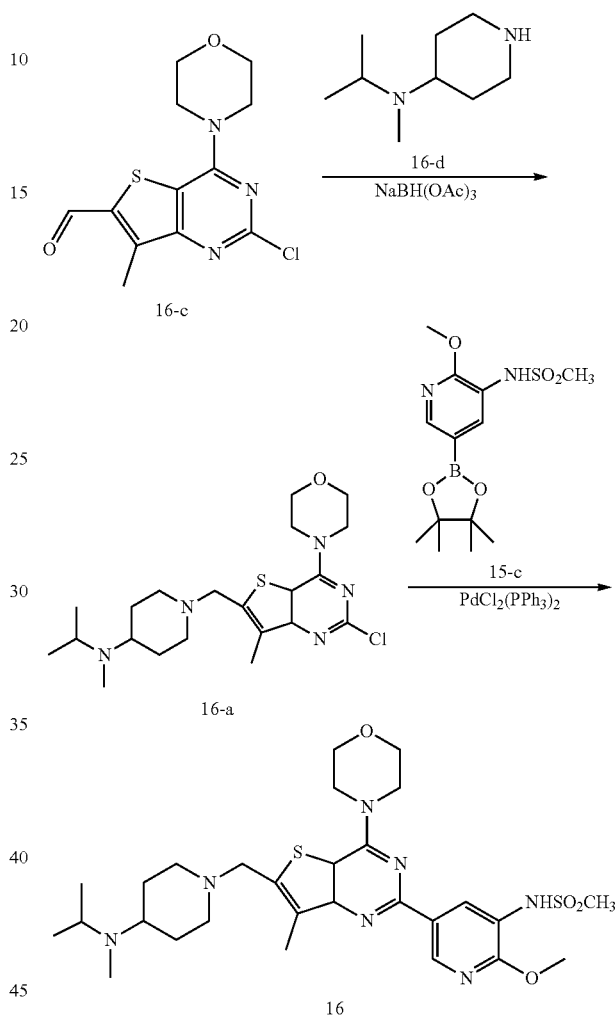

Synthesis of Compound 16-a

According to the process for preparing compound 15-a, compound 16-c (prepared according to the method disclosed in Journal of Medicinal Chemistry, 2011, No. 4, 615-619) and compound 16-d were used to give compound 16-a (82 mg, 56%) which was yellow solid. LC-MS (ESI): m/z=440.2 (M+H)$^+$.

Synthesis of Compound 16

According to the process for preparing compound 15, compound 16-a was used to give compound 16 (45 mg, 42%) which was yellow solid. LC-MS (ESI): m/z=604.3 (M+H)$^+$. $^1$H NMR (400 MHz, CDCl$_3$) δ 9.09 (d, 1H, J=2.0 Hz), 8.83 (d, 1H, J=2.0 Hz), 4.08 (s, 3H), 4.04 (t, 4H, J=4.4 Hz), 3.88 (t, 4H, J=4.4 Hz), 3.77 (s, 2H), 3.03 (s, 6H), 2.50-2.47 (m, 1H), 2.41 (s, 3H), 2.23 (s, 3H), 2.12 (t, 2H, J=9.6 Hz), 1.80 (d, 2H, J=11.2 Hz), 1.70 (dd, 2H, J=20.8, 11.2 Hz), 1.07 (d, 6H, J=6.4 Hz).

Example 17

Synthesis of Compound 17

Synthesis Route of Compound 17

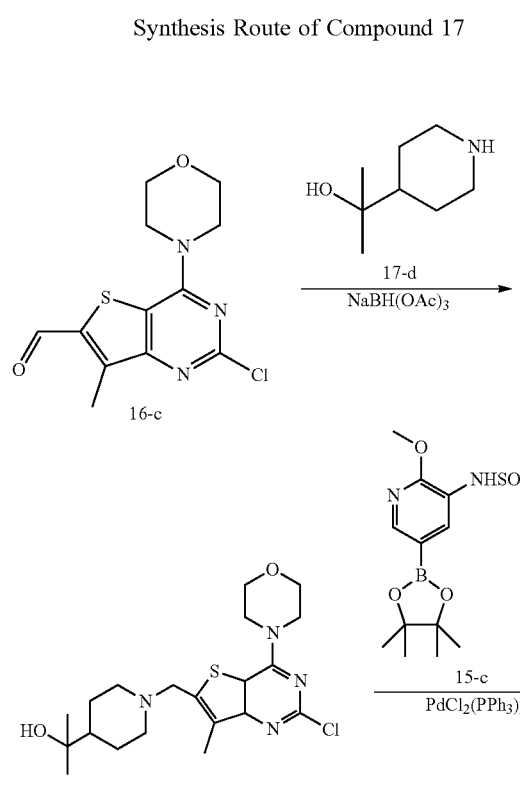

Example 18

Synthesis of Compound 18

Synthesis Route of Compound 18

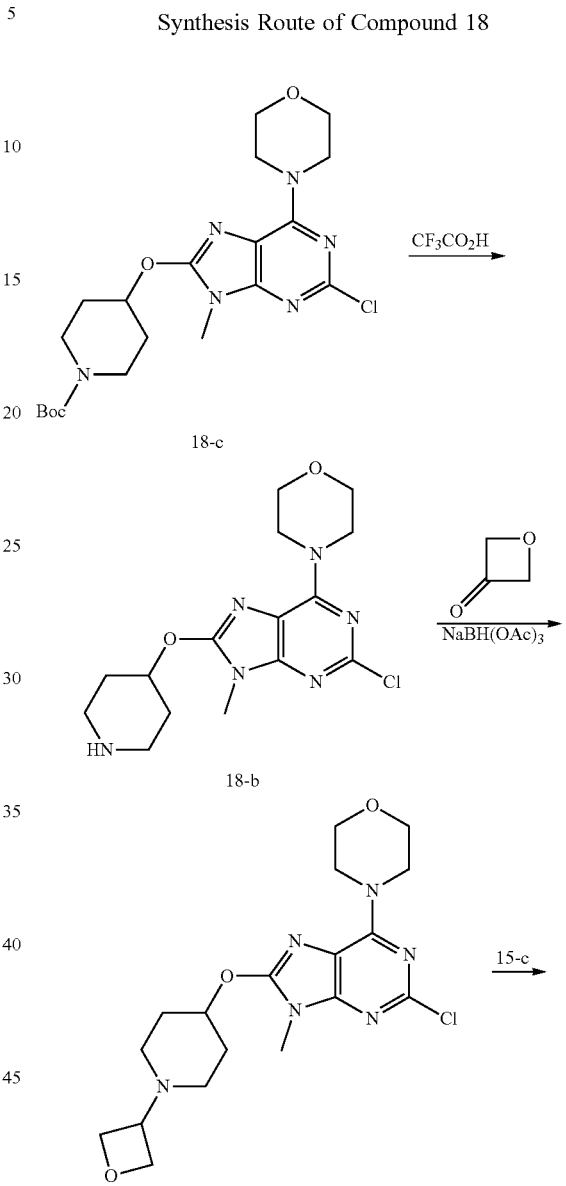

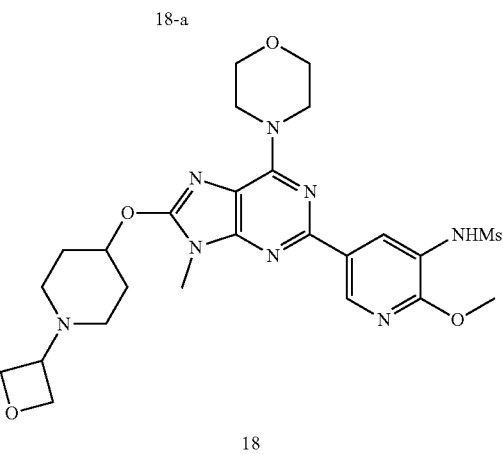

Synthesis of Compound 17-a

According to the process for preparing compound 15-a, compound 16-c and compound 17-d were used to give compound 17-a (450 mg, 74%) which was yellow solid. LC-MS (ESI): m/z=425.2 (M+H)$^+$.

Synthesis of Compound 17

According to the process for preparing compound 15, compound 17-a was used to give compound 17 (52 mg, 34%). LC-MS (ESI): m/z=591.3 (M+H)$^+$. $^1$H NMR (400 MHz, CDCl$_3$) δ 9.09 (d, 1H, J=2.0 Hz), 8.83 (d, 1H, J=2.0 Hz), 6.71 (s, 1H), 4.08 (s, 3H), 4.04 (t, 4H, J=4.4 Hz), 3.88 (t, 4H, J=4.4 Hz), 3.78 (s, 2H), 3.08 (bs, 2H), 3.03 (s, 3H), 2.43 (s, 3H), 2.05 (bs, 2H), 1.77 (d, 2H, J=12.0 Hz), 1.45 (bs, 2H), 1.35-1.31 (m, 1H), 1.24 (s, 1H), 1.20 (s, 6H).

Synthesis of Compound 18-b

To a solution of compound 18-c (prepared according to the method disclosed in US 2012/015931A1) (120 mg, 0.27 mmol) in dichloromethane (7 mL) was added dropwise trifluoroacetic acid (7 mL), and reacted for 3 hours at room temperature. The reaction solution was concentrated under reduced pressure, and the residue was partitioned between water and ethyl acetate. The organic layer was concentrated under reduced pressure to give compound 18-b (93 mg, 100%). LC-MS (ESI): m/z=353.1 (M+H).

Synthesis of Compound 18-a

To a solution of compound 18-b (93 mg, 0.26 mmol) and 3-oxetanone (19 mg, 0.26 mmol) in dichloroethane (10 mL) was added acetic acid (0.05 mL), stirred for 10 minutes at room temperature, followed by adding sodium triacetoxyborohydride (275 mg, 1.3 mmol), and stirred overnight at room temperature. The reaction solution was concentrated under reduced pressure, and the residue was purified by silica column chromatograph (elution system: petroleum ether/ethyl acetate=20/1) to give compound 18-a (82 mg, 76.6%). LC-MS (ESI): m/z=409.2 (M+H)$^+$.

Synthesis of Compound 18

According to the process for preparing compound 15, compound 18-a was used to give compound 18 (52 mg, 65.4%). LC-MS (ESI): m/z=575.2 (M+H)$^+$. $^1$H NMR (400 MHz, CDCl$_3$) δ 8.99 (1H, d, J=1.6 Hz), 8.74 (1H, d, J=2.0 Hz), 6.71 (1H, s), 5.15 (1H, t, J=3.6 Hz), 4.71-4.63 (4H, m), 4.21 (4H, d, J=4.0 Hz), 4.08 (3H, s), 3.84 (4H, t, J=4.4 Hz), 3.59 (3H, s), 3.57-3.52 (1H, m), 3.03 (3H, s), 2.56 (2H, s), 2.28 (2H, d, J=8.0 Hz), 2.17-2.12 (2H, m), 2.02-1.96 (2H, m).

Example 19

Synthesis of Compound 19

Synthesis Route of Compound 19

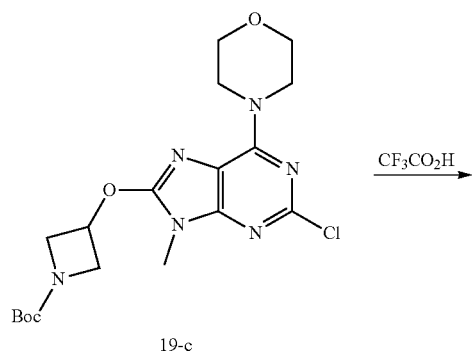

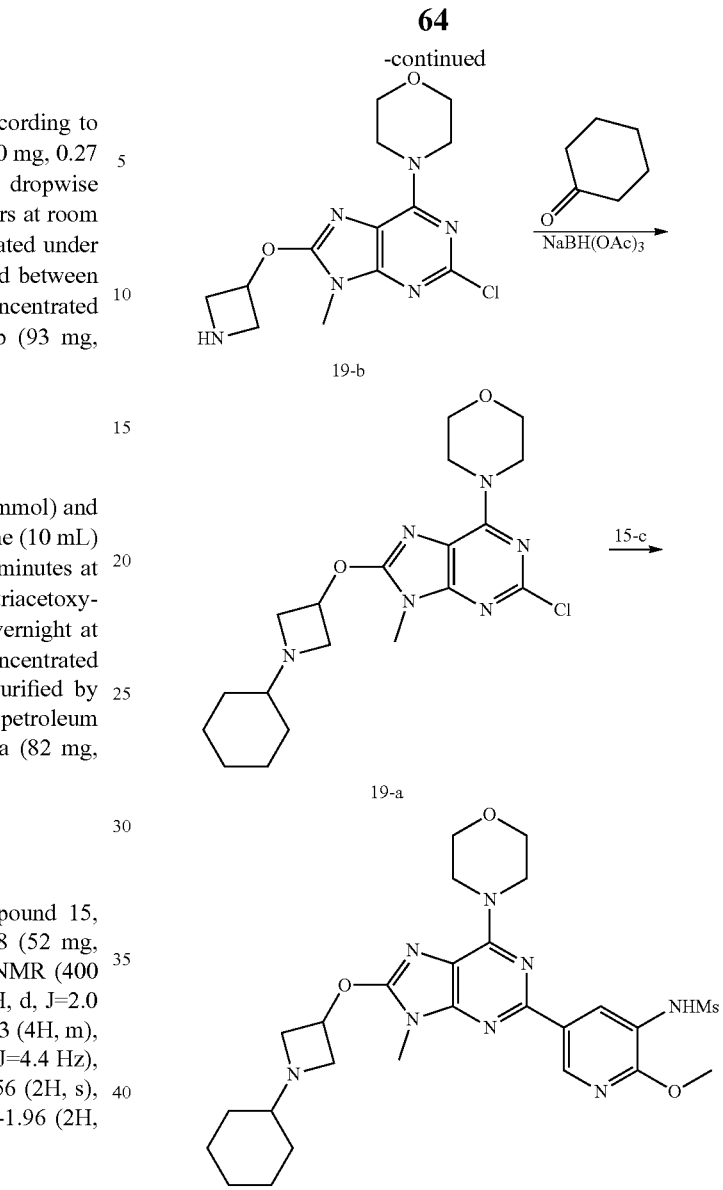

Synthesis of Compound 19-b

According to the process for preparing compound 19-b, compound 19-c (prepared according to the method disclosed in US 2012/015931A1) was used to give compound 19-b (456 mg, 95%). LC-MS (ESI): m/z=325.1 (M+H)$^+$.

Synthesis of Compound 19-a

According to the process for preparing compound 18-a, compound 19-b and cyclohexanone were used to give compound 19-a (115 mg, 92%). LC-MS (ESI): m/z=407.2 (M+H)$^+$.

Synthesis of Compound 19

According to the process for preparing compound 15, compound 19-a was used to give compound 19 (20 mg, 17.4%). LC-MS (ESI): m/z=573.2 (M+H)$^+$. $^1$H NMR (400 MHz, CDCl$_3$) δ 8.98 (1H, d, J=2.0 Hz), 8.74 (1H, d, J=2.0

Hz), 5.36 (1H, t, J=5.6 Hz), 4.21 (4H, d, J=4.0 Hz), 4.07 (3H, s), 3.84-3.81 (6H, m), 3.61 (3H, s), 3.21-3.17 (2H, m), 3.03 (3H, s), 2.11-2.05 (1H, m), 1.79-1.73 (6H, m), 1.31-1.25 (4H, m).

Example 20

Synthesis of Compound 20

Synthesis Route of Compound 20

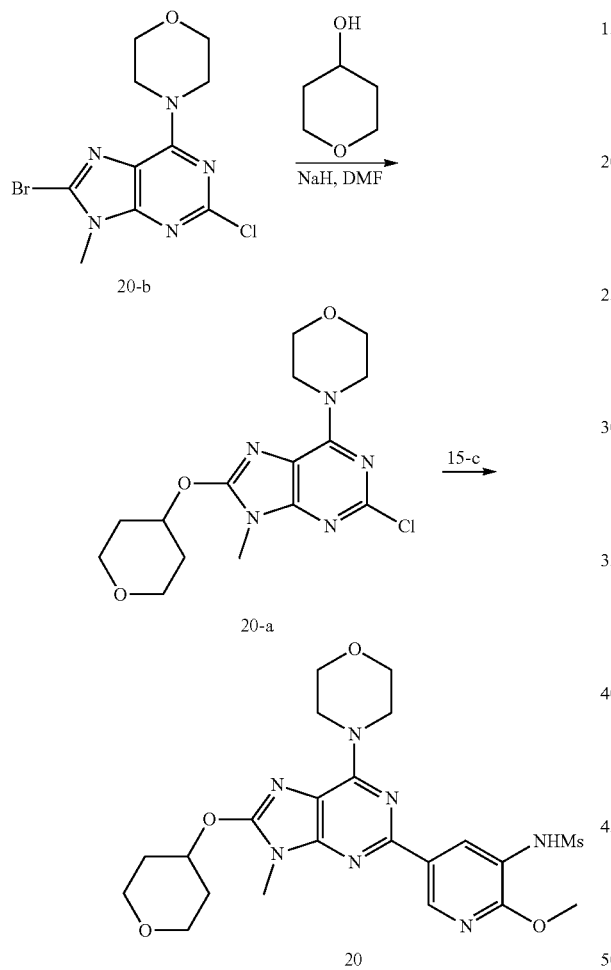

Synthesis of Compound 20-a

To a suspension of 60% sodium hydride (60 mg, 1.5 mmol) in THF (10 mL) was added dropwise a solution of 4-hydroxytetrahydropyran (45 mg, 0.36 mmol) in DMF (15 mL), stirred at room temperature for 1 hour, followed by adding dropwise a solution of compound 20-b (prepared according to the method in US 2012/015931A1) (100 mg, 0.30 mmol) in DMF (15 mL), and stirred overnight at room temperature. The reaction mixture was quenched with water, and extracted with ethyl acetate (3×40 mL). The organic layers were combined, and concentrated under reduced pressure. The residue was separated and purified with silica column chromatograph (elution system: dichloromethane/methanol=30/1) to give compound 20-a (85 mg, 80.1%). LC-MS (ESI):m/z=354.1 (M+H)⁺.

Synthesis of Compound 20

According to the process for preparing compound 15, compound 20-a was used to give compound 20 (30 mg, 24%). LC-MS (ESI): m/z=520.2 (M+H)⁺. ¹H NMR (400 MHz, CDCl₃) δ 8.99 (1H, d, J=2.0 Hz), 8.75 (1H, d, J=2.0 Hz), 6.71 (1H, s), 5.26 (1H, t, J=4.0 Hz), 4.22 (4H, t, J=4.8 Hz), 4.08 (3H, s), 4.03-3.98 (2H, m), 3.85 (4H, t, J=4.8 Hz), 3.69-3.63 (2H, m), 3.61 (3H, s), 3.03 (3H, s), 2.19-2.14 (2H, m), 1.94-1.89 (2H, m).

Example 21

Synthesis of Compound 21

Synthesis Route of Compound 21

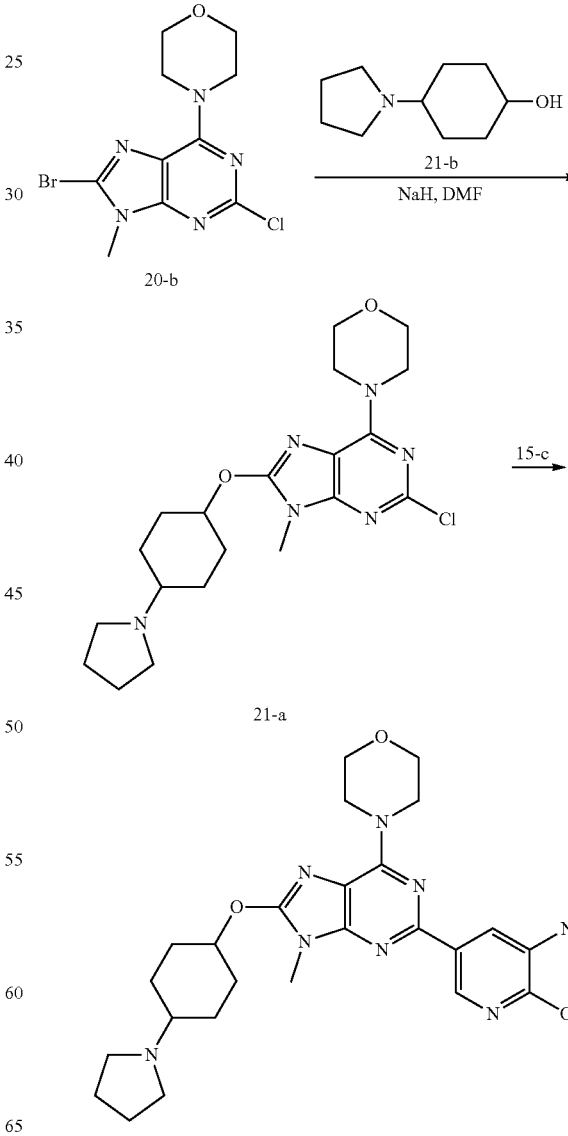

Synthesis of Compound 21-a

According to the process for preparing compound 20-a, compound 21-b was used to give compound 21-a (20 mg, 24%). LC-MS (ESI): m/z=421.2 (M+H)+.

Synthesis of Compound 21

According to the process for preparing compound 15, compound 21-a was used to give compound 21 (10 mg, 16%). LC-MS (ESI): m/z=587.3 (M+H)+. $^1$H NMR (400 MHz, CDCl$_3$) δ 8.99 (1H, d, J=2.0 Hz), 8.73 (1H, d, J=2.0 Hz), 6.71 (1H, s), 5.34 (1H, s), 4.21 (4H, t, J=4.8 Hz), 4.08 (3H, s), 3.83 (5H, t, J=4.8 Hz), 3.72 (3H, s), 3.04 (3H, s), 2.44-2.13 (12H, m), 1.90-1.88 (1H, m), 1.30-1.26 (3H, m).

Example 22

Synthesis of Compound 22

Synthesis Route of Compound 22

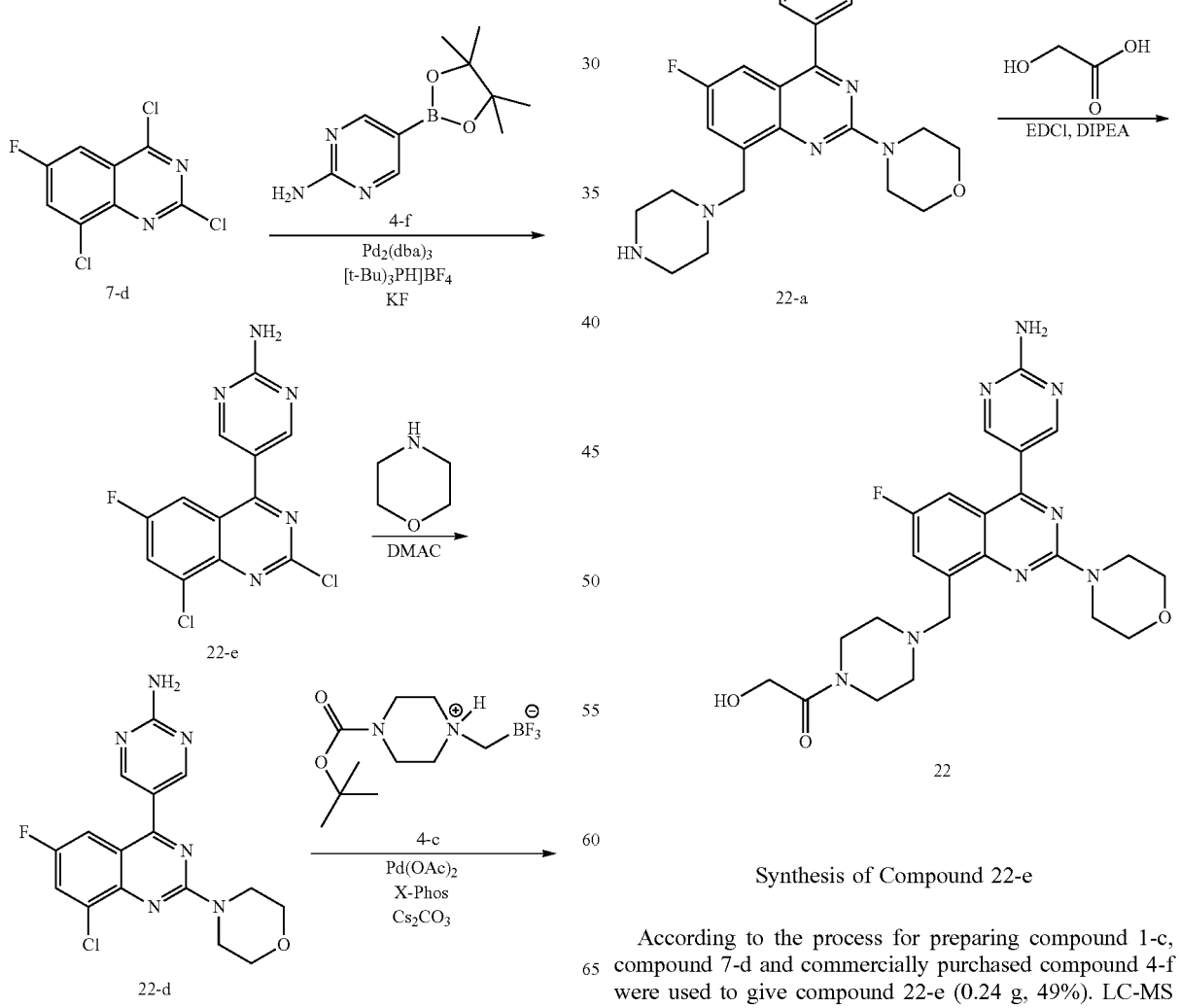

Synthesis of Compound 22-e

According to the process for preparing compound 1-c, compound 7-d and commercially purchased compound 4-f were used to give compound 22-e (0.24 g, 49%). LC-MS (ESI): m/z=310.0 (M+H)+.

Synthesis of Compound 22-d

According to the process for preparing compound 4-d, compound 22-e was used to give compound 22-d (0.27 g, 97%). LC-MS (ESI): m/z=361.1 (M+H)$^+$.

Synthesis of Compound 22-b

According to the process for preparing compound 1, compound 22-d and compound 4-c were used to give compound 22-b (195 mg, 71%). LC-MS (ESI): m/z=525.3 (M+H)$^+$.

Synthesis of Compound 22-a

According to the process for preparing compound 4-a, compound 22-b was used to give compound 22-a (150 mg, 95%). LC-MS (ESI): m/z=425.2 (M+H)$^+$.

Synthesis of Compound 22

According to the process for preparing compound 4, compound 22-a and glycolic acid were used to give compound 22 (25 mg, 44%). LC-MS (ESI): m/z=483.1 (M+H)$^+$. $^1$H NMR (400 MHz, CDCl$_3$) δ8.73 (2H, s), 7.67-7.64 (1H, m), 7.41-7.37 (1H, m), 5.38 (2H, s), 4.10 (2H, d, J=3.6 Hz), 4.06 (2H, s), 3.95-3.91 (4H, m), 3.84-3.81 (4H, m), 3.75-3.72 (2H, m), 3.64 (1H, t, J=4.8 Hz), 3.63-3.58 (4H, m).

Example 23

Synthesis of Compound 23

Synthesis Route of Compound 23

Synthesis of Compound 23-a

According to the process for preparing compound 1-f, commercially purchased compound 23-b was used to give compound 23-a (420 mg, 76%) which was white solid.

Synthesis of Compound 23

According to the process for preparing compound 1, compound 23-a and compound 7-a were used to give compound 23 (34 mg, 50.7%). LC-MS (ESI): m/z=628.1 (M+H)$^+$. $^1$H NMR (400 MHz, CDCl$_3$) δ 8.33 (d, J=2.0 Hz, 1H), 8.17 (d, J=2.0 Hz, 1H), 7.66 (d, J=8.8 Hz, 1H), 7.36-7.39 (m, 1H), 4.58-4.64 (m, 1H), 4.12 (s, 3H), 4.02 (s, 2H), 3.93-3.98 (m, 4H), 3.82-3.85 (m, 4H), 3.22-3.25 (m, 2H), 3.03-3.07 (m, 5H), 2.40-2.43 (m, 2H), 2.34 (t, J=11.6 Hz, 2H), 1.76-1.87 (m, 6H), 1.55-1.71 (m, 2H).

Example 24

Synthesis of Compound 24

Synthesis Route of Compound 24

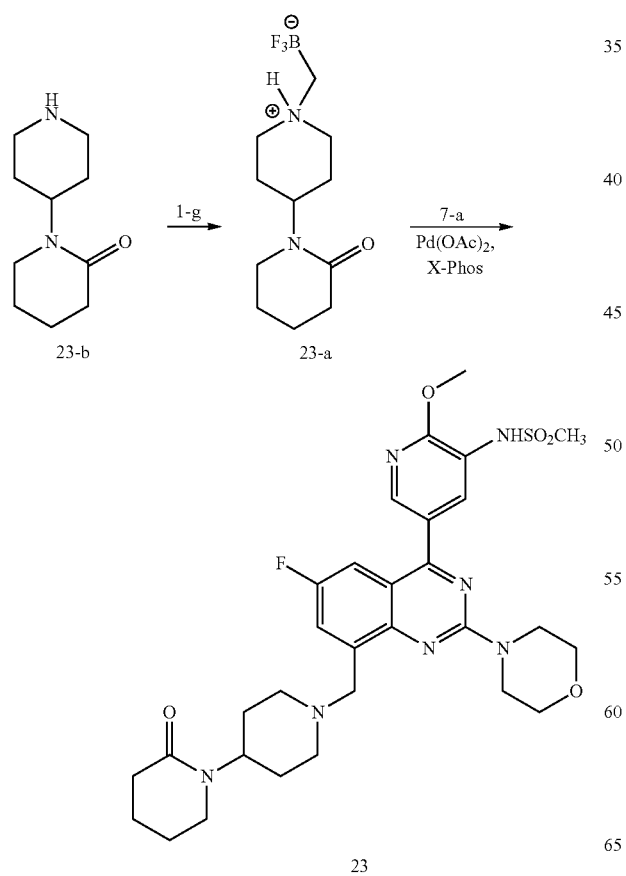

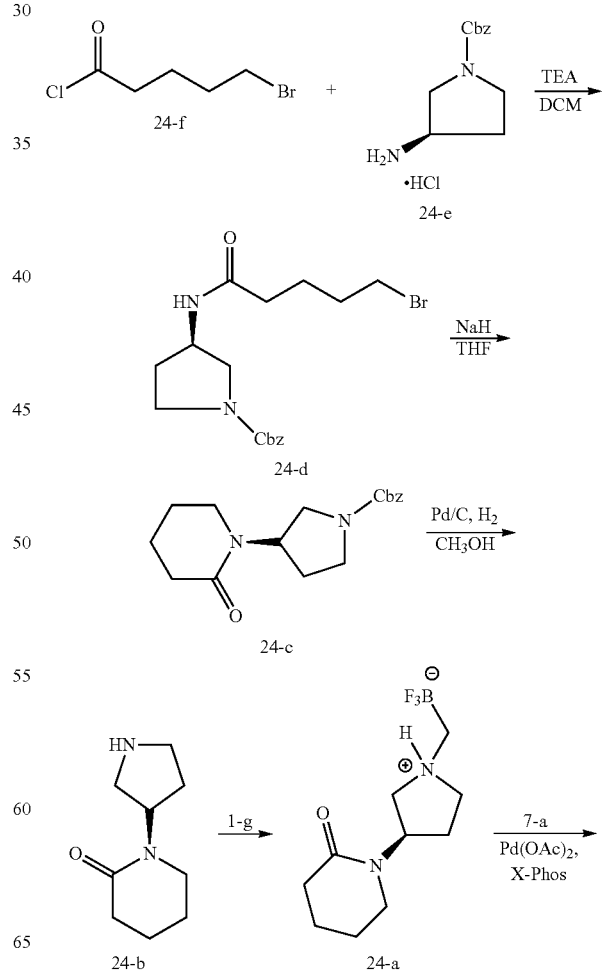

-continued

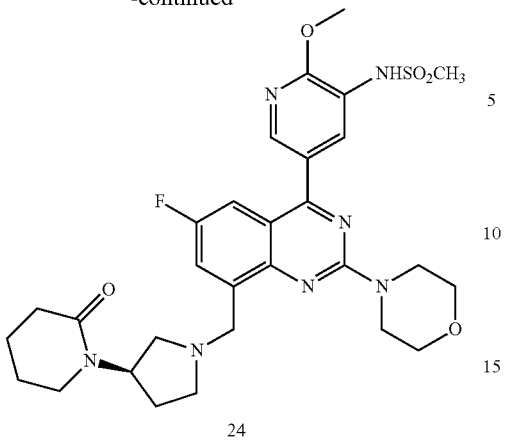

24

Synthesis of Compound 24-d

To a solution of commercially purchased compound 24-e (2.0 g, 7.8 mmol) and triethylamine (2.37 g, 23.4 mmol) in dichloromethane (150 mL) was added slowly commercially purchased compound 24-f (1.556 g, 7.8 mmol), and the reaction solution was stirred overnight at room temperature. To the solution was added water (50 mL), followed by washing the organic phase with 5% citric acid (80 mL×2). The organic layer was dried over anhydrous sodium sulphate, filtrated, and concentrated to give crude product 24-d (2.8 g, 93.8%), and the crude product was used directly for the next reaction without purification. LC-MS (ESI): m/z=383.1 (M+H)$^+$.

Synthesis of Compound 24-c

A solution of compound 24-d (2.8 g, 7.8 mmol) in THF (30 mL) was cooled with an ice bath, followed by slowly adding NaH (936 mg, 23.4 mmol). The reaction solution was stirred overnight at 80° C. under reflux. The reaction solution was diluted with water (60 mL), and the aqueous phase was extracted with ethyl acetate (80 mL×2). The organic layers were combined, dried over anhydrous sodium sulphate, filtrated, concentrated to give crude product, and then separated with silica plate chromatograph (CH$_2$Cl$_2$/CH$_3$OH=30:1) to give compound 24-c (1.85 g, 83.3%).

Synthesis of Compound 24-b

To a solution of compound 24-c (1.0 g, 3.30 mmol) in methanol (35 mL) was added slowly Pd/C (200 mg), and the reaction solution was stirred overnight under hydrogen gas atmosphere at room temperature. The reaction solution was diluted with ethyl acetate (60 mL), and filtrated to remove Pd/C. The filtrate was concentrated to give crude product 24-b (554 mg, 100%) which was used directly for the next reaction without purification.

Synthesis of Compound 24-a

According to the process for preparing compound 1-f, compound 24-b was used to give compound 24-a (850 mg, 73%).

Synthesis of Compound 24

According to the process for preparing compound 1, compound 24-a and compound 7-a were used to give compound 24 (35 mg, 53.4%). LC-MS (ESI): m/z=614.2 (M+H)$^+$. $^1$H NMR (400 MHz, CDCl$_3$) δ 8.26 (d, J=2.0 Hz, 1H), 8.10 (d, J=2.0 Hz, 1H), 7.55 (d, J=8.0 Hz, 1H), 7.31 (d, J=8.8 Hz, 1H), 5.33 (s, 1H), 4.05 (brs, 5H), 3.92-3.94 (m, 4H), 3.75-3.77 (m, 4H), 3.32-3.42 (m, 2H), 2.91-3.01 (m, 4H), 2.72-2.77 (m, 1H), 2.57-2.62 (m, 1H), 2.34 (t, J=6.4 Hz, 3H), 2.10-2.16 (m, 1H), 1.64-1.74 (m, 5H), 1.55 (brs, 1H).

Example 25

Synthesis of Compound 25

Synthesis Route of Compound 25

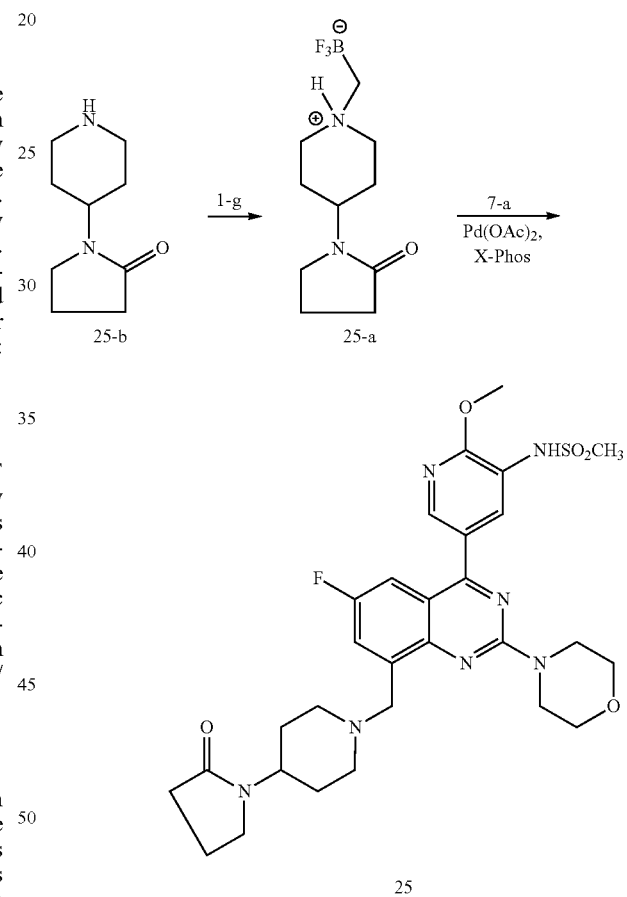

25

Synthesis of Compound 25-a

According to the process for preparing compound 1-f, commercially purchased compound 25-b was used to give compound 25-a (180 mg, 65%).

Synthesis of Compound 25

According to the process for preparing compound 1, commercially purchased compound 25-a and compound 7-a were used to give compound 25 (22 mg, 37.4%). LC-MS (ESI): m/z=613.7 (M+H)+. ¹H NMR (400 MHz, CDCl₃) δ 8.33 (s, 1H), 8.17 (s, 1H), 7.66 (d, J=8.4 Hz, 1H), 7.35-7.38 (m, 1H), 5.50 (d, J=7.6 Hz, 1H), 4.12 (s, 3H), 4.01 (s, 2H), 3.87-3.94 (m, 4H), 3.71-3.84 (m, 4H), 3.07 (s, 3H), 2.94 (d, J=11.2 Hz, 2H), 2.33 (t, J=11.6 Hz, 2H), 1.98 (d, J=11.2 Hz, 2H), 1.48-1.66 (m, 4H), 1.26-1.34 (m, 1H), 0.96-0.97 (m, 2H), 0.72-0.75 (m, 2H).

Example 26

Synthesis of Compound 26

Synthesis Route of Compound 26

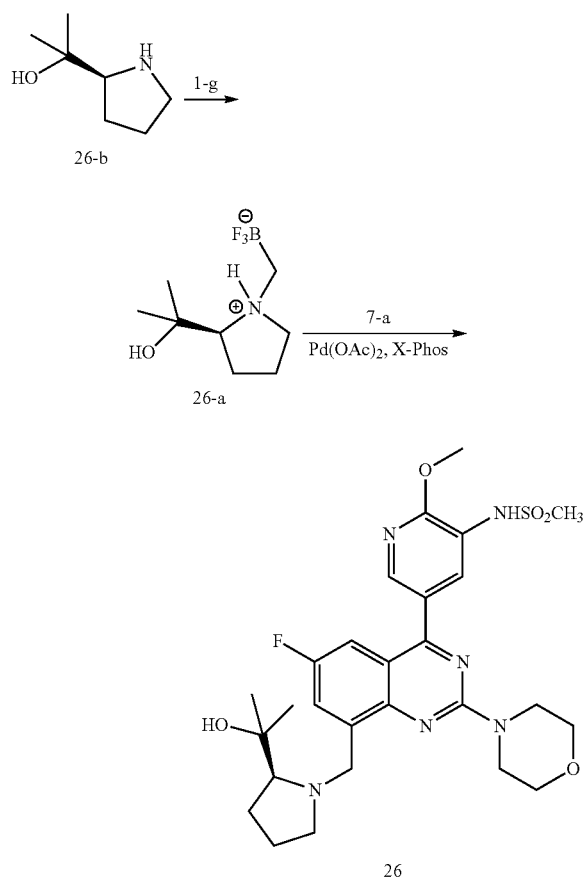

Synthesis of Compound 26-a

According to the process for preparing compound 1-f, commercially purchased compound 26-b was used to give compound 26-a (880 mg, 67%).

Synthesis of Compound 26

According to the process for preparing compound 1, compound 26-a and compound 7-a were used to give compound 26 (22 mg, 36.1%). LC-MS (ESI): m/z=575.1 (M+H)+. ¹H NMR (400 MHz, CDCl₃) δ 8.34 (d, J=2.0 Hz, 1H), 8.17 (d, J=2.0 Hz, 1H), 7.70 (d, J=7.6 Hz, 1H), 7.38 (d, J=8.8 Hz, 1H), 4.44-4.48 (m, 1H), 4.25-4.30 (m, 1H), 4.12 (s, 3H), 3.90-4.00 (m, 4H), 3.71-3.84 (m, 4H), 2.97-3.08 (m, 5H), 2.48 (s, 1H), 1.95-2.01 (m, 1H), 1.78 (s, 3H), 1.17-1.26 (m, 6H).

Example 27

Synthesis of Compound 27

Synthesis Route of Compound 27

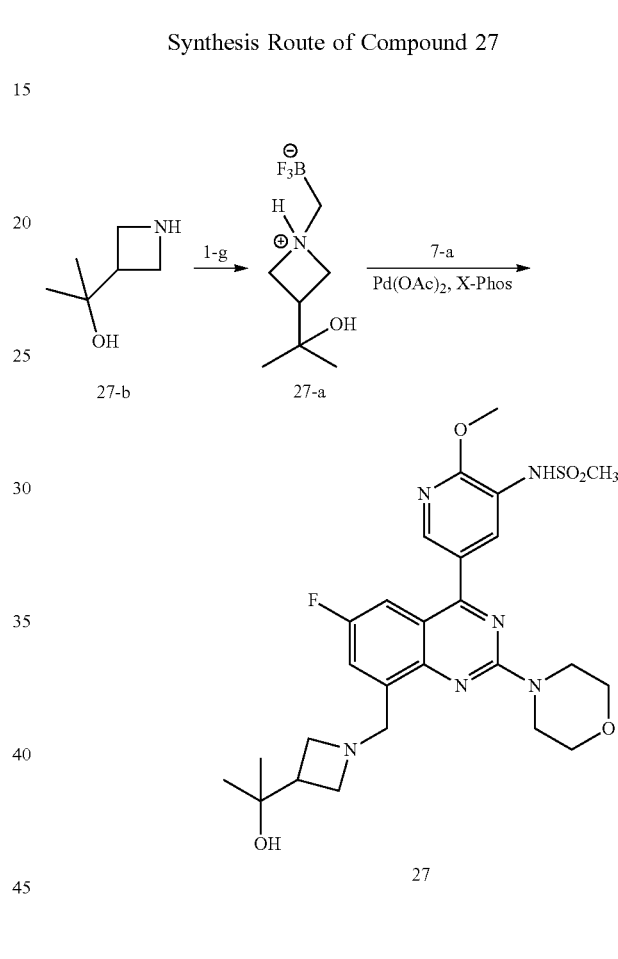

Synthesis of Compound 27-a

According to the process for preparing compound 1-f, commercially purchased compound 27-b was used to give compound 27-a (176 mg, 75%).

Synthesis of Compound 27

According to the process for preparing compound 1, compound 27-a and compound 7-a were used to give compound 27 (42 mg, 58%). LC-MS (ESI): m/z=561.2 (M+H)+. ¹H NMR (400 MHz, DMSO-d₆) δ 9.53 (s, 1H), 8.37 (d, 1H, J=2.0 Hz), 7.98 (d, 1H, J=2.4 Hz), 7.57 (dd, 1H, J=9.2, 2.4 Hz), 7.44 (dd, 1H, J=9.2, 2.8 Hz), 4.35 (s, 1H), 4.04 (s, 2H), 4.02 (s, 3H), 3.87 (t, 4H, J=4.8 Hz), 3.74 (t, 4H, J=5.2 Hz), 3.40 (t, 2H, J=7.2 Hz), 3.23 (t, 2H, J=7.2 Hz), 3.17 (d, 1H, J=4.8 Hz), 3.08 (s, 3H), 1.03 (s, 6H).

Example 28

Synthesis of Compound 28

Synthesis Route of Compound 28

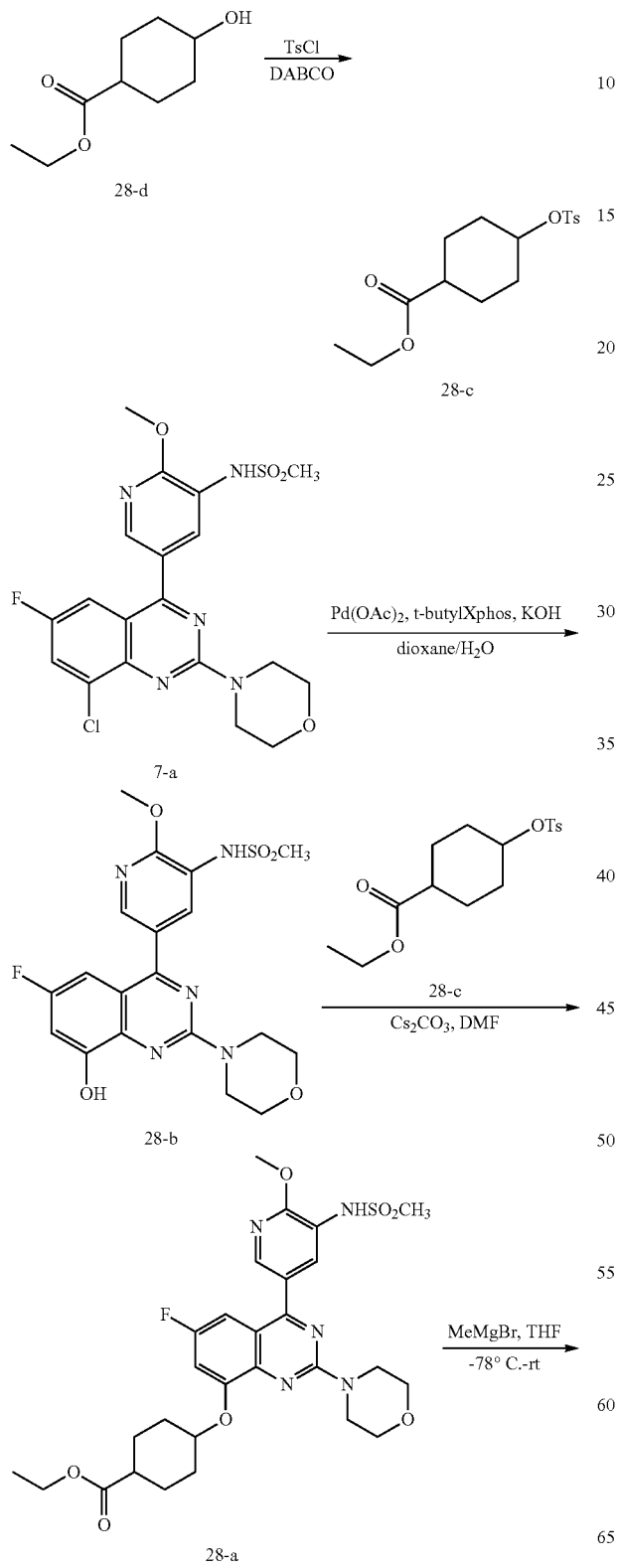

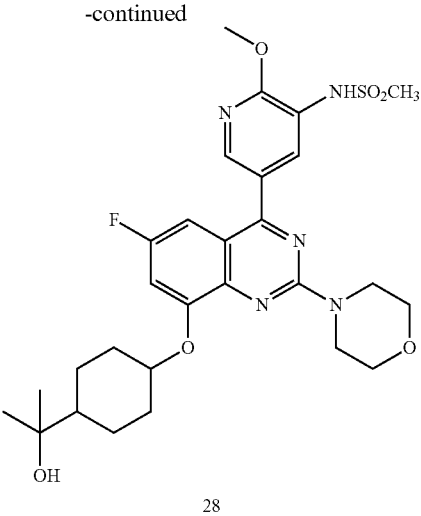

Synthesis of Compound 28-c

In an ice bath, to a solution of commercially purchased compound 28-d (1.72 g, 10 mmol) and DABCO (2.24 g, 20 mmol) in dichloromethane (30 mL) was added slowly TsCl (2.86 g, 15 mmol). The reaction solution was warmed to normal temperature and stirred for about 1 hour, followed by washing with 2N HCl solution (30 mL), water (30 mL) and saturated solution of sodium bicarbonate (30 mL) in sequence. The organic phase was dried over anhydrous sodium sulphate and concentrated. The crude product was purified with silica column chromatograph (petroleum ether/ethyl acetate=10/1-3/1) to give 28-c (2.94 g, 90%) which was white solid. LC-MS (ESI): m/z=344.1 $(M+NH_4)^+$.

Synthesis of Compound 28-b

To a microwave tube were added compound 7-a (200 mg, 0.43 mmol), $Pd_2(dba)_3$ (31 mg, 0.043 mmol), t-butylXPhos (78 mg, 0.185 mmol), potassium hydroxide (1.04 g, 18.5 mmol), 1,4-dioxane (8 mL) and water (5 mL), and stirred at 100° C. overnight under nitrogen gas atmosphere. The reaction solution was cooled to room temperature, acidified with 1N HCl solution, followed by neutralizing to pH>7 with saturated sodium bicarbonate solution. The mixture was extracted with dichloromethane (50*3 mL). The organic phases were combined, dried over anhydrous sodium sulphate, filtrated and concentrated. The crude product was separated and purified with silica column chromatograph (DCM/MeOH=10/1) to give compound 28-b (164 mg, 85%) which was yellow solid. LC-MS (ESI): m/z=450.0 $(M+H)^+$.

Synthesis of Compound 28-a

A solution of compound 28-c (89 mg, 0.275 mmol) and cesium carbonate (122 mg, 0.375 mmol) in DMF (4 mL) was stirred for 10 minutes at 80° C., followed by adding compound 28-b (112 mg, 0.25 mmol). The reaction solution was stirred overnight at 80° C. The reaction solution was quenched with water (20 mL), extracted with ethyl acetate (20 mL), and washed with saturated saline (3*20 mL). The organic phase was dried over anhydrous sodium sulphate, and concentrated. The crude product was separated and purified with silica Preparative plate chromatograph (DCM/

MeOH=10/1) to give compound 28-a (94 mg, 57%) which was yellow solid. LC-MS (ESI): m/z=604.1 (M+H)+.

Synthesis of Compound 28

At −78° C., to a solution of compound 28-a (94 mg, 0.16 mmol) in THF (4 mL) was added slowly 3.0 M methylmagnesium bromide (160 μL, 0.48 mmol). The reaction solution was warmed to normal temperature and stirred for about 2 hours. The reaction solution was quenched with saturated aqueous solution of ammonium chloride (5 mL), adjusted to pH>7 with saturated aqueous solution of sodium bicarbonate, and extracted with dichloromethane (3*10 mL). The organic phases were combined, washed with saturated saline (20 mL), dried over anhydrous sodium sulphate, filtrated, and concentrated. The crude product was separated and purified with silica Preparative plate thin layer chromatograph (DCM/MeOH=10/1) to give compound 28 (60 mg, 66%) which was yellow solid. LC-MS (ESI): m/z=590.2 (M+H)+. $^1$H NMR (400 MHz, CDCl$_3$): δ8.35 (t, 1H, J=2.0 Hz), 8.17 (d, 1H, J=2.0 Hz), 7.11-7.05 (m, 1H), 6.96-6.89 (m, 2H), 4.82-4.36 (m, 1H), 4.11 (s, 3H), 3.96 (t, 4H, J=4.4 Hz), 3.83-3.78 (m, 4H), 3.07 (s, 3H), 2.37 (d, 1H, J=10.4 Hz), 2.29 (d, 1H, J=14.0 Hz), 2.01 (d, 1H, J=12.8 Hz), 1.71-1.65 (m, 2H), 1.65-1.59 (m, 2H), 1.44-1.38 (m, 2H), 1.21 (s, 6H).

Example 29

Synthesis of Compound 29

Synthesis Route of Compound 29

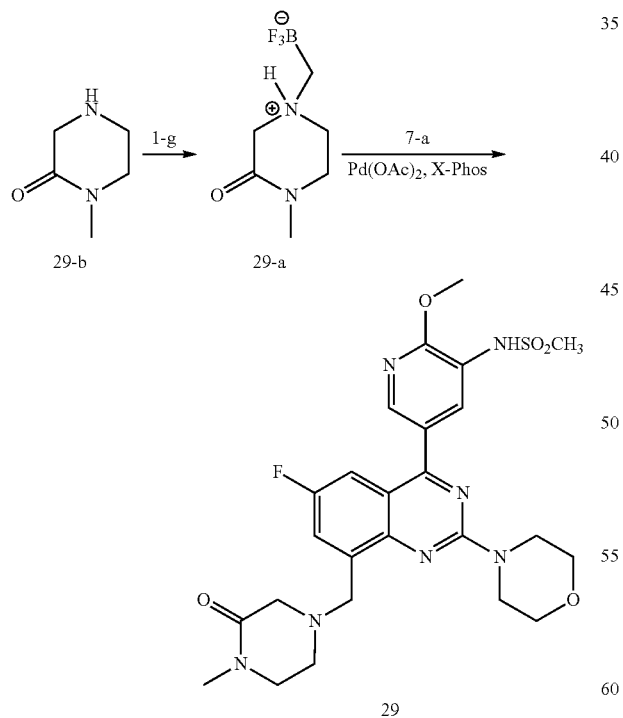

Synthesis of Compound 29-a

According to the process for preparing compound 1-f, commercially purchased compound 29-b was used to give compound 29-a (436 mg, 95%).

Synthesis of Compound 29

According to the process for preparing compound 1, compound 29-a and compound 7-a were used to give compound 29 (85 mg, 70%). LC-MS (ESI): m/z=560.2 (M+H)+. $^1$H NMR (400 MHz, CDCl$_3$): δ8.33 (d, 1H, J=2.0 Hz), 8.17 (d, 1H, J=2.0 Hz), 7.64 (dd, 1H, J=9.2, 2.8 Hz), 7.42 (dd, 1H, J=8.8, 3.2 Hz), 7.28 (s, 1H), 7.03 (s, 1H), 4.12 (s, 3H), 4.08 (s, 2H), 3.95 (t, 4H, J=5.2 Hz), 3.84 (t, 4H, J=5.2 Hz), 3.39 (t, 2H, J=5.2 Hz), 3.30 (s, 2H), 3.08 (s, 3H), 2.98 (s, 3H), 2.86 (t, 2H, J=5.2 Hz).

Example 30

Synthesis of Compound 30

Synthesis Route of Compound 30

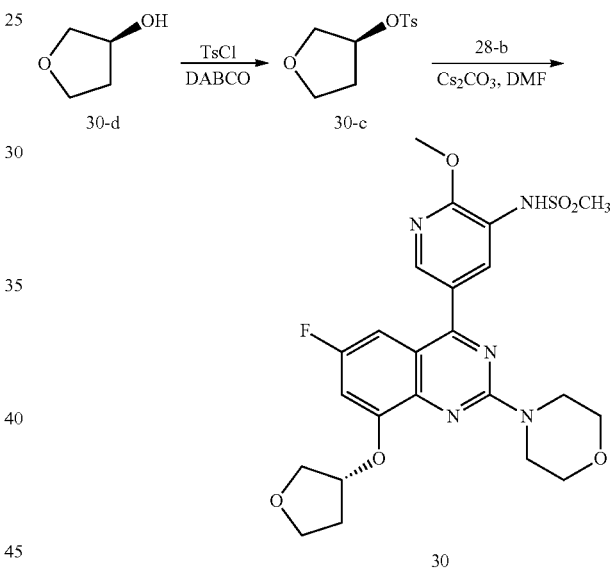

Synthesis of Compound 30-c

According to the process for preparing compound 28-c, commercially purchased compound 30-d was used to give compound 30-c (236 mg, 85%). LC-MS (ESI): m/z=260.0 (M+NH$_4$)+.

Synthesis of Compound 30

According to the process for preparing compound 28-a, compound 30-c was used to give compound 30 (25 mg, 22%). LC-MS (ESI): m/z=520.1 (M+H)+. $^1$H NMR (400 MHz, CDCl$_3$): δ8.34 (d, 1H, J=2.4 Hz), 8.18 (d, 1H, J=2.0 Hz), 7.14 (dd, 1H, J=9.2, 2.8 Hz), 6.86 (dd, 2H, J=10.4, 3.2 Hz), 5.18-5.17 (m, 1H), 4.18-4.07 (m, 6H), 3.99-3.94 (m, 5H), 3.83 (t, 4H, J=5.2 Hz), 3.07 (s, 3H), 2.33-2.28 (m, 2H).

Example 31

Synthesis of Compound 31

Synthesis Route of Compound 31

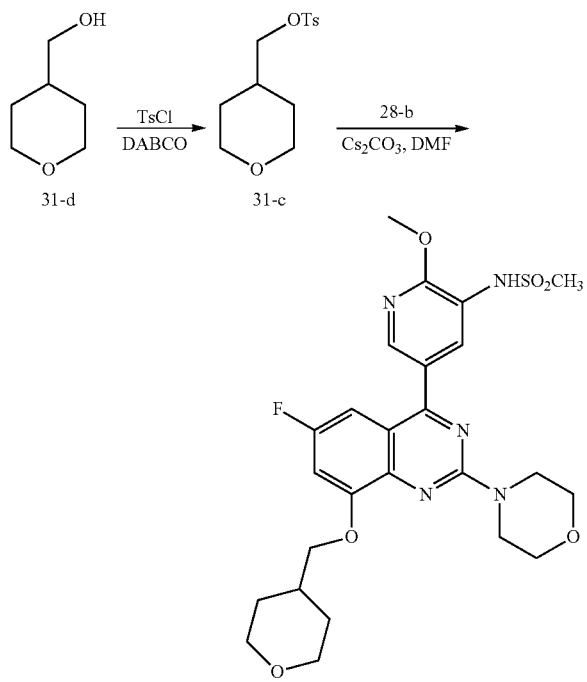

Synthesis of Compound 31-c

According to the process for preparing compound 28-c, commercially purchased compound 31-d was used to give compound 31-c (1.9 g, 91%). LC-MS (ESI): m/z=288.1 $(M+NH_4)^+$.

Synthesis of Compound 31

According to the process for preparing compound 28-a, compound 31-c was used to give compound 31 (65 mg, 54%). LC-MS (ESI): m/z=548.0 $(M+H)^+$. $^1$H NMR (400 MHz, CDCl$_3$): δ8.34 (d, 1H, J=2.4 Hz), 8.18 (d, 1H, J=2.0 Hz), 7.09 (dd, 1H, J=9.2, 2.4 Hz), 6.90 (s, 1H), 6.88 (dd, 1H, J=10.0, 2.4 Hz), 4.11 (s, 3H), 4.08 (dd, 2H, J=11.2, 3.2 Hz), 3.99 (d, 2H, J=6.4 Hz), 3.96 (t, 4H, J=4.0 Hz), 3.83 (t, 4H, J=4.4 Hz), 3.53-3.47 (m, 2H), 3.07 (s, 3H), 2.32-2.26 (m, 1H), 1.90 (d, 2H, J=12.8 Hz), 1.60-1.50 (m, 2H).

Example 32

Synthesis of Compound 32

Synthesis Route of Compound 32

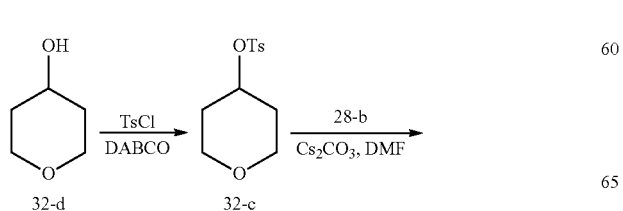

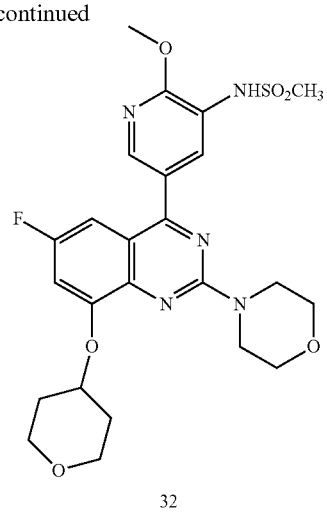

Synthesis of Compound 32-c

According to the process for preparing compound 28-c, commercially purchased compound 32-d was used to give compound 32-c (2.5 g, 98%). LC-MS (ESI): m/z=274.0 $(M+NH_4)^+$.

Synthesis of Compound 32

According to the process for preparing compound 28-a, compound 32-c was used to give compound 32 (60 mg, 51%). LC-MS (ESI): m/z=534.0 $(M+H)^+$. $^1$H NMR (400 MHz, CDCl$_3$): δ8.34 (d, 1H, J=1.6 Hz), 8.18 (d, 1H, J=2.4 Hz), 7.14 (dd, 1H, J=9.2, 2.4 Hz), 6.98 (dd, 1H, J=10.0, 2.4 Hz), 6.89 (s, 1H), 4.80-4.76 (m, 1H), 4.12 (s, 3H), 4.10-4.06 (m, 2H), 3.97 (t, 4H, J=4.4 Hz), 3.84 (t, 4H, J=4.0 Hz), 3.66-3.61 (m, 2H), 3.07 (s, 3H), 2.13-2.07 (m, 2H), 2.01-1.94 (m, 2H).

Example 33

Synthesis of Compound 33

Synthesis Route of Compound 33

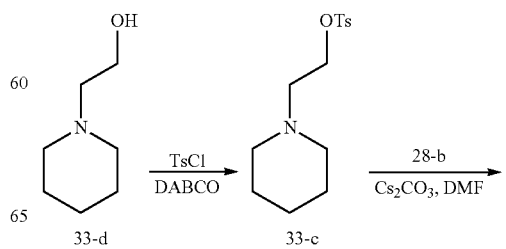

-continued

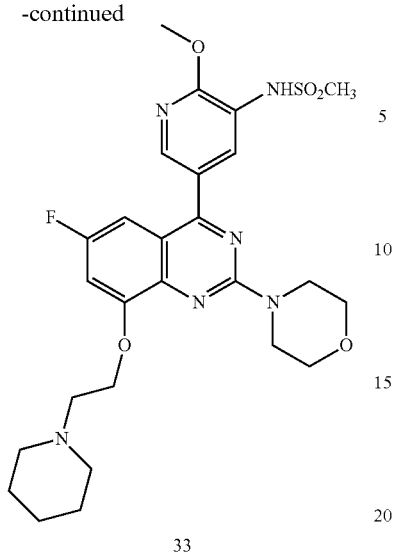

33

-continued

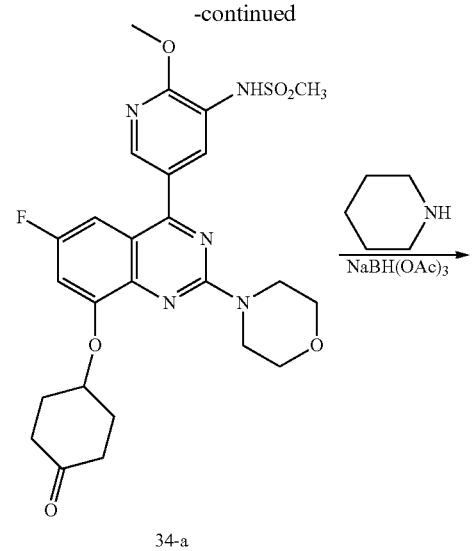

34-a

Synthesis of Compound 33-c

According to the process for preparing compound 28-c, commercially purchased compound 33-d was used to give compound 33-c (176 mg, 16%). LC-MS (ESI): m/z=284.1 (M+H)$^+$.

Synthesis of Compound 33

According to the process for preparing compound 28-a, compound 33-c was used to give compound 33 (25 mg, 22%). LC-MS (ESI): m/z=561.1 (M+H)$^+$. $^1$H NMR (400 MHz, CDCl$_3$): δ8.34 (d, 1H, J=2.0 Hz), 8.18 (d, 1H, J=2.4 Hz), 7.09 (dd, 1H, J=9.2, 2.4 Hz), 6.89 (dd, 1H, J=10.0, 2.4 Hz), 4.29 (t, 2H, J=6.0 Hz), 4.11 (s, 3H), 3.96 (t, 4H, J=4.4 Hz), 3.83 (t, 4H, J=4.4 Hz), 3.07 (s, 3H), 2.98 (t, 2H, J=5.6 Hz), 2.64 (bs, 4H), 1.66-1.60 (m, 4H), 1.48-1.46 (m, 2H).

Example 34

Synthesis of Compounds 34, 35, 36

Synthesis Route of Compounds 34, 35, 36

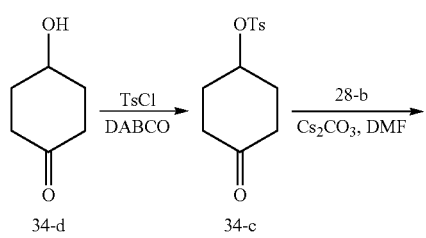

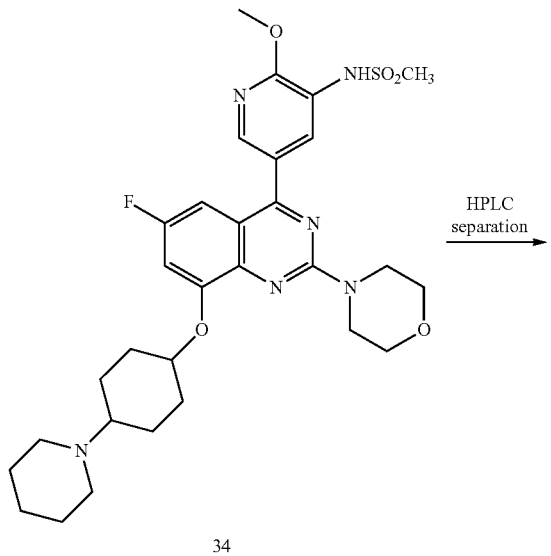

34

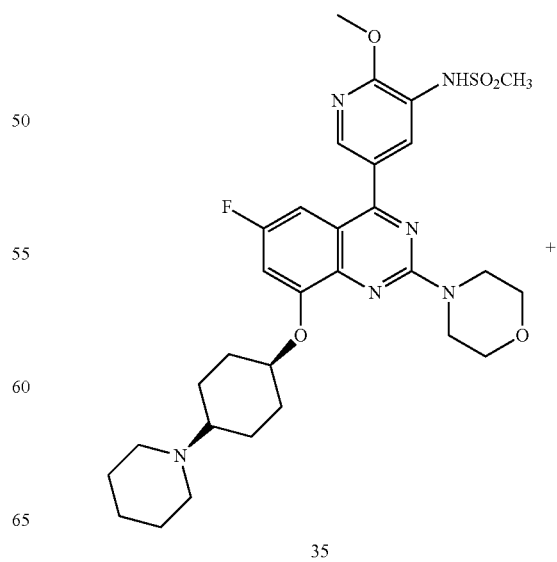

35

83

-continued

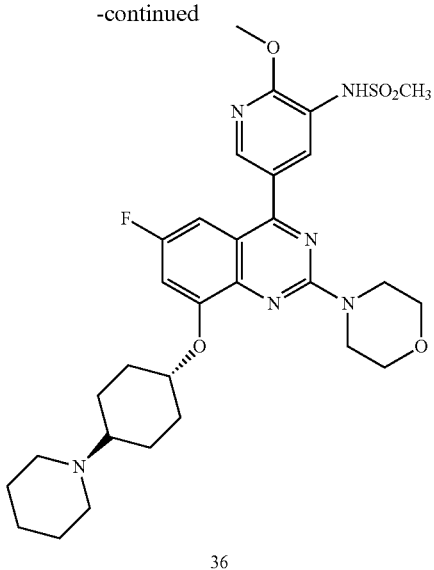

36

Synthesis of Compound 34-c

According to the process for preparing compound 28-c, commercially purchased compound 34-d was used to give compound 34-c (581 mg, 95%). LC-MS (ESI): m/z=286.0 (M+H)$^+$.

Synthesis of Compound 34-a

According to the process for preparing compound 28-a, compound 34-c was used to give compound 34-a (460 mg, 95%). LC-MS (ESI): m/z=546.3 (M+H)$^+$.

Synthesis of Compound 34

To a flask were added compound 34-a (460 mg, 0.84 mmol), piperidine (718 mg, 8.4 mmol), NaBH(OAc)$_3$ (1.78 g, 8.4 mmol), glacial acetic acid (5 mg, 0.084 mmol) and 1,2-dichloroethane (20 mL). The mixture was stirred overnight at 40° C., followed by adding water (15 mL) and extracted with dichloromethane (20 mL) for 3 times. The organic phases were combined, dried, and concentrated. The residue was purified with silica column chromatograph (CH$_2$Cl$_2$/CH$_3$OH=60/1 to 10/1) to give compound 34 (210 mg, 40.5%). LC-MS (ESI): m/z=615.1 (M+H)$^+$. $^1$H NMR (400 MHz, CDCl$_3$): 8.34 (t, J=2.4 Hz, 1H), 8.17 (d, J=2.1 Hz, 1H), 7.10 (m, 1H), 6.97-6.89 (m, 1H), 4.78 (s, 0.7H), 4.38 (dd, J=9.6, 5.4 Hz, 0.3H), 4.12 (s, 3H), 3.95 (dd, J=9.0, 3.8 Hz, 4H), 3.82 (dd, J=9.5, 4.6 Hz, 4H), 3.07 (s, 3H), 2.72-2.45 (m, 5H), 2.29 (d, J=14.9 Hz, 2H), 2.00 (t, J=12.8 Hz, 2H), 1.81-1.54 (m, 8H), 1.47 (dd, J=13.0, 7.8 Hz, 3H).

The cis/trans mixture of compound 34 was separated with preparative supercritical fluid chromatography (apparatus: SFC-80 (Thar, Waters); column: RegisCell, 30*250 mm, 5 μm; mobile phase: CO$_2$/Methanol (0.1% NH$_4$OH)=65/35; flow rate: 80 g/min; Back pressure: 100 bar) to give compound 35 (with a relatively short retention time) and compound 36 (with a relatively long retention time). The isomers were characterized by 1H-NMR.

Compound 35: LC-MS (ESI): m/z=615.3 (M+H)$^+$. $^1$H NMR (400 MHz, CDCl$_3$): 8.34 (d, J=2.1 Hz, 1H), 8.17 (d, J=2.1 Hz, 1H), 7.08 (dd, J=9.2, 2.6 Hz, 1H), 6.92 (dd, J=10.4, 2.6 Hz, 1H), 4.77 (s, 1H), 4.12 (s, 3H), 4.00-3.92 (m, 4H), 3.85-3.79 (m, 4H), 3.07 (s, 3H), 2.63-2.55 (m, 4H), 2.50 (s, 1H), 2.27 (d, J=14.7 Hz, 2H), 1.97 (dd, J=11.0, 8.4 Hz, 2H), 1.70 (d, J=10.3 Hz, 2H), 1.60 (dd, J=14.8, 9.7 Hz, 6H), 1.46 (d, J=5.2 Hz, 2H).

Compound 36: LC-MS (ESI): m/z=615.3 (M+H)$^+$. $^1$H NMR (400 MHz, CDCl$_3$): 8.34 (d, J=2.0 Hz, 1H), 8.17 (d, J=2.0 Hz, 1H), 7.10 (dd, J=9.2, 2.5 Hz, 1H), 6.94 (dd, J=10.2, 2.5 Hz, 1H), 4.37 (dd, J=9.6, 5.4 Hz, 1H), 4.12 (s, 3H), 3.97-3.91 (m, 4H), 3.85-3.79 (m, 4H), 3.07 (s, 3H), 2.57 (s, 4H), 2.43 (d, J=11.3 Hz, 1H), 2.34 (d, J=11.5 Hz, 2H), 2.10-1.99 (m, 2H), 1.64 (dd, J=15.8, 9.6 Hz, 6H), 1.46 (t, J=11.4 Hz, 4H).

Example 35

Synthesis of Compounds 37

Synthesis Route of Compounds 37

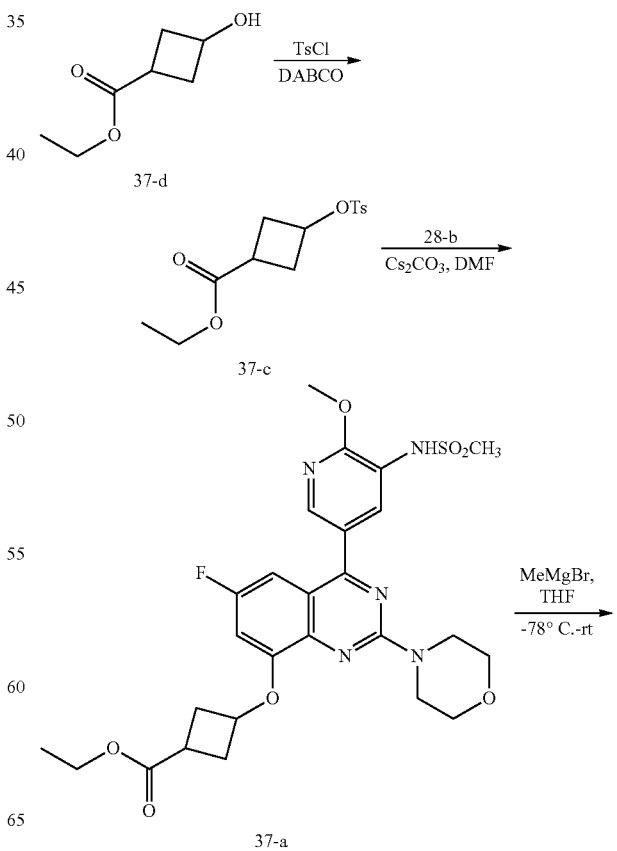

-continued

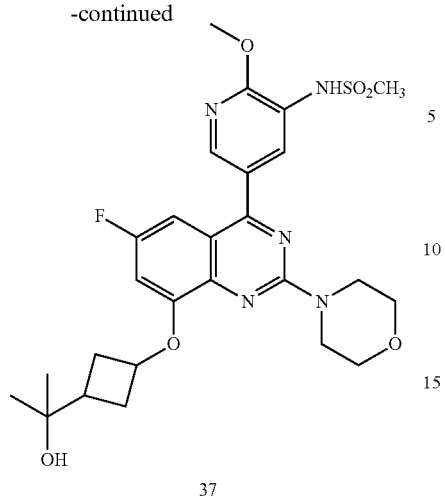

37

Synthesis of Compound 37-c

According to the process for preparing compound 28-c, commercially purchased compound 37-d was used to give compound 37-c (619 mg, 99%). LC-MS (ESI): m/z=316.0 (M+H)$^+$.

Synthesis of Compound 37-a

According to the process for preparing compound 28-a, compound 37-c was used to give compound 37-a (121 mg, 66%). LC-MS (ESI): m/z=576.0 (M+H)$^+$.

Synthesis of Compound 37

According to the process for preparing compound 28, compound 37-a was used to give compound 37 (7 mg, 6%). LC-MS (ESI): m/z=562.0 (M+H)$^+$. $^1$H NMR (400 MHz, CDCl$_3$): δ8.35 (d, J=2.1 Hz, 1H), 8.19 (d, J=2.1 Hz, 1H), 7.06 (dd, J=9.2, 2.5 Hz, 1H), 6.80 (s, 1H), 6.65 (dd, J=10.4, 2.5 Hz, 1H), 4.85 (s, 1H), 4.12 (s, 3H), 4.01-3.95 (m, 4H), 3.87-3.81 (m, 4H), 3.07 (s, 3H), 2.59-2.45 (m, 5H), 1.27 (s, 1H), 1.24 (s, 6H).

Example 36

Synthesis of Compounds 38

Synthesis Route of Compounds 38

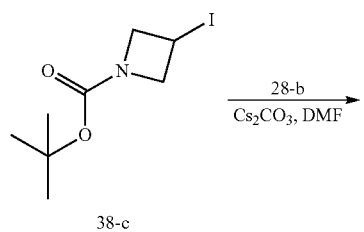

38-c

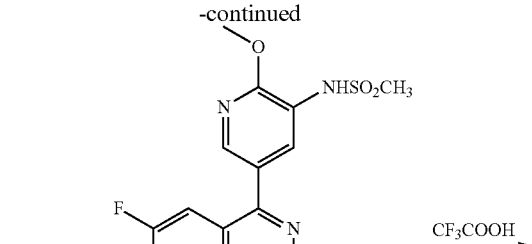

38-b

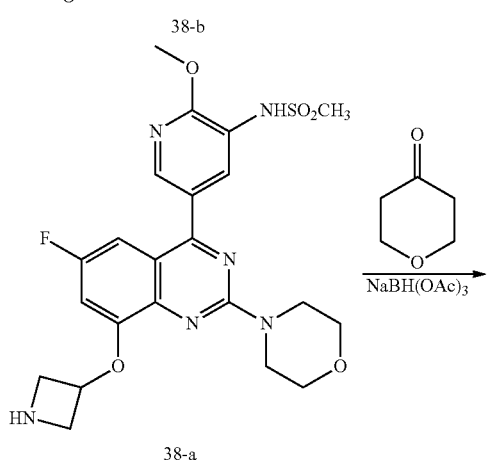

38-a

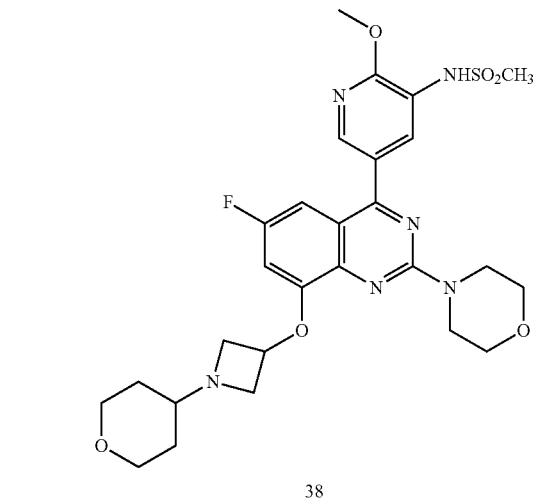

38

Synthesis of Compound 38-b

According to the process for preparing compound 28-a, commercially purchased compound 38-c was used to give compound 38-b (270 mg, 90.9%). LC-MS (ESI): m/z=605.0 (M+H)$^+$.

Synthesis of Compound 38-a

According to the process for preparing compound 4-a, compound 38-b was used to give compound 38-a (260 mg, 100%). LC-MS (ESI): m/z=505.0 (M+H)$^+$.

Synthesis of Compound 38

To a flask were added compound 38-a (67 mg, 0.13 mmol), tetrahydrofuran-4-one (26 mg, 0.26 mmol), NaBH(OAc)$_3$ (137 mg, 0.65 mmol), glacial acetic acid (0.5 mg) and 1,2-dichloroethane (30 mL). The mixture was stirred overnight at room temperature, followed by adding water (15 mL) and then extracted with dichloromethane (20 mL) for 3 times. The organic phases were combined, dried, and concentrated. The residue was separated and purified by Prep-HPLC to give compound 38 (10 mg, 12.3%). LC-MS (ESI): m/z=589.1 (M+H)$^+$. $^1$H NMR (400 MHz, CDCl$_3$): δ8.34 (1H, d, J=1.6 Hz), 8.18 (1H, d, J=2.4 Hz), 7.12-7.09 (1H, m), 6.67-6.64 (1H, m), 4.98 (1H, t, J=6.0 Hz), 4.12 (3H, s), 4.01-3.93 (8H, m), 3.83 (4H, t, J=4.4 Hz), 3.44-3.37 (2H, m), 3.32-3.29 (2H, m), 3.07 (3H, s), 2.44-2.39 (1H, m), 1.73-1.70 (2H, m), 1.45-1.35 (2H, m).

Example 37

Synthesis of Compounds 39

Synthesis Route of Compounds 39

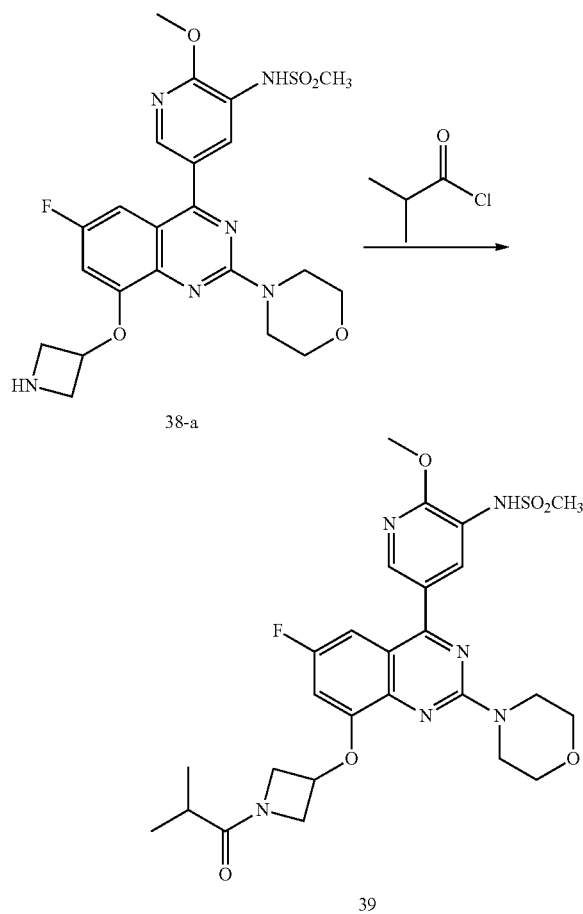

Synthesis of Compound 39

Compound 38-a (60 mg, 0.12 mmol) was dissolved in 20 mL dichloromethane, followed by adding triethylamine (37 mg, 0.36 mmol) and isobutyryl chloride (12 mg, 0.12 mmol). The reaction mixture was stirred for 30 minutes at room temperature, followed by adding water (15 mL) and then extracted with dichloromethane (20 mL) for 3 times. The organic phases were combined, dried, and concentrated. The residue was separated and purified by Prep-HPLC to give compound 39 (35 mg, 51.4%). LC-MS (ESI): m/z=575.0 (M+H)$^+$. $^1$H NMR (400 MHz, CDCl$_3$): δ6 8.35 (1H, d, J=2.4 Hz), 8.18 (1H, d, J=2.4 Hz), 7.18-7.15 (1H, m), 6.83 (1H, s), 6.60-6.57 (1H, m), 5.16-5.13 (1H, m), 4.65-4.61 (1H, m), 4.50-4.46 (1H, m), 4.42-4.39 (1H, m), 4.29-4.25 (1H, m), 4.13 (3H, s), 3.98 (4H, t, J=4.8 Hz), 3.83 (4H, t, J=4.8 Hz), 3.08 (3H, s), 2.53-2.46 (1H, m), 1.15-1.13 (6H, m).

Effect Example 1

PI3Kα, PI3Kδ, PI3Kβ and PI3Kγ Enzymatic Inhibitory Activity IC50 Assay

1. Buffer preparation: 50 mM HEPES, pH 7.5, 3 mM MgCl$_2$, 1 mM EGTA, 100 mM NaCl, 0.03% CHAPS.
2. The compound was formulated in 100% DMSO in a concentration gradient, and deposited to a 384-well plate with a final DMSO concentration of 1%.
3. PI3Kα, PI3Kδ, PI3Kβ and PI3Kγ enzymes (purchased from EMD Millipore) were diluted to the optimal concentration with the following buffer: 50 mM HEPES, pH 7.5, 3 mM MgCl$_2$, 1 mM EGTA, 100 mM NaCl, 0.03% CHAPS, 2 mM DTT, transferred to a 384-well plate and incubated with the compound for a certain time.
4. The substrate was diluted to an optimal concentration with the following buffer: 50 mM HEPES, pH 7.5, 3 mM MgCl$_2$, 1 mM EGTA, 100 mM NaCl, 0.03% CHAPS, 2 mM DTT, 50 μM PIP2, 25 μM ATP and added to the 384-well plate to initiate the reaction. PI3Kα, PI3Kβ and PI3Kγ were allowed to react for 1 h at room temperature, and PI3Kδ reacted for 2 hours at room temperature. Another 10 μL ADP-Glo Detection Reagent also needed to be added for PI3Kβ and PI3Kγ, and then equilibrated at room temperature for 30 minutes.
5. Luminescence was read by using Flexstation, and the inhibition rate was calculated as the average value of two tests.

Table 1 shows the IC$_{50}$ values against PI3Kδ of the compounds in the present invention and the ratio of IC$_{50}$ values against PI3Kα to PI3Kδ (referred to as α/δ). Table 2 shows the ratio of IC$_{50}$ values against PI3Kβ to PI3Kδ of partial compounds (referred to as β/δ) and the ratio of IC$_{50}$ values against PI3Kγ to PI3Kδ (referred to as γ/δ).

TABLE 1

| Compound No. | PI3Kδ IC50 (nM) | α/δ | Compound No. | PI3Kδ IC50 (nM) | α/δ |
|---|---|---|---|---|---|
| 1 | 7.6 | 341 | 2 | 17 | 368 |
| 3 | 31 | 119 | 4 | 45 | 2 |
| 5 | 58.6 | 1 | 6 | 457 | 2.4 |
| 7 | 31 | 130 | 8 | 9.8 | 292 |
| 9 | 19 | 233 | 10 | 6.4 | 320 |
| 11 | 606 | 2.3 | 12 | 241 | >41 |
| 13 | 239 | >42 | 14 | 1035 | >9 |
| 15 | 345 | 23 | 16 | 15 | 42 |
| 17 | 3.4 | 38 | 18 | 4.2 | 11 |
| 19 | 5 | 88 | 20 | 4.6 | 15 |
| 21 | 15.3 | 91 | 22 | 31 | 2 |
| 23 | 16 | 79 | 24 | 21 | 45 |
| 25 | 28 | 28 | 26 | 87 | 32 |

TABLE 1-continued

| Compound No. | PI3Kδ IC50 (nM) | α/δ | Compound No. | PI3Kδ IC50 (nM) | α/δ |
|---|---|---|---|---|---|
| 27 | 24 | 83 | 28 | 77 | 63 |
| 29 | 19 | 22 | 30 | 41 | 15 |
| 31 | 27 | 24 | 32 | 38 | 23 |
| 33 | 47.1 | 113 | 34 | 18.2 | 202 |
| 35 | 20 | 227 | 36 | 17 | 239 |
| 37 | 117 | 42 | 38 | 15.8 | 28 |
| 39 | 22 | 58 | | | |

TABLE 2

| Compound No. | β/δ | γ/δ | Compound No. | β/δ | γ/δ |
|---|---|---|---|---|---|
| 7 | 166 | >322 | 10 | 31 | >1000 |
| 15 | >29 | >29 | 16 | 341 | >650 |
| 23 | 40 | >625 | 28 | >129 | >129 |
| 34 | 360 | >549 | 35 | 322 | >500 |
| 36 | 366 | >588 | 37 | >85 | >85 |

Effect Example 2

Assay for Screening the Drugs for Inhibiting Human Raji Cell TNF-α Generation Induced by Human IgM 1. Raji cell line (human Burkitt's lymphoma origin) (ATCC, Cat#CCL-86) was used.
2. Raji cells were applied onto the 96-well plate with 1×10⁵/well.
3. The compounds to be screened were diluted to the corresponding test concentration, and added to the cell culture system 30 minutes prior to IgM stimulation.
4. 10 g/ml IgM monoclonal antibody (JACKSON, Cat#109-006-129) was added to the cell culture system in order to stimulate the cells generating TNF-α.
5. After 24 hours, the amount of TNF-α produced by the cell line was determined by ELISA.
6. The inhibition rates at each concentration of the compound were calculated and plotted to calculate 50% inhibition rate (IC50), and the specific results were shown in table 3.

TABLE 3

| IC50 against TNF-α of partial compounds | | | |
|---|---|---|---|
| Compound No. | TNF-α IC50 (nM) | Compound No. | TNF-α IC50 (nM) |
| 1 | 29.1 | 2 | 92.7 |
| 3 | 31.7 | 7 | 34.8 |
| 8 | 28.4 | 10 | 66.0 |
| 16 | 20.1 | 18 | 15.2 |
| 23 | 88.7 | 27 | 230.1 |
| 30 | 351.8 | 33 | 260.0 |
| 34 | 66.0 | 35 | 105.1 |
| 36 | 27.0 | 38 | 32.0 |
| 39 | 107.5 | | |

From the test results above it can be determined that, the compounds of the present invention have an excellent selective inhibition against PI3Kδ and are a type of selective inhibitor which possesses stronger inhibitory activity against PI3Kδ than that against PI3Kα, PI3Kβ or PI3Kγ and can be an excellent immunosuppressant, and can be an agent useful for treating or preventing rejection responses in a variety of organ transplantation, allergic diseases (asthma, atopic dermatitis etc.), autoimmune diseases (rheumatoid arthritis, psoriasis, ulcerative colitis, Crohn's disease, systemic lupus erythematosus etc.), and neoplastic hematologic disorder and so on.

Though the embodiments of the present invention are described above, a person skilled in the art should understand that these embodiments are just illustrated for explanation, without departing from the principle and substance of the present invention, a variety of modifications and alterations can be made to these embodiments. Therefore, the protection scope of the present invention is defined by the attached claims.

The invention claimed is:

1. A fused heterocyclic compound represented by formula I or formula III, or a pharmaceutically acceptable salt, hydrate, solvate, polymorph or pro-drug thereof, wherein,
in the formula I,
$A_1$ is N;
$A_2$ is N;
$R^2$ is —$(CR^8R^9)_m NR^5R^6$, —$O(CR^8R^9)_m CR^5R^6$ or —$O(CR^8R^9)_m NR^5R^6$;
$R^3$ is a hydrogen, a deuterium, a halogen or a $C_{1-3}$ alkyl;
A is $CR^{4a}$; $R^{4a}$ is a hydrogen, a halogen or a $C_{1-3}$ alkyl;
D is N;
E is $CR^{4e}$; $R^{4e}$ is a hydrogen, a $C_{1-3}$ alkoxy or —$NR^5R^6$;
G is $CR^{4g}$; $R^{4g}$ is —$NHS(O)_2R^5$;
J is $CR^{4j}$; $R^{4j}$ is a hydrogen, a halogen or a $C_{1-3}$ alkyl;
or, $R^{4j}$ and $R^{4g}$, together with the atoms to which they are
   attached form a saturated, unsaturated or partially unsaturated 5- or 6-membered heterocyclic ring, wherein the 5- or 6-membered heterocyclic ring is fused to the 6-membered ring containing A, D, E, G and J; the 5-membered heterocyclic ring is a 5-membered nitrogen-containing heterocyclic ring;

ring Q is a benzene;
R¹ is a halogen;
R⁵, R⁶ and R⁷ are each independently a hydrogen, —(CH₂)₂₋₃NH₂ or a C₁₋₆ alkyl, or R⁵, R⁶ together with the nitrogen or carbon atoms to which they are directly attached form a heterocyclic ring or a cycloalkyl, wherein the heterocyclic ring or the cycloalkyl is optionally substituted by the substituent selected from the group consisting of —(CH₂)$_m$OR⁷, —SO₂R⁷, —C(=O)R⁷, a C₁₋₃ alkyl, a C₃₋₆ carbocyclic group and a C₂₋₅ heterocyclic group; wherein the heterocyclic ring is a nitrogen-containing or an oxygen-containing 4- to 6-membered heteroalicyclic ring, and the cycloalkyl is a 4- to 6-membered cycloalkyl;
(CR⁸R⁹)$_m$ represents that 0 to m (CR⁸R⁹) are linked, R⁸ and R⁹ are the substituents attached to the formed carbon chain, wherein each R⁸ and R⁹ are the same or different from each other, and are each independently a hydrogen, a deuterium, a halogen or a C₁₋₃ alkyl;
m, k and k1 are independently 0 or 1;
and wherein in the formula III,
A₁ is N;
A₂ is N;
R² is —(CR⁸R⁹)$_m$NR⁵R⁶ or —(CR⁸R⁹)$_m$OR⁵;
R³ is a hydrogen, a deuterium, a halogen or a C₁₋₃ alkyl;
A is CR$^{4a}$; R$^{4a}$ is a hydrogen, a halogen or a C₁₋₃ alkyl;
E is CR$^{4e}$; R$^{4e}$ is a C₁₋₆ alkoxy;
J is CR$^{4j}$; R$^{4j}$ is a hydrogen;
ring Q' is a benzene or a 5-membered heterocyclic ring;
R¹ is a halogen, —CN or a C₁₋₁₂ alkyl;
R⁵, R⁶, R⁷ and R⁷' are each independently a hydrogen, a C₁₋₆ alkyl, —(CH₂)₂₋₃NH₂, a C₃₋₆ carbocyclic group or a C₂₋₅ heterocyclic group, or R⁵, R⁶ and the nitrogen atom to which they are directly attached form a heterocyclic ring which is optionally substituted by a substituent selected from the group consisting of —NR⁷R⁷', a C₁₋₃ alkyl, a C₃₋₆ carbocyclic group and a C₂₋₅ heterocyclic group;
(CR⁸R⁹)$_m$ represents that 0 to m (CR⁸R⁹) are linked, R⁸ and R⁹ are the substituents attached to the formed carbon chain, wherein each R⁸ and R⁹ are the same or different from each other, and are each independently a hydrogen, a deuterium or a C₁₋₃ alkyl;
m, k and k1 are independently 0 or 1;
wherein the alkyl, alkoxy, cycloalkyl, carbocyclic ring, heterocyclic ring, or heterocyclic group can be optionally substituted by a substituent selected from the group consisting of a halogen, a hydroxyl, —CN, —CF₃, —NO₂, oxo, R⁵, —C(=Y)R⁵, —C(=Y)OR⁵, —C(=Y)NR⁵R⁶, —(CR⁸R⁹)$_m$NR⁵R⁶, —(CR⁸R⁹)$_m$OR⁵, —NR⁵R⁶, —NR⁷C(=Y)R⁵, —NR⁷C(=Y)OR⁶, —NR⁷C(=Y)NR⁵R⁶, —(CR⁸R⁹)$_m$NR⁷SO₂R⁵, =NR⁷, OR⁵, —OC(=Y)R⁵, —OC(=Y)OR⁵, —OC(=Y)NR⁵R⁶, —OS(O)₂(OR⁵), —OP(=Y)(OR⁵)(OR⁶), —OP(OR⁵)(OR⁶), —SR⁵, —S(O)R⁵, —S(O)₂R⁵, —S(O)₂NR⁵R⁶, —S(O)(OR⁵), —S(O)₂(OR⁵), —SC(=Y)R⁵, —SC(=Y)OR⁵, —SC(=Y)NR⁵R⁶, a C₁₋₁₂ alkyl, a C₂₋₈ alkenyl, a C₂₋₈ alkynyl, a C₃₋₁₂ carbocyclic group, a C₂₋₂₀ heterocyclic group, a C₆₋₂₀ aryl and a C₁₋₂₀ heteroaryl.

2. The fused heterocyclic compound, pharmaceutically acceptable salt, hydrate, solvate, polymorph or pro-drug thereof as defined in claim 1, which is of the formula I wherein, R² has a structure selected from the group consisting of

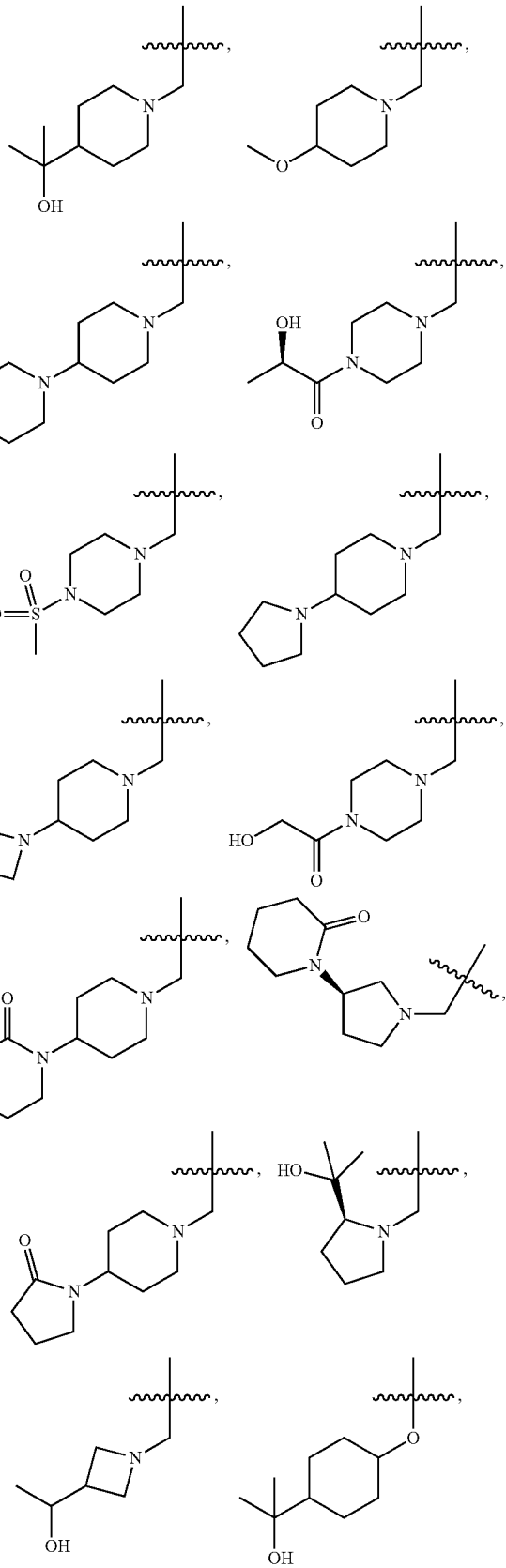

-continued

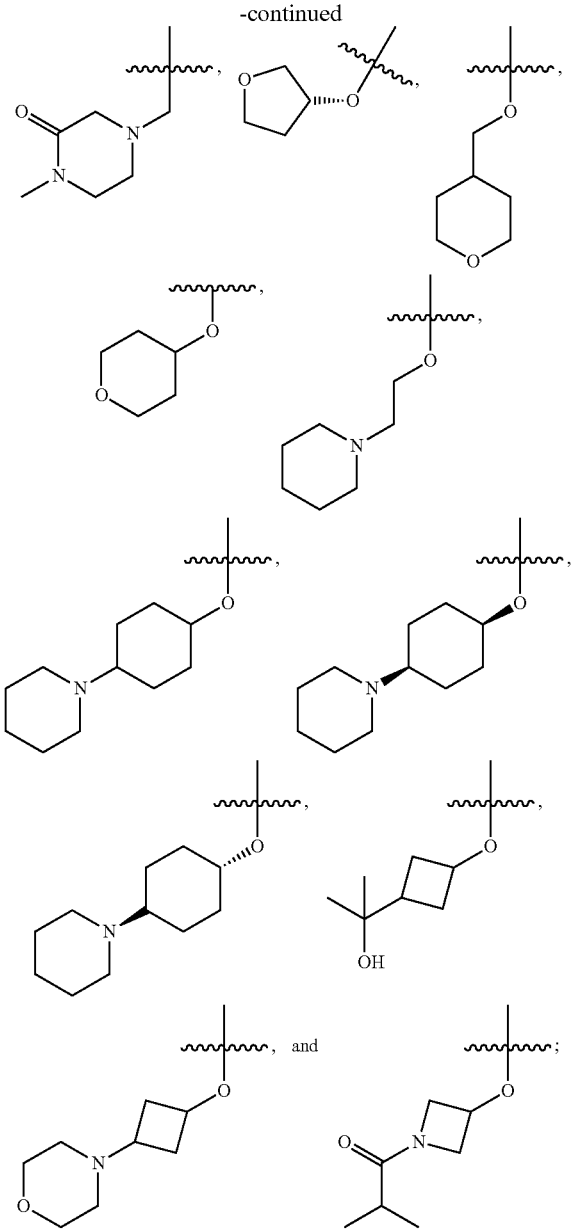

$R^3$ is a hydrogen;
A is $CR^{4a}$; $R^{4a}$ is a hydrogen;
D is N;
E is $CR^{4e}$; $R^{4e}$ is a hydrogen, a methoxy or —$NH_2$;
G is N or $CR^{4g}$; $R^{4g}$ is

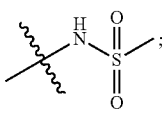

J is $CR^{4j}$; $R^{4j}$ is a hydrogen;
or, $R^{4j}$ and $R^{4g}$, together with the atoms to which they are attached form a saturated, unsaturated or partially unsaturated 5- or 6-membered heterocyclic ring, the 5- or 6-membered heterocyclic ring is fused to the 6-membered ring containing A, D, E, G and J;

ring Q is a benzene;
$R^1$ is fluorine; and
m, k and k1 are independently 0 or 1.

3. The fused heterocyclic compound, pharmaceutically acceptable salt, hydrate, solvate, polymorph or pro-drug thereof as defined in claim 1, which is of the formula I wherein, $R^{4j}$ and $R^{4g}$, together with the atoms to which they are attached form a saturated, unsaturated or partially saturated 5-membered heterocyclic ring, the 5-membered heterocyclic ring is fused to the 6-membered ring containing A, D, E, G and J; the 5-membered heterocyclic ring is 5-membered nitrogen-containing heterocyclic ring; the 5-membered nitrogen-containing heterocyclic ring is a pyrazole or a pyrrole;

the heterocyclic ring formed by $R^5$, $R^6$, with the nitrogen atom to which they are directly attached is a nitrogen-containing 6-membered heteroalicyclic ring; the nitrogen-containing 6-membered heteroalicyclic ring is a piperidine or a piperazidine.

4. The fused heterocyclic compound, pharmaceutically acceptable salt, hydrate, solvate, polymorph or pro-drug thereof as defined in claim 1, which is of the formula I and is a compound selected from the group consisting of

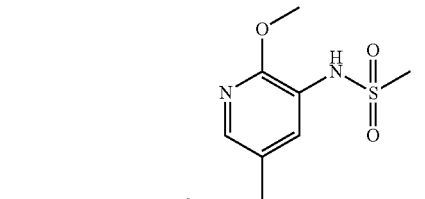

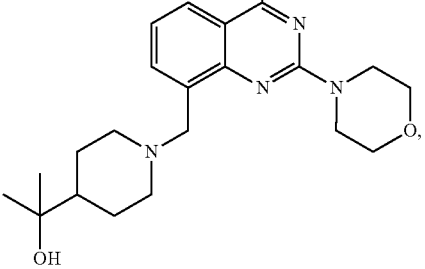

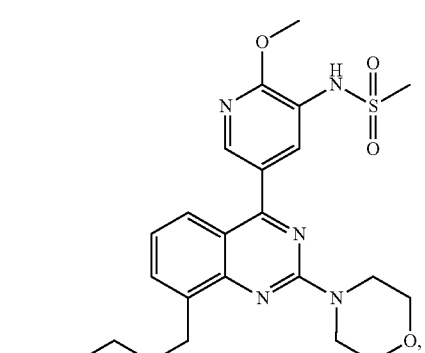

3
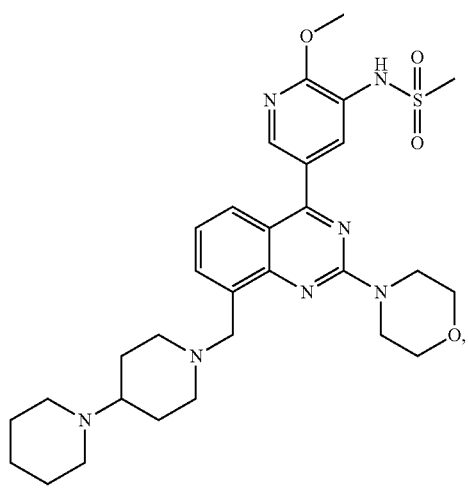
4
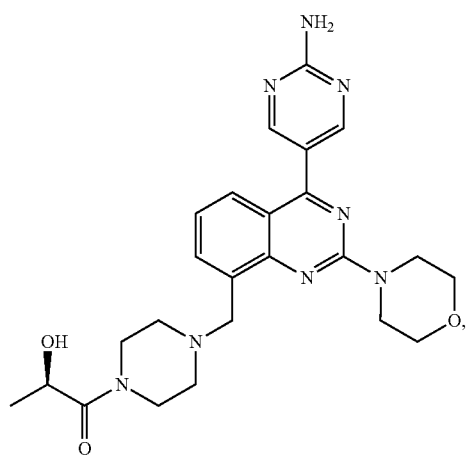
5
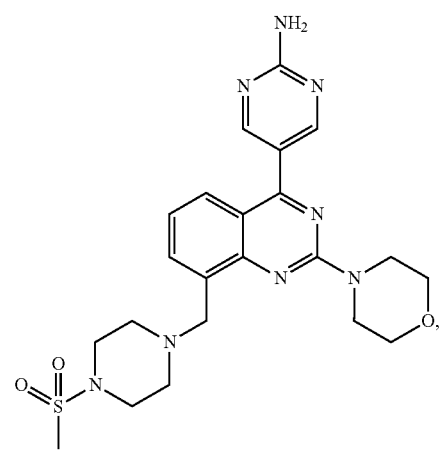
6
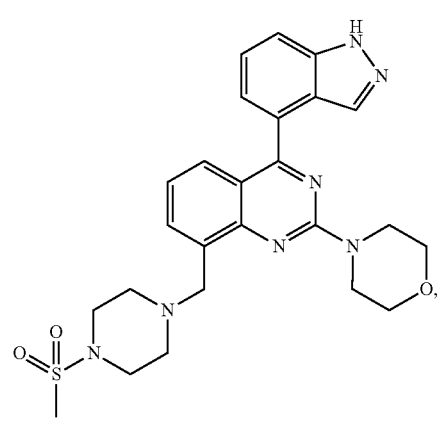
7
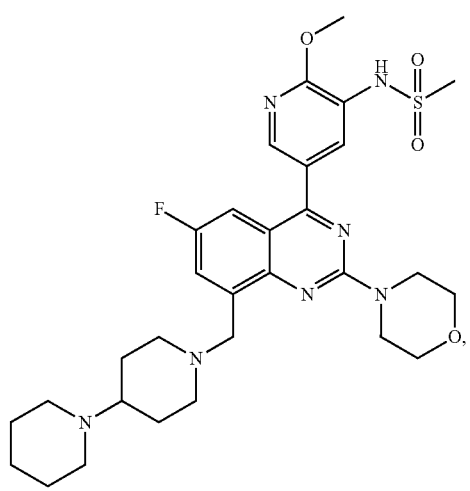
8
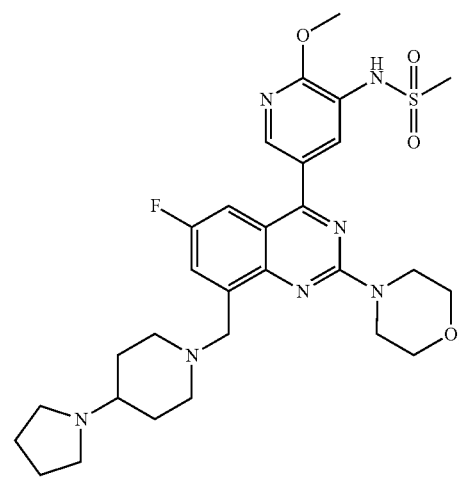

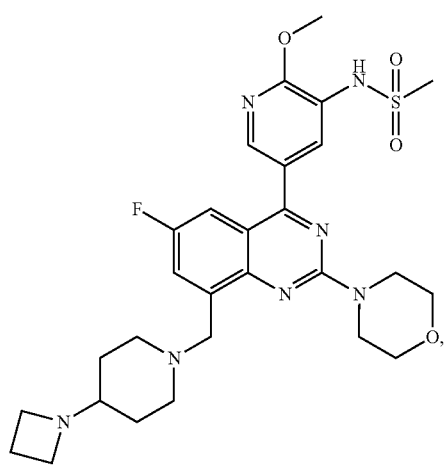
9
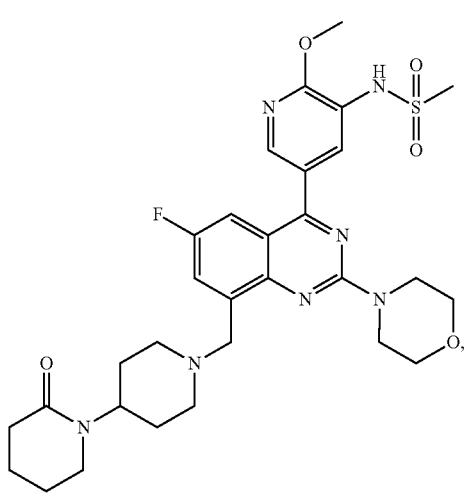
23
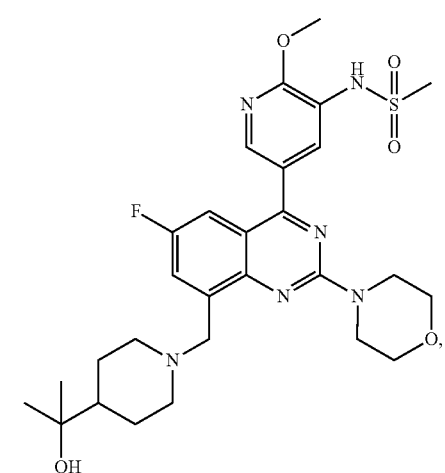
10
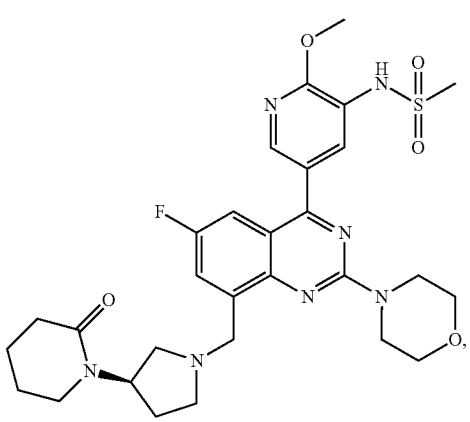
24
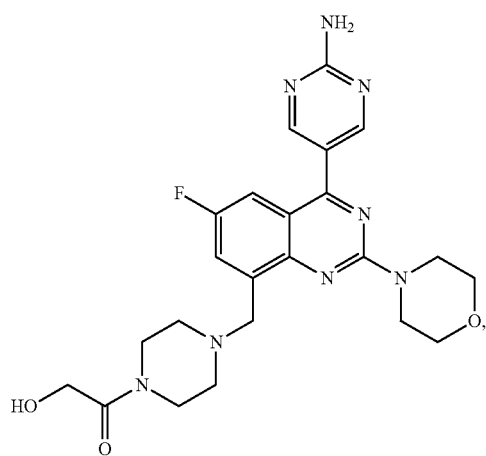
22
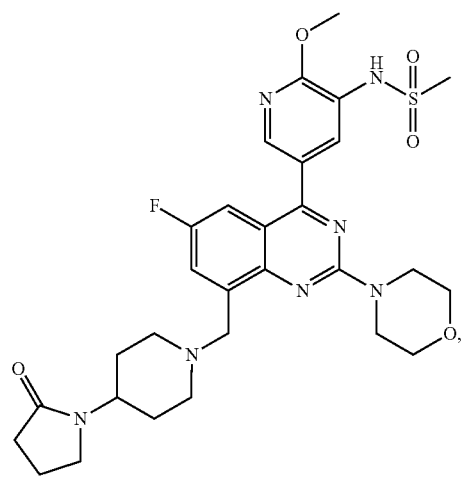
25

-continued
26
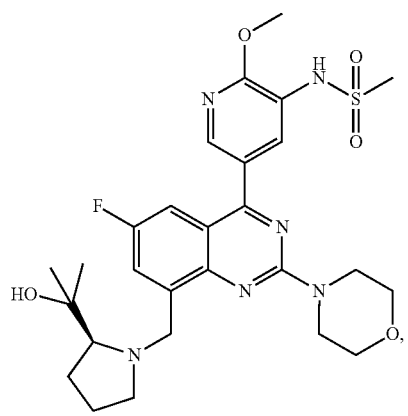
27
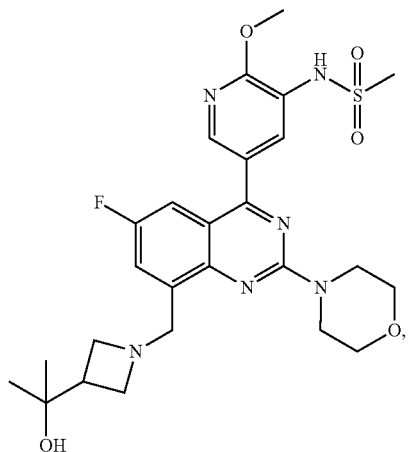
28
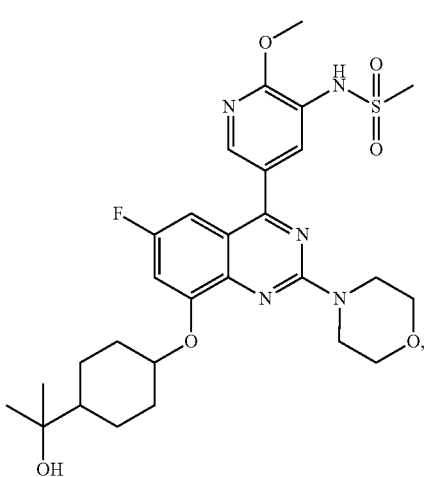
-continued
29
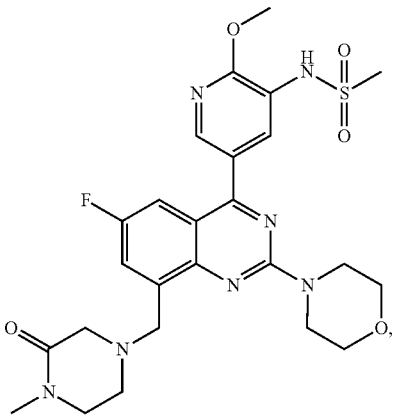
30
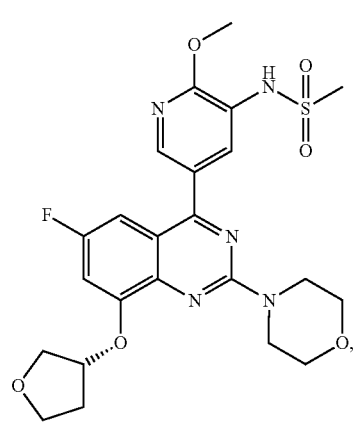
31
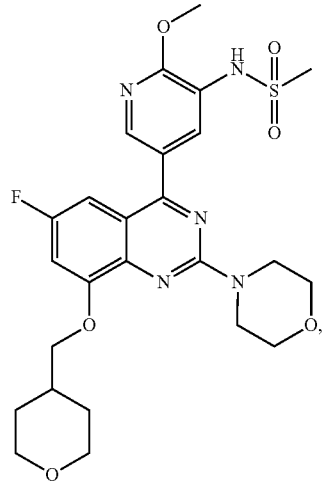

32
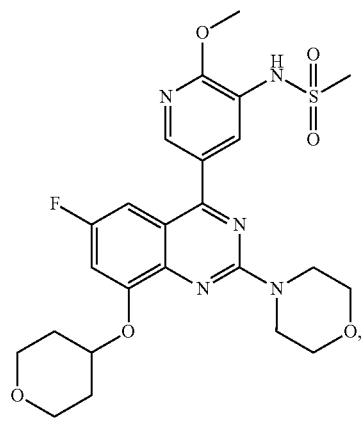
33
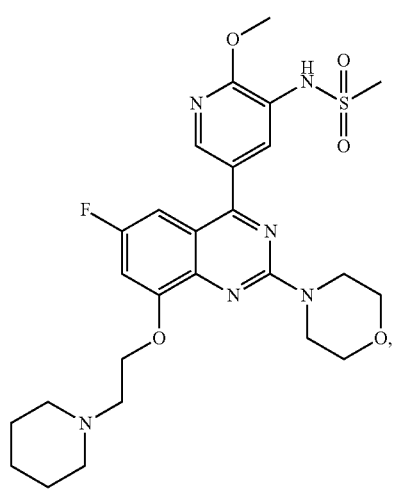
34
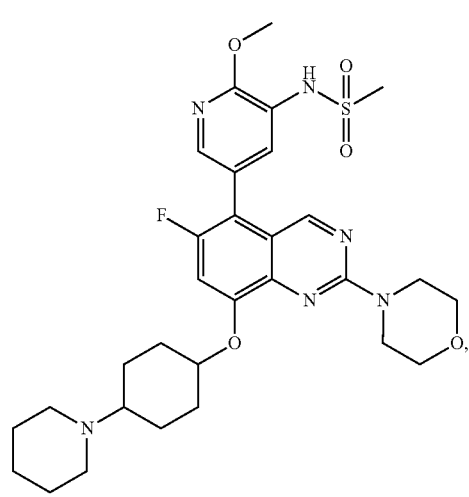
35
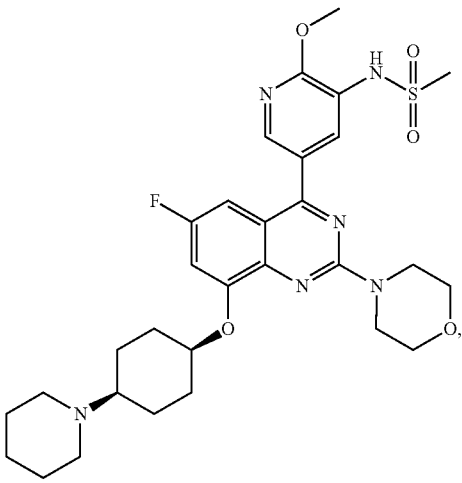
36
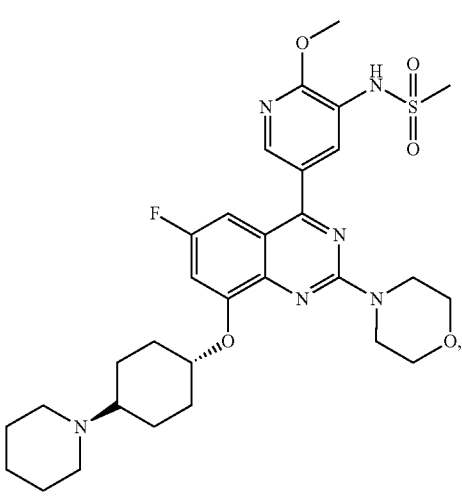
37
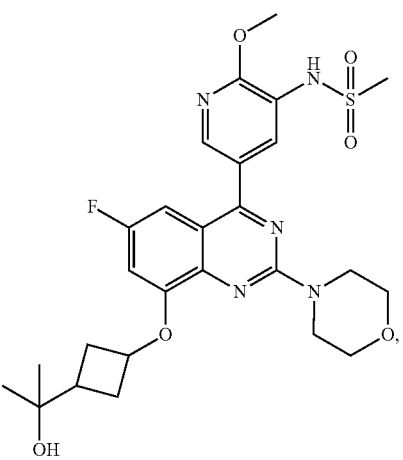

-continued

38

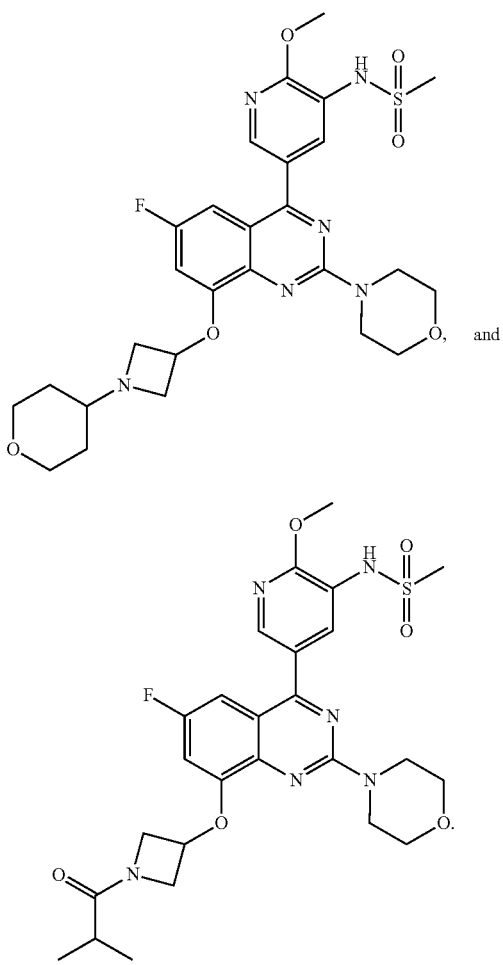

39

5. The fused heterocyclic compound, pharmaceutically acceptable salt, hydrate, solvate, polymorph or pro-drug thereof as defined in claim 1, wherein in the formula III, R² is —(CR⁸R⁹)ₘNR⁵R⁶ or —(CR⁸R⁹)ₘOR⁵;

R³ is a hydrogen or a deuterium;

A is CR⁴ᵃ; R⁴ᵃ is a hydrogen;

E is CR⁴ᵉ; R⁴ᵉ is a C₁₋₃ alkoxy;

J is CR⁴ʲ; R⁴ʲ is a hydrogen;

ring Q' is a benzene or a 5-membered heterocyclic ring, wherein the 5-membered heterocyclic ring is a thiophene or an imidazole;

R¹ is a C₁₋₃ alkyl;

R⁵, R⁶, R⁷ and R⁷' are each independently a hydrogen, a C₁₋₃ alkyl, —(CH₂)₂₋₃NH₂, a C₃₋₆ carbocyclic group or a C₂₋₅ heterocyclic group, or R⁵, R⁶ and the nitrogen atom to which they are directly attached form a heterocyclic ring which is optionally substituted by the substituent selected from the group consisting of —NR⁷R⁷', a C₁₋₃ alkyl, a C₃₋₆ carbocyclic group or a C₂₋₅ heterocyclic group; the C₂₋₅ heterocyclic group is a piperidine, a pyran, a tetrahydropyrrole and an oxetane;

(CR⁸R⁹)ₘ represents that 0 to m (CR⁸R⁹) are linked, R⁸ and R⁹ are the substituents attached to the formed carbon chain, wherein each R⁸ and R⁹ are the same or different from each other, and are each independently a hydrogen or a deuterium; and m, k and k1 are independently 0 or 1.

6. The fused heterocyclic compound, pharmaceutically acceptable salt, hydrate, solvate, polymorph or pro-drug thereof as defined in claim 5, wherein in the formula III, R² is

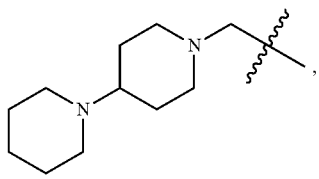

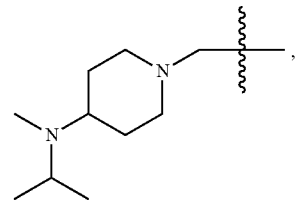

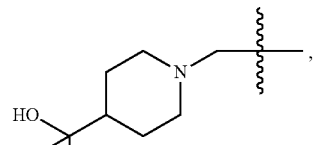

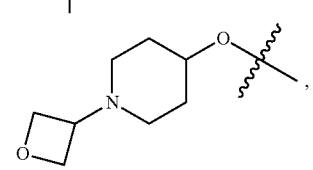

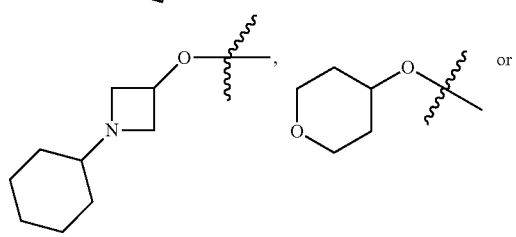

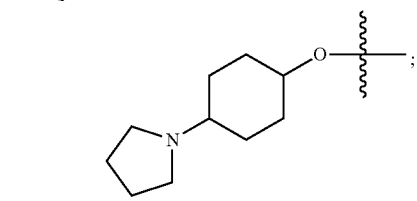

R³ is a hydrogen or a deuterium;

A is CR⁴ᵃ; R⁴ᵃ is a hydrogen;

E is CR⁴ᵉ; R⁴ᵉ is a methoxy;

J is CR⁴ʲ; R⁴ʲ is a hydrogen;

ring Q' is a benzene or a 5-membered heterocyclic ring, wherein the 5-membered heterocyclic ring is a thiophene or an imidazole;

R¹ is a methyl; and m, k and k1 are independently 0 or 1.

7. The fused heterocyclic compound, pharmaceutically acceptable salt, hydrate, solvate, polymorph or pro-drug thereof as defined in claim 1, which is of the formula III and is a compound selected from the group consisting of:

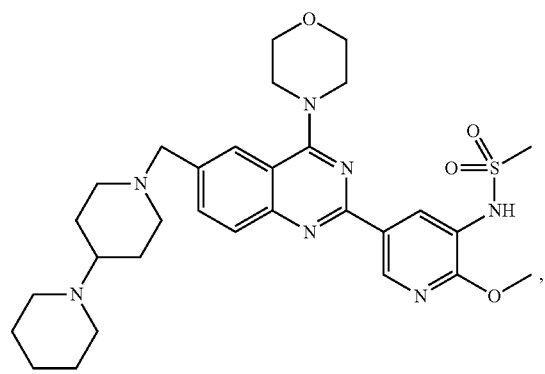
15
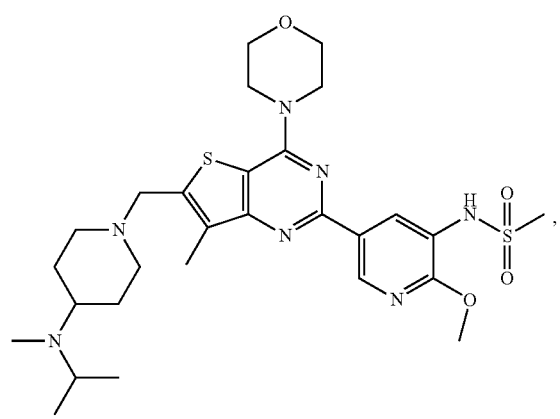
16
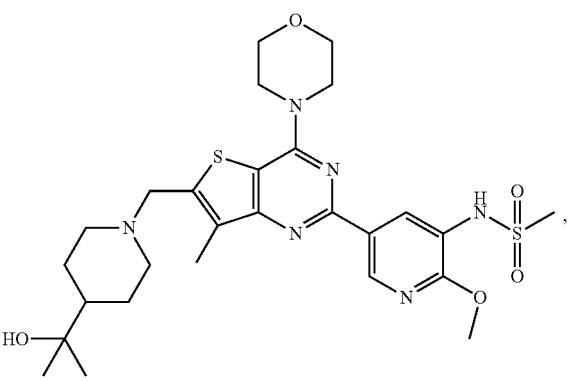
17
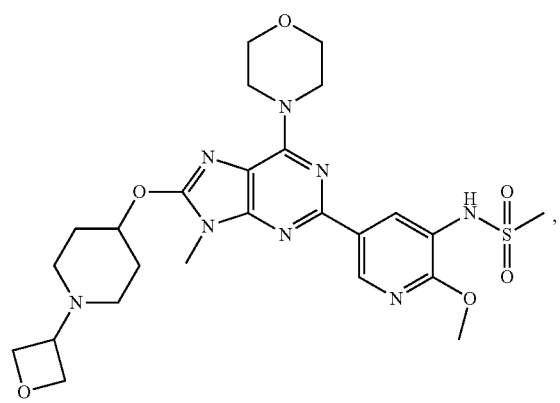
18
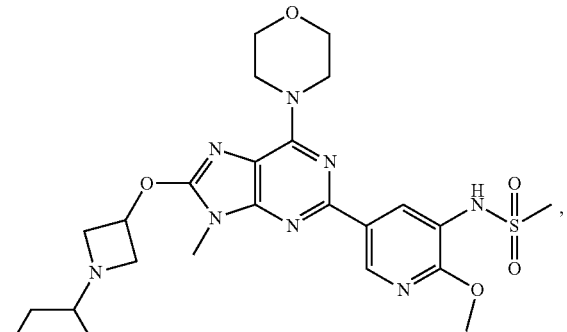
19
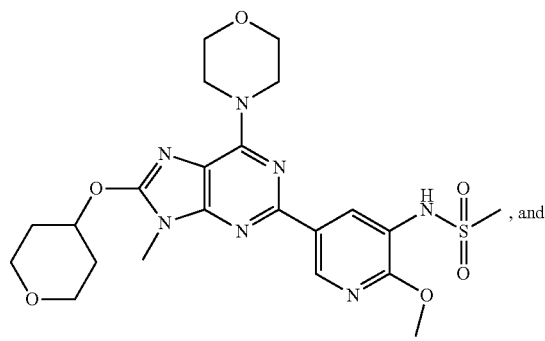
20
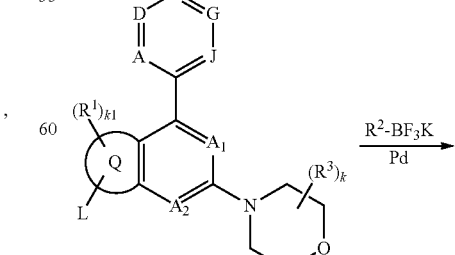
21
8. A process for preparing the fused heterocyclic compound, pharmaceutically acceptable salt, hydrate, solvate, polymorph or pro-drug thereof as defined in claim 1, by one of reaction routes I, III or IV, wherein
reaction route I comprises the following steps:

107

-continued

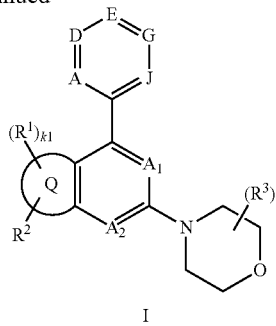

I reaction route III comprises the following steps:

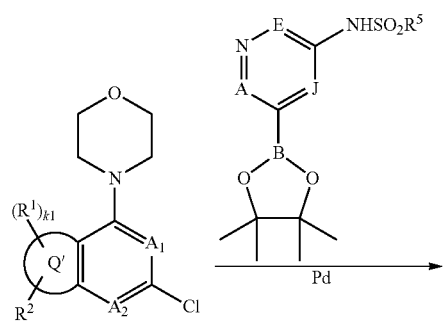

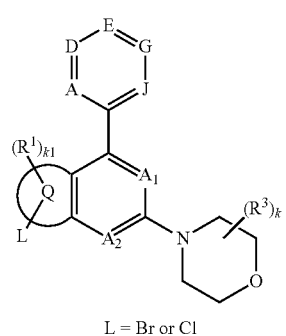

III reaction route IV comprises the following steps:

L = Br or Cl

108

-continued

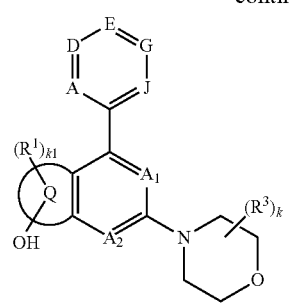

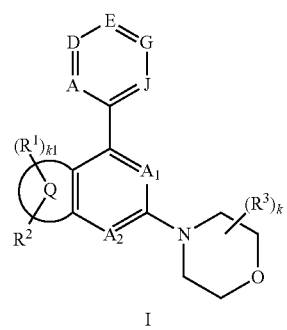

I wherein, when R² is —O(CR⁸R⁹)ₘCR⁵R⁶ or —O(CR⁸R⁹)ₘNR⁵R⁶ in the formula I, the reaction route IV is utilized to prepare the compound, when R² is not —O(CR⁸R⁹)ₘCR⁵R⁶ or —O(CR⁸R⁹)ₘNR⁵R⁶ in the formula I, the reaction route I is utilized to prepare the compound; X¹ is Cl, Br or I.

9. A compound as shown below:

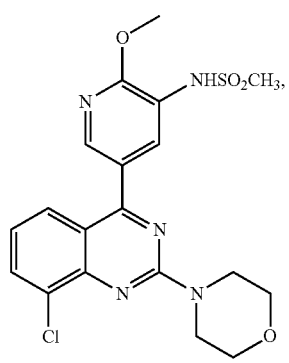

1-a

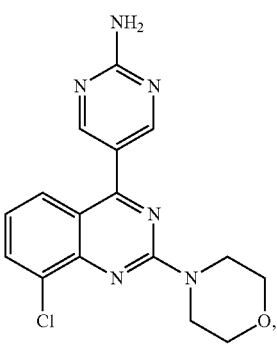

4-d

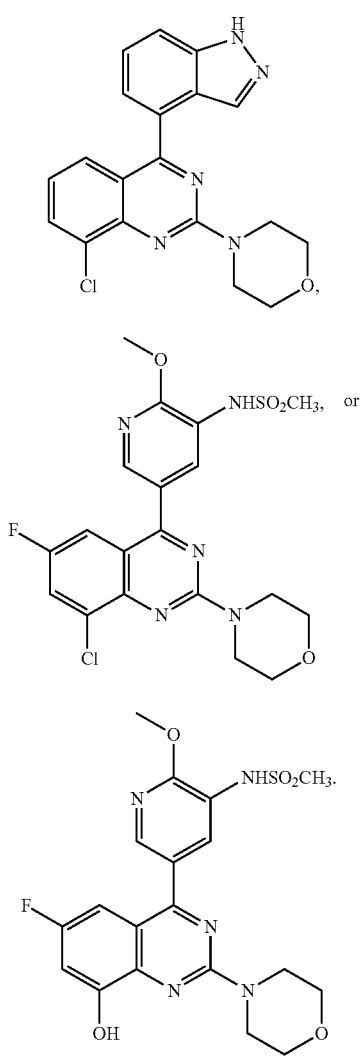

10. A pharmaceutical composition comprising a therapeutically effective dosage of the fused heterocyclic compound, pharmaceutically acceptable salt, hydrate, solvate, polymorph and pro-drug thereof as defined in claim 1, and a pharmaceutically acceptable carrier.

11. A kinase inhibitor, which comprises the fused heterocyclic compound, pharmaceutically acceptable salt, hydrate, solvate, polymorph or pro-drug thereof as defined in claim 1.

12. The kinase inhibitor as defined in claim 11, wherein the kinase is PI3 kinase.

13. The kinase inhibitor as defined in claim 12, wherein the kinase is p110 δ subtype of PI3 kinase.

14. A process for treating a disease related to kinase, which disease is selected from the group consisting of rheumatoid arthritis, psoriasis, ulcerative colitis, Crohn's disease, systemic lupus erythematosus, neoplastic hematologic disorder, asthma and atopic dermatitis, in a subject in need thereof, comprising administering an effective amount of the fused heterocyclic compound, pharmaceutically acceptable salt, hydrate, solvate, polymorph or pro-drug thereof as defined in claim 1, to the subject.

15. A process for treating a disease related to kinase, which disease is selected from the group consisting of rheumatoid arthritis, psoriasis, ulcerative colitis, Crohn's disease, systemic lupus erythematosus, neoplastic hematologic disorder, asthma and atopic dermatitis, in a subject in need thereof, comprising administering an effective amount of the pharmaceutical composition as defined in claim 10 to the subject.

* * * * *